US012600765B2

(12) United States Patent
Jeon et al.

(10) Patent No.: US 12,600,765 B2
(45) Date of Patent: *Apr. 14, 2026

(54) TARGET FOR ANTI-CANCER AND IMMUNE-ENHANCING

(71) Applicant: GENOME AND COMPANY, Seongnam-si (KR)

(72) Inventors: Bu-Nam Jeon, Seongnam-si (KR); Yun Yeon Kim, Seongnam-si (KR); Suro Lee, Seongnam-si (KR); Youn Kyung Houh, Seongnam-si (KR); Joo-Yeon Chung, Seongnam-si (KR); Areum Jeong, Seongnam-si (KR); Mi Young Cha, Seongnam-si (KR)

(73) Assignee: GENOME AND COMPANY, Seongnam-si (KR)

( * ) Notice: Subject to any disclaimer, the term of this patent is extended or adjusted under 35 U.S.C. 154(b) by 1291 days.

This patent is subject to a terminal disclaimer.

(21) Appl. No.: 17/227,173

(22) Filed: Apr. 9, 2021

(65) Prior Publication Data

US 2021/0230256 A1 Jul. 29, 2021

Related U.S. Application Data

(63) Continuation-in-part of application No. 16/375,377, filed on Apr. 4, 2019, now abandoned.

(60) Provisional application No. 62/652,948, filed on Apr. 5, 2018.

(51) Int. Cl.
| | |
|---|---|
| C07K 16/18 | (2006.01) |
| A61K 39/00 | (2006.01) |
| A61P 35/00 | (2006.01) |
| C12N 15/113 | (2010.01) |
| C12Q 1/6886 | (2018.01) |
| G01N 33/68 | (2006.01) |

(52) U.S. Cl.
CPC .............. *C07K 16/18* (2013.01); *A61P 35/00* (2018.01); *C12N 15/113* (2013.01); *C12Q 1/6886* (2013.01); *G01N 33/6893* (2013.01); *A61K 2039/505* (2013.01); *C12N 2310/12* (2013.01); *C12N 2310/141* (2013.01); *C12N 2310/531* (2013.01)

(58) Field of Classification Search
None
See application file for complete search history.

(56) References Cited

U.S. PATENT DOCUMENTS

| | | |
|---|---|---|
| 2012/0015374 A1 | 1/2012 | Jung et al. |
| 2016/0122825 A1 | 5/2016 | Mills et al. |
| 2017/0216289 A1 | 8/2017 | Pendergast |

| | | |
|---|---|---|
| 2020/0263258 A1 | 8/2020 | Boardman et al. |
| 2021/0230256 A1 | 7/2021 | Jeon et al. |
| 2024/0182563 A1 | 6/2024 | Jeon et al. |
| 2024/0209081 A1 | 6/2024 | Jeon et al. |

FOREIGN PATENT DOCUMENTS

| | | | | |
|---|---|---|---|---|
| EP | 2177615 A1 | 4/2010 | | |
| JP | 2008-56647 A | 3/2008 | | |
| KR | 10-2017-0048002 A | 5/2017 | | |
| KR | 10-2019-0116930 A | 10/2019 | | |
| WO | WO2001090170 A1 * | 5/2000 | ....... | C07K 14/70503 |
| WO | WO-2008051326 A2 * | 5/2008 | ......... | C07K 14/4711 |
| WO | 2013/022872 A1 | 2/2013 | | |
| WO | 2016/127220 A1 | 8/2016 | | |
| WO | 2019/194586 A1 | 10/2019 | | |
| WO | 2022/216014 A1 | 10/2022 | | |
| WO | 2022/231032 A1 | 11/2022 | | |

OTHER PUBLICATIONS

Bang et al. "Trastuzumab in combination with chemotherapy versus chemotherapy alone for treatment of HER2-positive advanced gastric or gastro-oesophageal junction cancer (ToGA): a phase 3, open-label, randomised controlled trial", Lancet. Aug. 28, 2010; 376(9742):687-97. (Year: 2010).*
Evenepoel et al. "Expression of Contactin 4 Is Associated With Malignant Behavior in Pheochromocytomas and Paragangliomas", J Clin Endocrinol Metab. Jan. 1, 2018;103(1):46-55 (Year: 2018).*
Fidler et al. "Biological heterogeneity of cancer", Human Vaccines & Immunotherapeutics 8:8, 1141-1142 (Year: 2012).*
The Merck Manuals Online Medical Library, [online]. Merck Research Laboratories, 2006-2007. [retrieved on Oct. 19, 2020]. < URL: https://www.merckmanuals.com/professional/hematology-and-oncology/overview-of-cancer/cellular-and-molecular-basis-of-cancer>. Cellular and Molecular Basis of Cancer (Year: 2020).*
Ali Dianatpour et al., "Long Non Coding RNA Expression Intersecting Cancer and Spermatogenesis: a Systematic Review", Aisian Pacific Journal of Cancer Prevention, 2010, 10 pgs., vol. 18.
Lucie Evenepoel et al., "Expression of Contactin 4 Is Associated With Malignant Behavior in Pheochromocytomas and Paragangliomas", J Clin Endocrinol Metab, Jan. 2018, vol. 103, No. 1 (25 pages).
Notification of Reason for Refusal issued Jan. 13, 2021 in related Korean Patent Application No. 10-2019-0039278.
Baig et al., "Distortion of the normal function of synaptic cell adhesion molecules by genetic variants as a risk for autism spectrum disorders", Brain Research Bulletin, vol. 129, 2017, pp. 82-90.

(Continued)

*Primary Examiner* — Daniel E Kolker
*Assistant Examiner* — Peter Johansen
(74) *Attorney, Agent, or Firm* — Sughrue Mion, PLLC

(57) ABSTRACT

The present disclosure provides a pharmaceutical composition for treating or preventing cancer, comprising inhibitors of KIRREL3, CNTN4 and/or CD351. In addition, the present disclosure provides a pharmaceutical composition for immune-enhancing, comprising inhibitors of KIRREL3, CNTN4 and/or CD351. Furthermore, the present disclosure provides a method of screening of anti-cancer agent using KIRREL3, CNTN4 and/or CD351, and a method of providing information necessary for analysis of cancer prognosis using KIRREL3, CNTN4 and/or CD351.

18 Claims, 41 Drawing Sheets

Specification includes a Sequence Listing.

(56)                    References Cited

OTHER PUBLICATIONS

Beadling et al., "Gene expression of the IGF pathway family distinguishes subsets of gastrointestinal stromal tumors wild type for KIT and PDGFRA", Cancer Medicine, vol. 2, No. 1, 2013, pp. 21-31.

Cha et al., "Abstract 688: Anti-CNTN4 antibody, GENA-104A07 suppresses tumor growth in murine syngeneic tumor models by regulating T cell function", Cancer Res, vol. 81, 13 Supplement, No. 688, Jul. 1, 2021, pp. 1-4.

Durcan et al., "Identification of novel Kirrel3 gene splice variants in adult human skeletal muscle", BMC Physiology, vol. 14, No. 11, 2014, pp. 1-11.

Kim et al., "MedPacto, Genome & Company, NKMAX AACR Issue", Pancreatic Cancer Bactosertib + Onibide Preclinical Results, Mar. 12, 2021, pp. 1-8.

Manderson et al., "Molecular Genetic Analysis of a Cell Adhesion Molecule With Homology to L1CAM, Contactin 6, and Contactin 4 Candidate Chromosome 3p26pter Tumor Suppressor Genes in Ovarian Cancer", International Journal of Gynecological Cancer, vol. 19, No. 4, May 2009, pp. 513-525.

Shibuya et al., "Immune regulation by Fcα/μ receptor (CD351) on marginal zone B cells and follicular dendritic cells", Immunological Reviews, 2015, pp. 288-295 (9 pages total).

Shibuya et al., "A pro-inflammatory role of Fcα/μR on marginal zone B cells in sepsis", International Immunology, vol. 29, No. 11, Dec. 21, 2017, pp. 519-524.

Swarts et al., "An exploration of pathways involved in lung carcinoid progression using gene expression profiling", Carcinogenesis, vol. 34, No. 12, Aug. 8, 2013, pp. 2726-2737.

Tamir-Livne et al., "Adhesion molecule Kirrel3/Neph2 is required for the elongated shape of myocytes during skeletal muscle differentiation", The International Journal of Developmental Biology, vol. 61, 2017, pp. 337-345 (10 pages total).

* cited by examiner

FIG. 13A

Colon cancer

FIG. 13B

Colon cancer

FIG. 15C
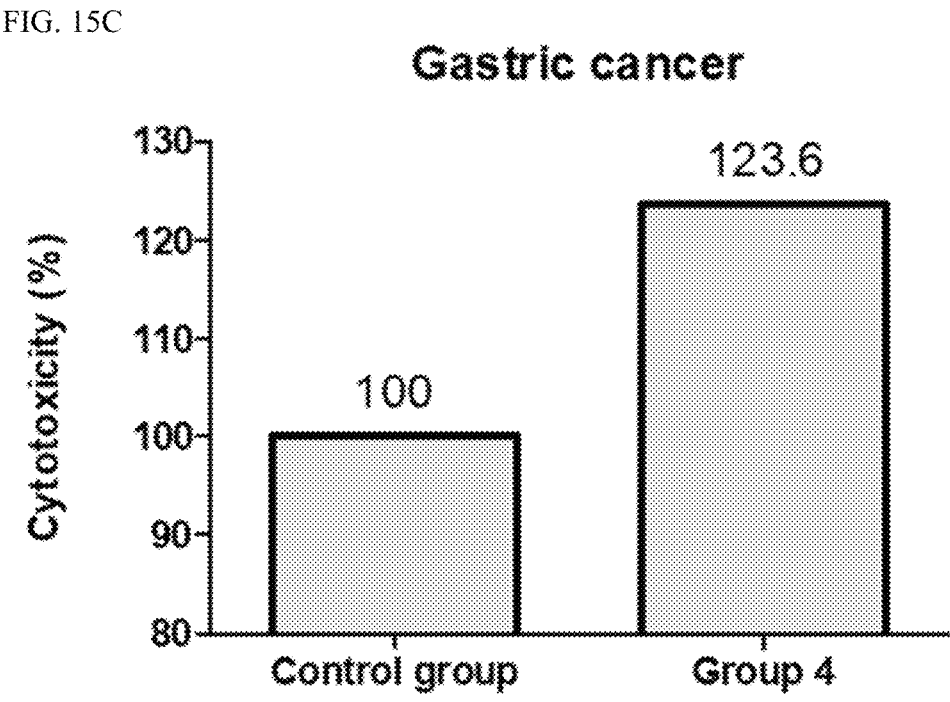
FIG. 15D
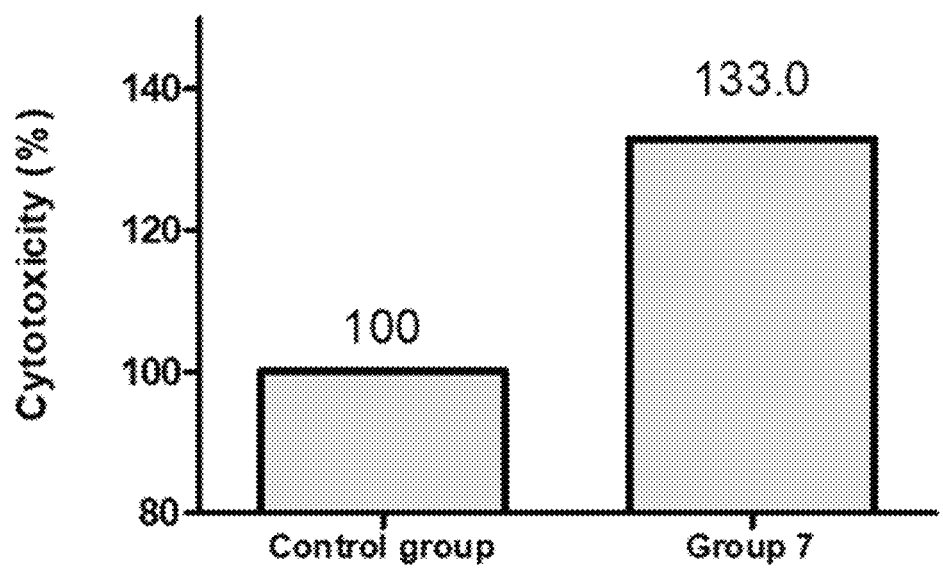

FIG. 16C
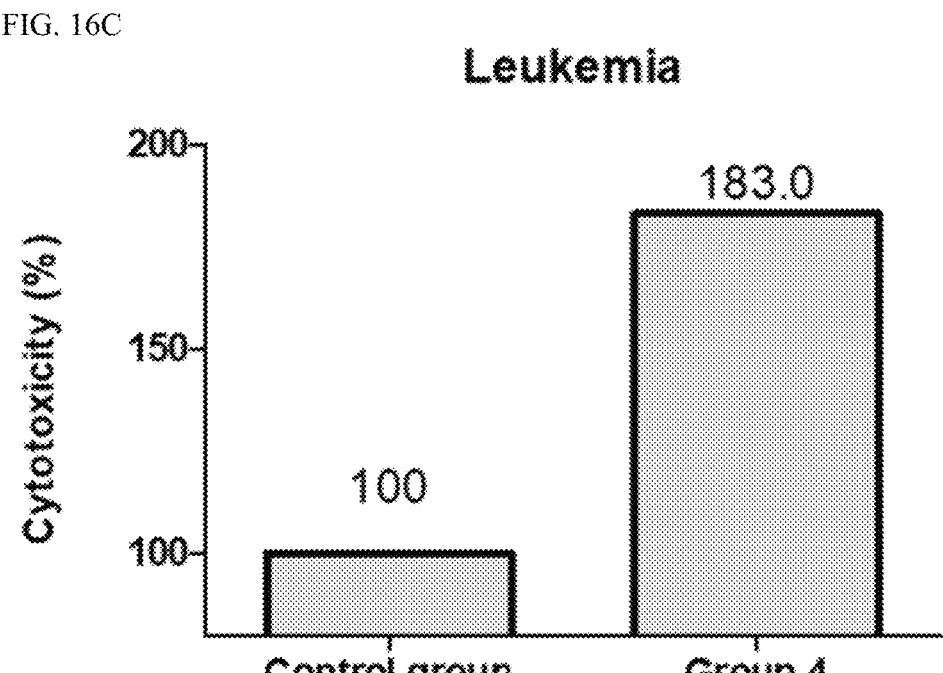
FIG. 16D
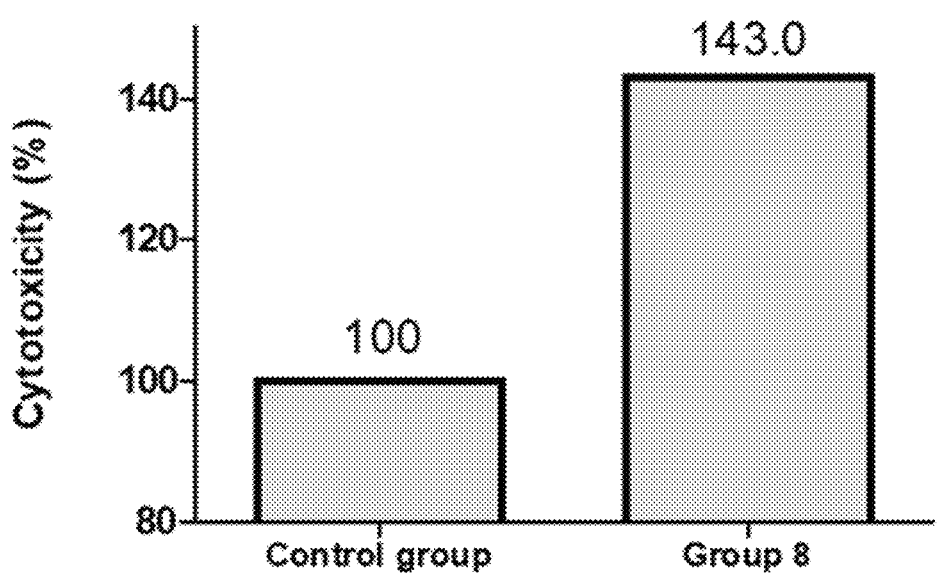

FIG. 17A

Lung cancer

FIG. 17B

Lung cancer

FIG. 18C

Colon cancer

FIG. 18D

Colon cancer

FIG. 19C
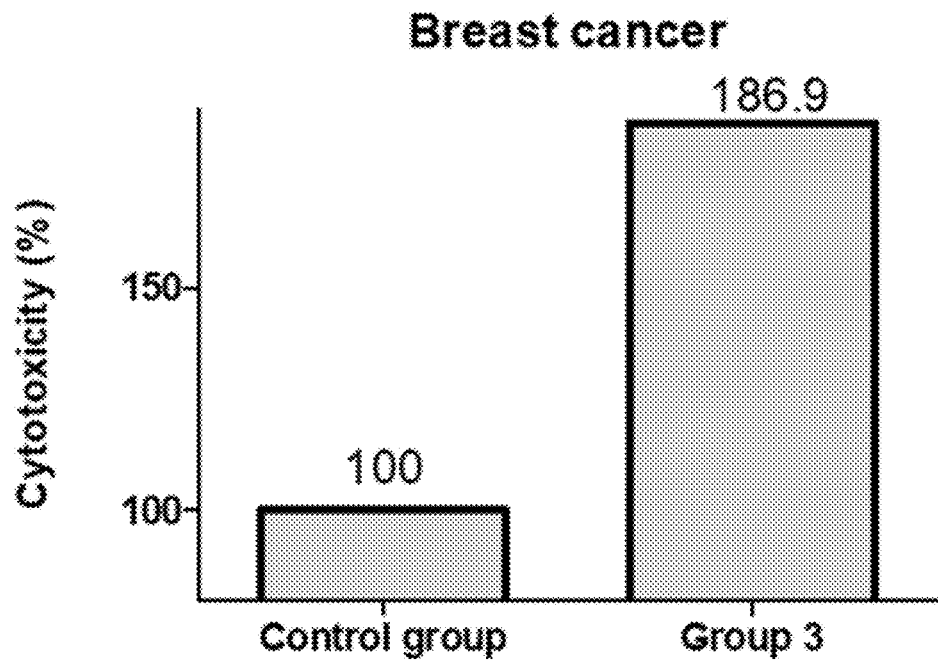
FIG. 19D
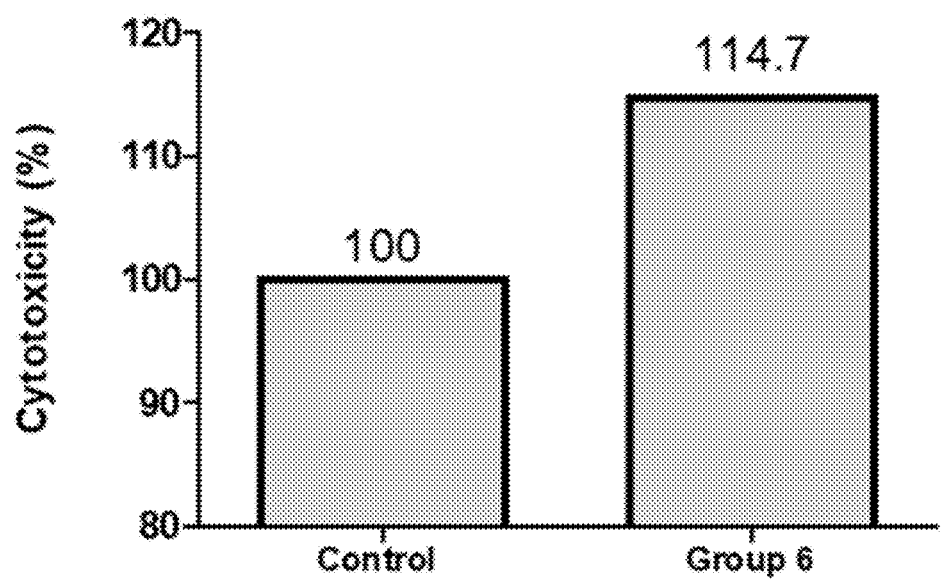

FN1 – FN2 domain SEQ ID NO: 29

**PPEAVTIDEITDTTAQLSWRPGPDNHSPITMYVIQARTPFSVGWQAVSTVPELIDGKTFTATV
VGLNPWVEYEFRTVAANVIGIGEPSRPSEKRRTEEALPEVTPANVSGGGGSKSELVITWETV
PEELQNGRGFGYVVAFRPYGKMIWMLTVLASADASRYVFRNESVHPFSPFEVKVGVFNNK
GEGPFSPTTVVYSAEE**

KPI domain SEQ ID NO: 30

RAMISRWYFDVTEGK

FIG. 28

| AB1 VL | ALTQPSSVSANLGETVKITCSGSSGSYGWYQQKSPGSAPVTLIYDNTNRPSDIPSRFS GSGSGSTGTLTITGVRAEDEAVYYCGGYDGSTDVFGAGTTLTVL (SEQ ID NO: 31) |
|---|---|
| AB1 VH | AVTLDESEGGLQTPGGALSLVCKASGFTFSSFNMFWVRQAPGKGLEYVAFISGGGGS TWYAPAVKGRATISRDNGQSTVRLQLNNLRAEDTGTYYCAKSADTWSYGAATIDA WGHGTEVIVSS (SEQ ID NO: 32) |

FIG. 29

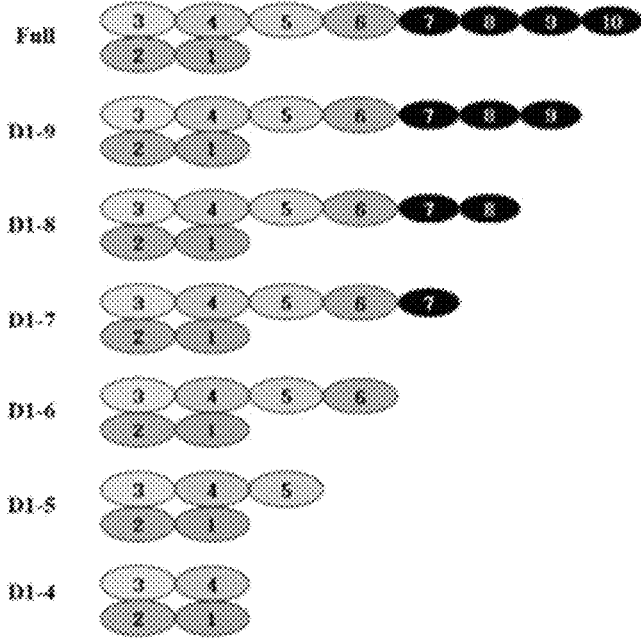

Domain 8 (fibronectin 2 domain) sequence

TPANVSGGGGSKSELVITWETVPEELQNGRGFGYVVAFRPYGKMIWMLTVLASADASRYVFRNESV
HPFSPFEVKVGVFNNKGEGPFSPTTVVYSAEE (SEQ ID NO: 33)

TARGET FOR ANTI-CANCER AND IMMUNE-ENHANCING

CROSS-REFERENCE TO THE RELATED APPLICATION

This application is a Continuation-in-Part of U.S. application Ser. No. 16/375,377 filed Apr. 4, 2019, which claims priority from U.S. Application No. 62/652,948 filed Apr. 5, 2018, the disclosures of which are incorporated herein by reference in their respective entireties.

TECHNICAL FIELD

The present disclosure provides a pharmaceutical composition for treating or preventing cancer, comprising one or more inhibitors of KIRREL3, CNTN4 and CD351, and a method of treating or preventing cancer by administering one or more inhibitors of KIRREL3, CNTN4 and CD351 to a subject in need thereof. In addition, the present disclosure provides a pharmaceutical composition for immune-enhancing, comprising one or more inhibitors of KIRREL3, CNTN4 and CD351, and a method of immune-enhancing by administering one or more inhibitors of KIRREL3, CNTN4 and CD351 to a subject in need thereof. Furthermore, the present disclosure provides a method of screening of anti-cancer agent using one or more of KIRREL3, CNTN4 and CD351, and a method of providing information necessary for analysis of cancer prognosis using one or more of KIRREL3, CNTN4 and CD351.

BACKGROUND ART

Despite advances in understanding the etiology of cancer and the methods for treating cancer over the past several years, it is still the leading cause of death worldwide. Although anti-cancer treatments exist for many malignancies, such treatments often do not fully control such malignancies or are not effective in all patients. Most of the methods currently being used to treat cancer are relatively non-selective. The affected tissue is removed through surgery, the size of solid tumors is reduced through radiation therapy, or chemotherapy is used to kill cancer cells rapidly. In particular, the chemotherapy can cause the drug resistance, and sometimes restricts the administrable dose. It causes severe side effects so that they may rule out the use of potentially effective agents. Accordingly, there is a need to develop more target-specific and effective cancer therapies.

The adaptive immune system of the human is a very precise system which is able to specifically remove cancer cells. In particular, T cells determine cell mediated adaptive immunity, and recognize and remove non-self antigens or abnormal antigens that a cell is exposed to. T cells express about 20,000 to 40,000 TCR molecules per cell, and recognize several antigens (determined by their peptide sequences) among the 100,000 pMHC molecules of APC to begin signal transfer. Such TCR molecules should function as highly sensitive sensors which need to recognize very minute changes in the antigen and transfer signals. This cell-mediated adaptive immunity operates in a very precise manner to effectively remove cancer cells. If an antigen-specific adaptive immune system does not operate normally, serious problems are caused in the ability to remove cancer cells. For example, if the protein PD-L1 or PD-L2 on the surface of a cancer cell binds to the protein PD-1 on the surface of a T cell, the T cell is not able to attack cancer cells.

Therefore, for effective cancer treatment, it is necessary to remove the factors that hinder T cell's ability to remove cancer cells.

Accordingly, the inventors have conducted research to develop a method of cancer treatment using the human immune system, and identified that inhibition of the activity and expression of one or more of KIRREL3, CNTN4 and CD351 leads to substantial suppression of development, growth, invasion and metastasis of cancer.

Technical Problem

One purpose of the present disclosure is to provide a pharmaceutical composition for treating or preventing cancer, and a method of treating or preventing cancer.

Another purpose of the present disclosure is to provide a pharmaceutical composition for immune-enhancing, and a method of immune-enhancing.

Another purpose of the present disclosure is to provide a method of screening of anti-cancer agent.

Another purpose of the present disclosure is to provide a method of providing information necessary for analysis of cancer prognosis.

Technical Solution

To achieve the purposes of the present disclosure, one aspect of the present disclosure provides a pharmaceutical composition for treating or preventing cancer comprising one or more inhibitors of KIRREL3, CNTN4 and CD351 as an active ingredient, and a method of treating or preventing cancer by administering one or more inhibitors of KIRREL3, CNTN4 and CD351 to a subject in need thereof.

The term "KIRREL3 (Kin of IRRE-like protein 3)" refers to a protein that is encoded by KIRREL3 gene, which belongs to the member of the nephrin-like protein family, and is also known as 'NEPH2'. It is expressed in fetal and adult brain, and in podocytes of kidney glomeruli, and is reported to be involved in blood filtration function of the kidney and synapse formation.

The term "CNTN4 (Contactin-4)" refers to a protein that is encoded by CNTN4 gene, which belongs to the immunoglobulin superfamily. It is reported to be a glycosylphosphatidylinositol (GPI)-anchored neuronal membrane protein that functions as a cell adhesion molecule, and to be involved in formation of axon connections in developing nervous system.

The term "CD351 (Cluster of Differentiation 351)" refers to a Fc receptor that binds to IgA and IgM with high affinity, and is also known as 'Fcα/μR'. It is reported that in mice, the receptor is expressed on macrophages, follicular dendritic cells, marginal zone and follicular B cells, and kidney tubular epithelial cells. It is reported that in human, it is expressed on intestinal lamina propria cells, Paneth cells, follicular dendritic cells in tonsils, activated macrophages, and some types of pre-germinal centre IgD+/CD38+B cells.

The KIRREL3, CNTN4 and CD351 may be human-derived KIRREL3, CNTN4 and CD351. More specifically, the amino acid sequence of KIRREL3 may be or comprise the sequence of NCBI Reference Sequence: NP_115920.1 disclosed in NCBI. The amino acid sequence of CNTN4 may comprise the sequence of NCBI Reference Sequence: NP_783200.1 disclosed in NCBI. The amino acid sequence of CD351 may be or comprise the sequence of NCBI Reference Sequence: AAL51154.1 disclosed in NCBI. In addition, each of the amino acid sequence of KIRREL3, CNTN4 and CD351 may be or comprise, but is not limited to, amino acid sequences having at least 80%, 85%, 90% or 95% identity with each sequence of NCBI Reference Sequence: NP_115920.1, NP_783200.1, AAL51154.1, as well as amino acid sequences having the property or function of KIRREL3, CNTN4 and CD351.

The gene of KIRREL3 may be or comprise a nucleic acid sequence encoding the amino acid sequence of human-derived KIRREL3, or the nucleic acid sequence of NCBI Reference Sequence: NM_032531.4 disclosed in NCBI. The gene of CNTN4 may be or comprise a nucleic acid sequence encoding the amino acid sequence of human-derived CNTN4, or the nucleic acid sequence of NCBI Reference Sequence: NM_175607.3 disclosed in NCBI. The gene of CD351 may be or comprise a nucleic acid sequence encoding the amino acid sequence of human-derived CD351, or the nucleic acid sequence of NCBI Reference Sequence: AY063125.1 disclosed in NCBI. In addition, each of the nucleic acid sequence of KIRREL3, CNTN4 and CD351 may be or comprise, but are not limited to, nucleic acid sequences having at least 80%, 85%, 90% or 95% identity with each sequence of NCBI Reference Sequence: NM_032531.4, NM_175607.3, AY063125.1, as well as nucleic acid sequences that can produce amino acids having the property or function of KIRREL3, CNTN4 and CD351.

The term "one or more inhibitors of KIRREL3, CNTN4 and CD351" refers to substances that inhibit the activity or expression of at least one selected among KIRREL3, CNTN4 and CD351. "One or more inhibitors of KIRREL3, CNTN4 and CD351" and "inhibitors of KIRREL3, CNTN4 and/or CD351" are used interchangeably. For example, the inhibitors may be a substance that inhibits the activity or expression of all of KIRREL3, CNTN4, and CD351. As another example, the inhibitors may be a substance that inhibits the activity or expression of KIRREL3 and CNTN4, or of KIRREL3 and CD351, or of CNTN4 and CD351. As another example, the inhibitors may be a substance that inhibits the activity or expression of KIRREL3, or of CNTN4, or of CD351. As another example, the inhibitors may be a combination of KIRREL3 inhibitor, CNTN4 inhibitor and CD351 inhibitor. As another example, the inhibitors may be a combination of KIRREL3 inhibitor and CNTN4 inhibitor, or a combination of KIRREL3 inhibitor and CD351 inhibitor, or a combination of CNTN4 inhibitor and CD351 inhibitor.

The inhibitors of KIRREL3, CNTN4 and/or CD351 can preferably suppress the function of cancer cells evading T cells. The inhibitors of KIRREL3, CNTN4 and/or CD351 block the activity of KIRREL3, CNTN4 and/or CD351 existing in a cancer cell, thereby suppressing the mechanism that T cells are rendered unable to attack cancer cells by KIRREL3, CNTN4 and/or CD351 and maintaining the immune activity of T cells against cancer cells. Alternatively, the inhibitors of KIRREL3, CNTN4 and/or CD351 specifically bind to KIRREL3, CNTN4 and/or CD351 protein, and interfere with binding of KIRREL3, CNTN4 and/or CD351 to T cells. Alternatively, the inhibitors of KIRREL3, CNTN4 and/or CD351 suppress a particular metabolic pathway of KIRREL3, CNTN4 and/or CD351 to reduce the expression of protein, or cause KIRREL3, CNTN4 and/or CD351 to denature so that the protein loses its activity. Therefore, the inhibitors of KIRREL3, CNTN4 and/or CD351 according to the present disclosure are very effective in treating or preventing cancer.

The inhibitors of KIRREL3, CNTN4 and/or CD351 may include, but are not limited to, any compounds, proteins, fusion proteins, antibodies, amino acids, peptides, viruses, carbohydrates, lipids, nucleic acids, extracts or fractions so long as it inhibits the activity or expression of KIRREL3, CNTN4 and/or CD351. The KIRREL3 inhibitor, CNTN4 inhibitor and CD351 inhibitor may be the same or different type independently of each other. For example, all inhibitors may be antibodies. As another example, two inhibitors may be antibodies, and one inhibitor may be a compound.

In one embodiment, the inhibitors of KIRREL3, CNTN4 and/or CD351 are ones that reduce the expression of KIRREL3, CNTN4 and/or CD351 in a cancer cell compared to a cancer cell not treated with inhibitors of KIRREL3, CNTN4 and CD351. Reduction in expression of KIRREL3, CNTN4 and/or CD351 may refer to lowered or no level of mRNA and/or protein produced from KIRREL3, CNTN4 and/or CD351 gene. The inhibitors of KIRREL3, CNTN4 and/or CD351 may include, but are not limited to, antisense nucleic acid, siRNA, shRNA, miRNA, ribozyme, etc. which binds in a complementary manner to DNA or mRNA of KIRREL3, CNTN4 and/or CD351 gene. The KIRREL3 inhibitor, CNTN4 inhibitor and CD351 inhibitor may be the same or different type independently of each other. For example, all inhibitors may be siRNAs. As another example, two inhibitors may be siRNAs, and one inhibitor may be an antisense nucleic acid.

The term "antisense nucleic acid" refers to DNAs or RNAs comprising nucleic acid sequences complementary to the sequence of certain mRNA, or fragments or derivatives thereof, which bind to or hybridize with the complementary sequences in mRNA and inhibit the translation of mRNA into protein.

The term "siRNA (small interfering RNA)" refers to a short double chain RNA which is able to induce the RNAi (RNA interference) through cleavage of certain mRNA. The siRNA comprises a sense RNA strand having a sequence homologous to the mRNA of the target gene, and an antisense RNA strand having a sequence complementary thereto. The siRNA can inhibit the expression of the target gene, and thus can be used in gene knockdown, genetic therapy, etc.

The term "shRNA (short hairpin RNA)" is a single strand RNA, which comprises a stem portion forming a double strand portion through hydrogen bonds, and a loop portion. It is processed by a protein such as Dicer to be converted into siRNA, and performs the same function as siRNA.

The term "miRNA (micro RNA)" refers to 21 to 23 non-coding RNAs which modulate gene expression after transcription by promoting the degradation of target RNA or by suppressing its translation.

The term "ribozyme" refers to an RNA molecule that has an enzyme-like function, recognizing a particular base sequence and cutting the same. The ribozyme comprises an area that specifically binds to a complementary base sequence of a target messenger RNA strand, and an area that cleaves the target RNA.

The antisense nucleic acid, siRNA, shRNA, miRNA, ribozyme, etc. that binds complementarily to the DNA or mRNA of KIRREL3, CNTN4 and/or CD351 gene can inhibit the translation of mRNA of KIRREL3, CNTN4 and/or CD351, its translocation into the cytoplasm, its maturation, or any other activities crucial for the biological functions of KIRREL3, CNTN4 and/or CD351.

In one embodiment, the inhibitors of KIRREL3, CNTN4 and/or CD351 are ones that deactivate the function of KIRREL3, CNTN4 and/or CD351 or reduce the activity thereof in a cancer cell compared to a cancer cell not treated with inhibitors of KIRREL3, CNTN4 and CD351. The inhibitors of KIRREL3, CNTN4 and/or CD351 may include, but are not limited to, compounds, peptides, peptide mimetics, fusion proteins, antibodies, aptamers, etc. that bind specifically to KIRREL3, CNTN4 and/or CD351 protein. The KIRREL3 inhibitor, CNTN4 inhibitor and CD351 inhibitor may be the same or different type independently of each other.

The term "specific" or "specifically" refers to the ability to bind to only a target protein without affecting other proteins in the cell.

The term "antibody" may include monoclonal antibodies, polyclonal antibodies, bispecific antibodies, multispecific antibodies, chimera antibodies, humanized antibodies and human antibodies, and may also include new antibodies as well as antibodies known to the art or commercialized in the art. The antibody may include not only the forms having a full length comprising two heavy chains and two light chains but also the functional fragments of antibody molecules, so long as they specifically bind to one or more of KIRREL3, CNTN4 and CD351. The functional fragment of antibody molecule refers to a fragment having at least its antigen-binding function, and may include, but are not limited to, Fab, F(ab'), F(ab')2, Fv, etc.

The term "peptide mimetics" refers to a peptide or non-peptide which inhibits the binding domain of one or more of protein of KIRREL3, CNTN4 and CD351 that induces KIRREL3, CNTN4 and/or CD351 activities.

The term "aptamer" refers to a single strand nucleic acid (DNA, RNA or modified nucleic acid) having in itself a stable tertiary structure and being able to bind to a target molecule with high affinity and specificity.

The substance inhibiting the activity or expression of KIRREL3, CNTN4 and/or CD351 which is comprised in the pharmaceutical composition of the present disclosure can inhibit suppression of T cell function by KIRREL3, CNTN4 and/or CD351, and accordingly can increase or maintain the ability of T cells to attack and kill cancer cells. Here, the ability of T cells to attack and kill cancer cells in a group treated with inhibitors of KIRREL3, CNTN4 and/or CD351 may be increased by 5% to 200% as compared to a group not treated with inhibitors of KIRREL3, CNTN4 and/or CD351. Thus, the pharmaceutical composition of the present disclosure can be useful in the preventing or treating cancer.

The cancer that can be treated or prevented by the pharmaceutical composition of the present disclosure may include, but are not limited to, stomach cancer, lung cancer, liver cancer, colorectal cancer, colon cancer, small intestinal cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, renal cancer, sarcoma, prostate cancer, urethral cancer, bladder cancer, blood cancer, leukemia, lymphoma, fibroadenoma, etc.

The pharmaceutical composition according to the present disclosure may comprise the active ingredient alone, or may additionally comprise one or more pharmaceutically acceptable carriers, excipients, diluents, stabilizing agents, preserving agent, etc.

The Pharmaceutically acceptable carriers may include, for example, carriers for oral administration or non-oral administration. The carriers for oral administration may include, for example, lactose, starch, cellulose derivatives, magnesium stearate, stearic acid, etc. The carriers for non-oral administration may include, for example, water, suitable oils, saline, aqueous glucose, glycols, etc. The pharmaceutically acceptable stabilizing agents may include, for example, antioxidants such as sodium bisulfate, sodium sulfite or ascorbic acid. The pharmaceutically acceptable preserving agents may include, for example, benzalkonium chloride, methyl- or propyl-paraben, chlorobutanol, etc. Other pharmaceutically acceptable carriers may be those disclosed in the literature "Remington's Pharmaceutical Sciences, 19th ed., Mack Publishing Company, Easton, PA, 1995".

The pharmaceutical composition of the present disclosure may be administered to animals including human using various methods. For example, it may be administered orally or parenterally. The parenteral administration may include, but are not limited to, intravenous, intramuscular, intraarterial, intramarrow, intradural, percutaneous, subcutaneous, intraperitoneal, intranasal, intraintestinal, topical, sublingual, rectal administration, etc.

The pharmaceutical composition of the present disclosure may be prepared into formulations for oral or parenteral administration, depending on the administration route as described in the above.

The formulation for oral administration may be prepared in the form of powders, granules, tablets, pills, sugar-coated pills, capsules, liquids, gels, syrups, slurries, suspensions, etc., using methods known in the art. For example, the active ingredient of the present disclosure may be mixed with suitable excipient(s) and/or adjuvant(s), and then processed into a granule mixture to obtain a tablet or a sugar-coated tablet for oral administration. Examples of suitable excipients may include, but are not limited to, sugars including lactose, dextrose, sucrose, sorbitol, mannitol, xylitol, erythritol, maltitol, etc., starches including corn starch, wheat starch, rice starch, potato starch, etc., celluloses including cellulose, methyl cellulose, sodium carboxymethylcellulose, hydroxypropylmethylcellulose, etc., and fillers such as gelatin, polyvinyl pyrrolidone, etc. Optionally, disintegrating agents such as crosslinked polyvinyl pyrrolidone, agar, alginic acid or sodium alginate may be added. Further, the pharmaceutical composition of the present disclosure may further comprise anticoagulants, lubricants, wetting agents, aromatic agents, emulsifiers and preservatives, etc.

The formulation for parenteral administration may be prepared in the form of injections, gels, aerosols, nasal inhalers using methods known in the art.

These administration forms may refer to those disclosed in the literature known in the art "Remington's Pharmaceutical Science, 15th Edition, 1975. Mack Publishing Company, Easton, Pennsylvania 18042, Chapter 87: Blaug, Seymour".

The total effective dose of the pharmaceutical composition according to the present disclosure may be administered to a subject in a single dose, or in multiple doses through a fractionated treatment protocol.

The appropriate dose of the pharmaceutical composition according to the present disclosure or the contents of active ingredient in the pharmaceutical composition may be determined considering various factors such as administration route, times administered, patient age, body weight, health, gender, severity of disease, diet and excretion rate, etc. by a person having ordinary skill in the art. For example, the total dose of the pharmaceutical composition according to the present disclosure may be about 0.01 μg to 1,000 mg per 1 kg body weight of a patient per day, or 0.1 μg to 100 mg. There is no particular limit to the dosage form, administration route and administration method, so long as the pharmaceutical composition shows the effect of the invention.

Another aspect of the present disclosure provides a pharmaceutical composition for immune-enhancing in a subject, comprising one or more inhibitors of KIRREL3, CNTN4 and CD351 as an active ingredient.

When the pharmaceutical composition is administered to a subject in need thereof, it can fully or partially reduce the expression or activity of one or more of KIRREL3, CNTN4 and CD351 in the subject to increase the level of T cell-mediated immune response.

Accordingly, the pharmaceutical composition of the present disclosure can be used for immune-enhancing. For example, it can be used for the subject in need of prevention, treatment or improvement of diseases related to immunodeficiency, lower immune function, immune system damage, immunocompromising, etc.

Another aspect of the present disclosure is to provide a method of treating or preventing cancer in a subject, comprising administering to the subject one or more inhibitors of KIRREL3, CNTN4 and CD351. And also, another aspect of the present disclosure provides a method of immune-enhancing in a subject, comprising administering to the subject one or more inhibitors of KIRREL3, CNTN4 and CD351. In these methods, unless specifically mentioned otherwise, the terms associated have the same meaning as the terms explained for the pharmaceutical compositions in the above.

Another aspect of the present disclosure is to provide a method of screening an anti-cancer agent comprising:

(a) treating a cancer cell with a candidate of anti-cancer agent; and (b) measuring the expression or activity of one or more of KIRREL3, CNTN4 and CD351 in the cancer cell.

Optionally, the method of screening an anti-cancer agent may further comprise a step of determining the candidate anti-cancer agent to be the anti-cancer agent if a group treated with the candidate anti-cancer agent shows a lower (or significantly lower) level of expression of one or more of KIRREL3, CNTN4 and CD351 mRNA or protein or a lower (or significantly lower) level of suppression of T cell activity by one or more of KIRREL3, CNTN4 and CD351 compared to a group not treated with the candidate anti-cancer agent. Here, the lower (or significantly lower) level may indicate an amount decreased by 5% to 95% (e.g., 10%, 15%, 20%, 25%, 30%, 35%, 40%, 45%, 50%, 55%, 60%, 65%, 70%, 75%, 80%, 85% and 90%). The decreased amounts may also mean the sum of each decreased amount of KIRREL3, CNTN4 and CD351, or the independently decreased amounts of KIRREL3, CNTN4, and CD351. The group not treated with the candidate anti-cancer agent may be cancer cells to which no substance is added, or to which any substance such as anti-cancer agent other than one or more inhibitors of KIRREL3, CNTN4 and CD351 is treated.

The term "screening" refers to finding the target materials having the particular properties such as sensitivity or activity among proteins, fusion proteins, antibodies, peptides, antibiotics, enzymes, compounds or any other substances.

The term "candidate anti-cancer agent" may refer to a nucleic acid, protein, antibody, compound, extract or natural substance that is randomly selected or is thought to be able to inhibit the expression or activity of KIRREL3, CNTN4 and/or CD351 according to the usual selection method. The candidate of anti-cancer agent may preferably be a substance that inhibits the expression and/or activity of KIRREL3, CNTN4 and/or CD351.

The expression or activity of KIRREL3, CNTN4 and/or CD351 may be measured by determining the level of expression of the mRNA or protein of KIRREL3, CNTN4 and/or CD351, or by determining the degree to which T cell activity is suppressed by KIRREL3, CNTN4 and/or CD351.

The method of determining the level of expression of the mRNA of KIRREL3, CNTN4 and/or CD351 may include, but are not limited to, any method conventionally known to the art such as reverse transcriptase PCR, competitive reverse transcriptase PCR, real-time reverse transcriptase PCR, RNase protection assay, Northern blotting, DNA chip or RNA chip.

The method of determining the level of expression of KIRREL3, CNTN4 and/or CD351 protein may include, but are not limited to, any method conventionally known to the art such as Western blot, ELISA, radioimmunoassay analysis, radial immunodiffusion, Ouchterlony immunodiffusion, rocket immunoelectrophoresis, tissue immunohistochemistry, immunoprecipitation assay, complement fixation assay, FACS or protein chip.

The method of determining the degree of T cell activity inhibition by KIRREL3, CNTN4 and/or CD351 may include, but are not limited to, any method conventionally known to the art such as RT-PCR, Western Blot, ELISA, radioimmunoassay, radioimmunodiffusion, Ouchterlony immunodiffusion, rocket immunoelectrophoresis, immunohistochemistry, immunoprecipitation, complete fixation assay, or FACS.

In addition, in the method of screening of the present disclosure, confirmation of KIRREL3, CNTN4 and/or CD351 activity inhibition may be performed using conventional methods such as reacting KIRREL3, CNTN4 and/or CD351 protein and a candidate substance to measure an activity, yeast two-hybrid, searching for phage-displayed peptide clones binding to KIRREL3, CNTN4 and/or CD351 protein, HTS (high throughput screening) using natural material and chemical libraries, drug hit HTS, cell-based screening, or DNA array-based screening.

The method of screening an anti-cancer agent may be performed either in vitro or in vivo. For in vivo, the step of treating a cancer cell with a candidate of anti-cancer agent may be substituted by a step of administering a candidate of anti-cancer agent to a subject having cancer cells or suffering from cancer. Such a subject may be am animal such as human, mouse, etc.

The method of screening an anti-cancer agent is based on the novel disclosure in the present invention that inhibition of the activity or expression of KIRREL3, CNTN4 and/or CD351 can suppress the function of cancer cells evading T cells. The method of screening of the present disclosure is very advantageous in that it allows for easy development of new anti-cancer agents through a simple and inexpensive method.

Another aspect of the present disclosure provides a method of providing information necessary for analysis of cancer prognosis, comprising measuring expression or activity of one or more of KIRREL3, CNTN4 and CD351 in cells or tissues isolated from a subject.

In the method, the terms associated with the expression or activity of one or more of KIRREL3, CNTN4 and CD351 and its measurement, unless specifically mentioned otherwise, have the same meaning as the terms explained for the composition and the screening method.

The term "prognosis" refers to predictions as to progress of disease, improvement of disease, recurrence of disease, metastasis, and likelihood of death. For example, in the present disclosure, the prognosis refers to the possibility of curing a cancer patient or improving the condition of cancer patient.

The cell or tissue isolated from the subject may be a cancer cell or a tissue wherein cancer have occurred or cancer cells exist.

The method of providing information necessary for analysis of cancer prognosis is based on the fact that the lower activity or expression of one or more of KIRREL3, CNTN4 and CD351 in cancer cells can increase T cell activity and proliferation, thereby increasing cancer treatment effect.

Another aspect of the present disclosure provides a pharmaceutical composition comprising an anti-CNTN4 antibody or antigen-binding fragment thereof, which specifically binds to CNTN4. Specifically, the pharmaceutical composition may comprise the anti-CNTN4 antibody or antigen-binding fragment thereof binding to Fibronectin 2 (FN2) domain of CNTN4, when bound to CNTN4. Further, the pharmaceutical composition may be used for anti-cancer.

The anti-CNTN4 antibody or antigen-binding fragment thereof binds to Fibronectin 2 (FN2) domain of CNTN4, when bound to CNTN4. The FN2 domain may comprise the amino acid sequences listed in SEQ ID NO: 33.

CNTN4 consists of a total of ten (10) domains, i.e., Ig1 to Ig6 and FN1 to FN4 and binds to amyloid precursor protein (APP) in body. Specifically, FN1 to FN2 domain (domain 7 to domain 8) of CNTN4 strongly binds to Kunitz-type protease inhibitor (KPI) domain of APP (Ig; Ig like domain, FN; fibronection). FN1 to FN2 domain (domain 7 to domain 8) of CNTN4 consists of amino acid sequences listed in SEQ ID NO: 29 and KPI domain of APP consists of amino acid sequences listed in SEQ ID NO: 30.

When the anti-CNTN4 antibody or antigen-binding fragment thereof binds to CNTN4, it blocks binding of CNTN4 to APP. As such, the anti-CNTN4 antibody or antigen-binding fragment thereof would be useful to inhibit the interaction between CNTN4 and APP.

The articles "a" and "an" are used herein to refer to one or to more than one (i.e. to at least one) of the grammatical object of the article. By way of example, "an ingredient" means one ingredient or more than one ingredient. The term "A, B and/or C" is used herein to refer to A, or B, or C, or A and B, or A and C, or B and C, or A, B and C.

BRIEF DESCRIPTION OF FIGURES

Figures 13A, 13B:
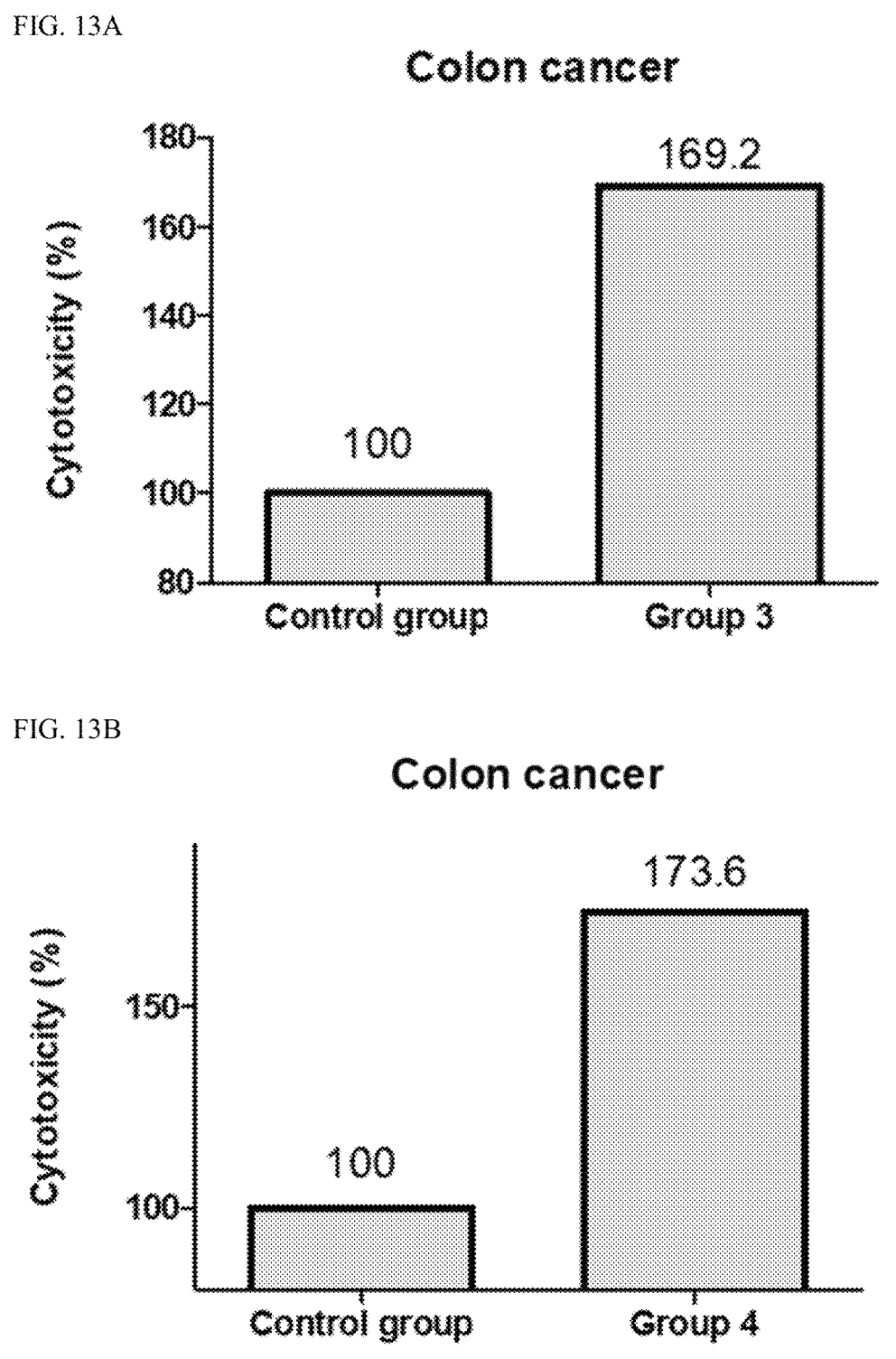

FIGS. 13A, 13B, 13C and 13D show the cytotoxicity (%) of PBMC when colon cancer cell line HCT-116 and PBMC were treated with CNTN4 inhibitors.

FIGS. 15A, 15B, 15C and 15D show the cytotoxicity (%) of PBMC when gastric cancer cell line MKN-74 and PBMC were treated with CNTN4 inhibitors.

FIGS. 16A, 16B, 16C and 16D show the cytotoxicity (%) of PBMC when leukemia cell line U937 and PBMC were treated with CNTN4 inhibitors.

Figures 17A, 17B:
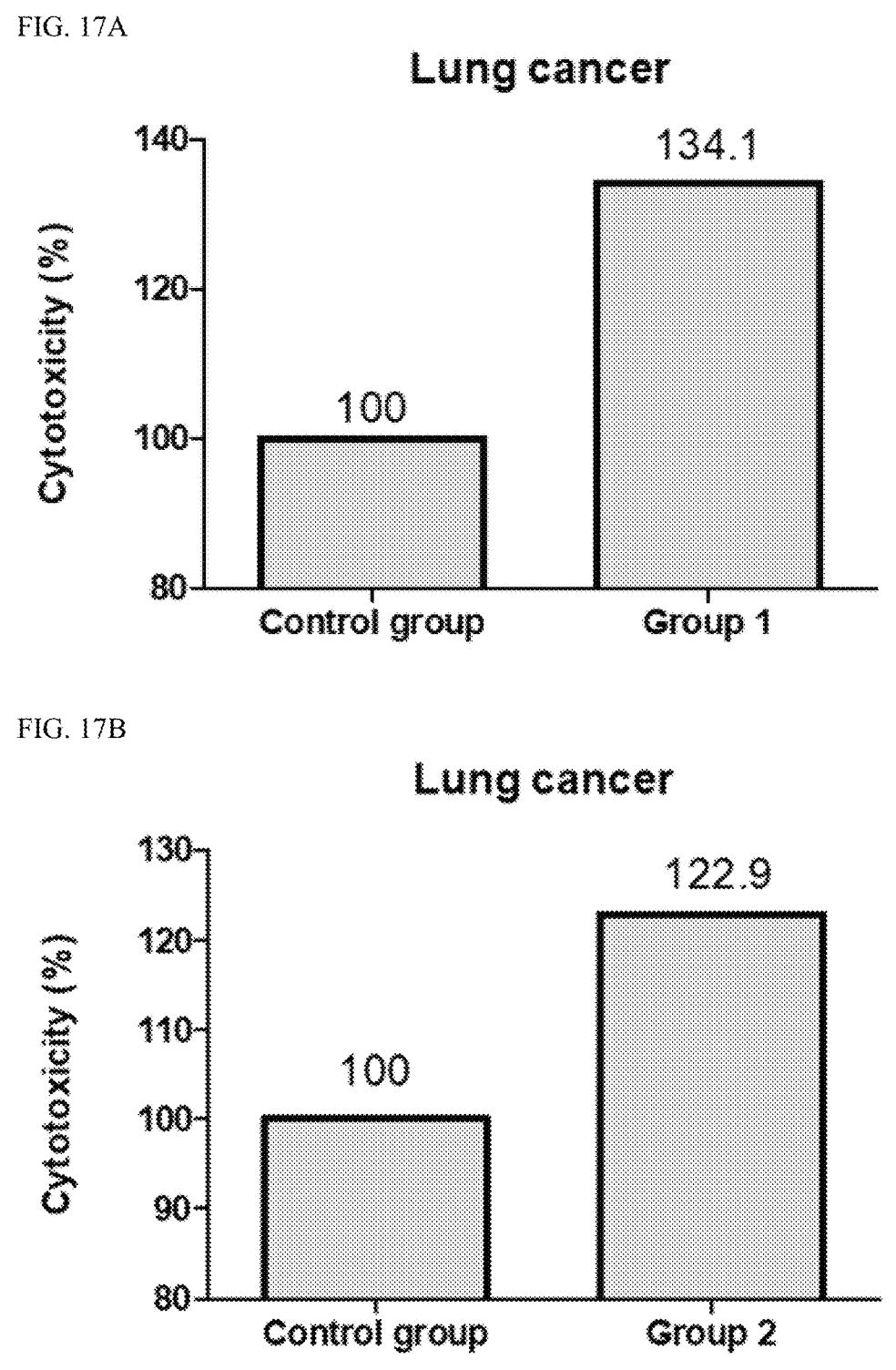

FIGS. 17A, 17B, 17C and 17D show the cytotoxicity (%) of PBMC when lung cancer cell line A549 and PBMC were treated with CD351 inhibitors.

Figures 18C, 18D:
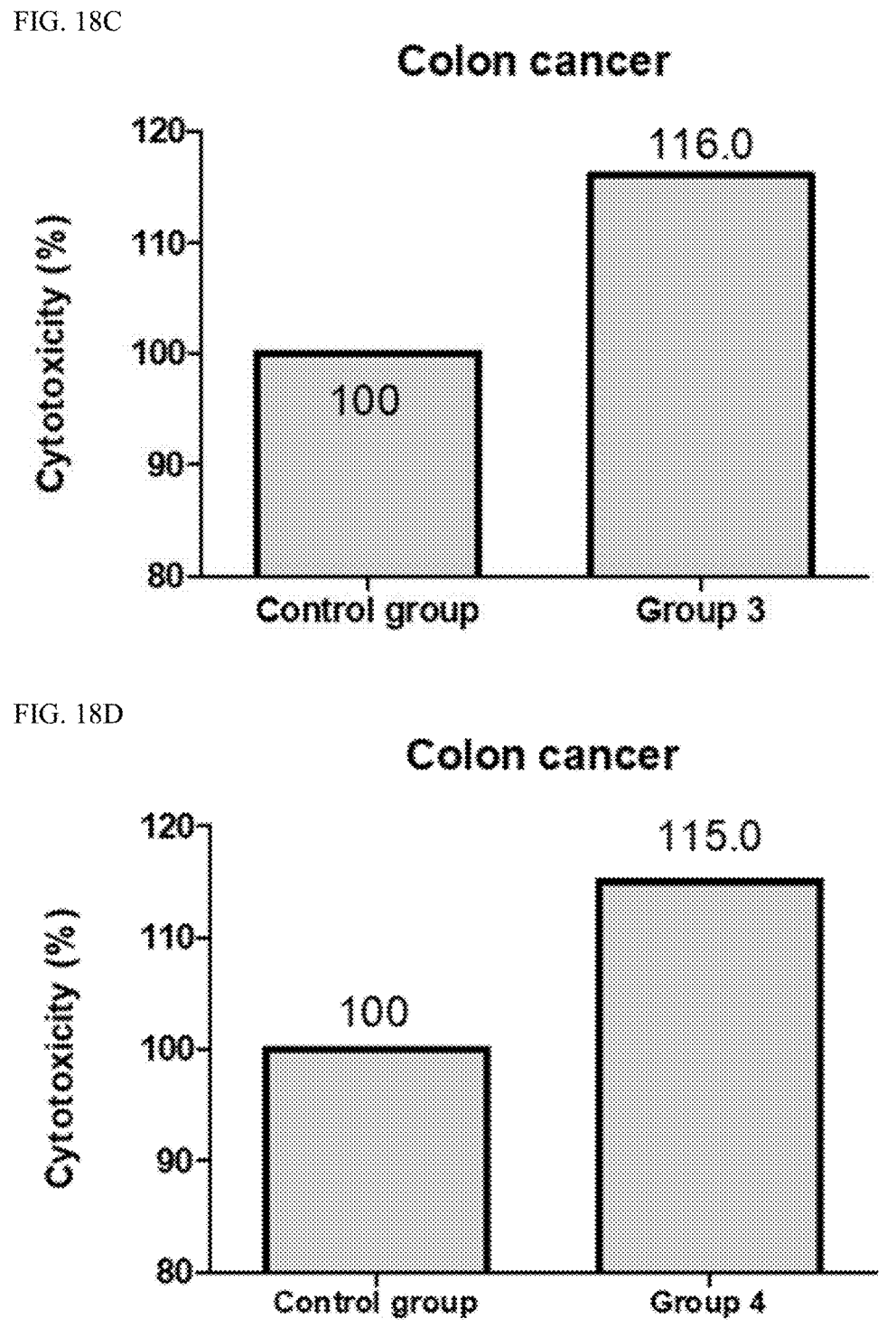

FIGS. 18A, 18B, 18C and 18D show the cytotoxicity (%) of PBMC when colon cancer cell line HCT-116 and PBMC were treated with CD351 inhibitors.

FIGS. 19A, 19B, 19C and 19D show the cytotoxicity (%) of PBMC when breast cancer cell line MDA-MB-231 and PBMC were treated with CD351 inhibitors.

Figures 20C, 20D:
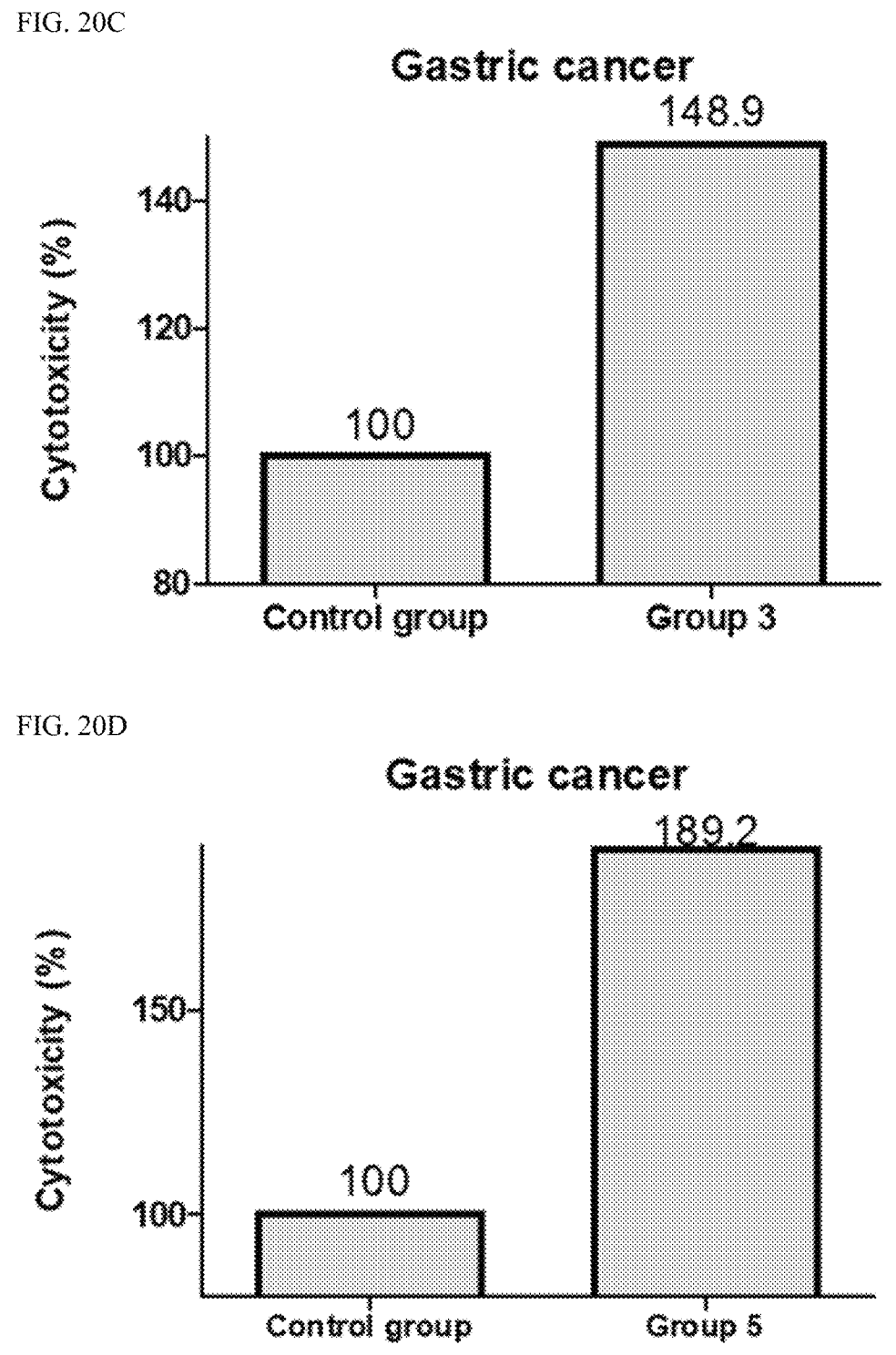

FIGS. 20A, 20B, 20C and 20D show the cytotoxicity (%) of PBMC when gastric cancer cell line MKN-74 and PBMC were treated with CD351 inhibitors.

FIGS. 24A, 24B and 24C show the tumor size in mouse treated with CD351 inhibitors.

FIG. 25A shows four deletion structures of CNTN4 (#10: full length), and FIG. 25B shows three isoform structures of APP (APP 770: full length).

FIG. 27 shows the amino acid sequences of FN1-FN2 domain of CNTN4 and KPI domain of APP.

FIG. 28 shows the amino acid sequences of light chain variable region (VL) and heavy chain variable region (VH) of anti-CNTN4 antibody AB1.

FIG. 29 is a schematic diagram of the human CNTN4 domain samples prepared in accordance with Example 5.2.1.

EXAMPLES

Figure 1:
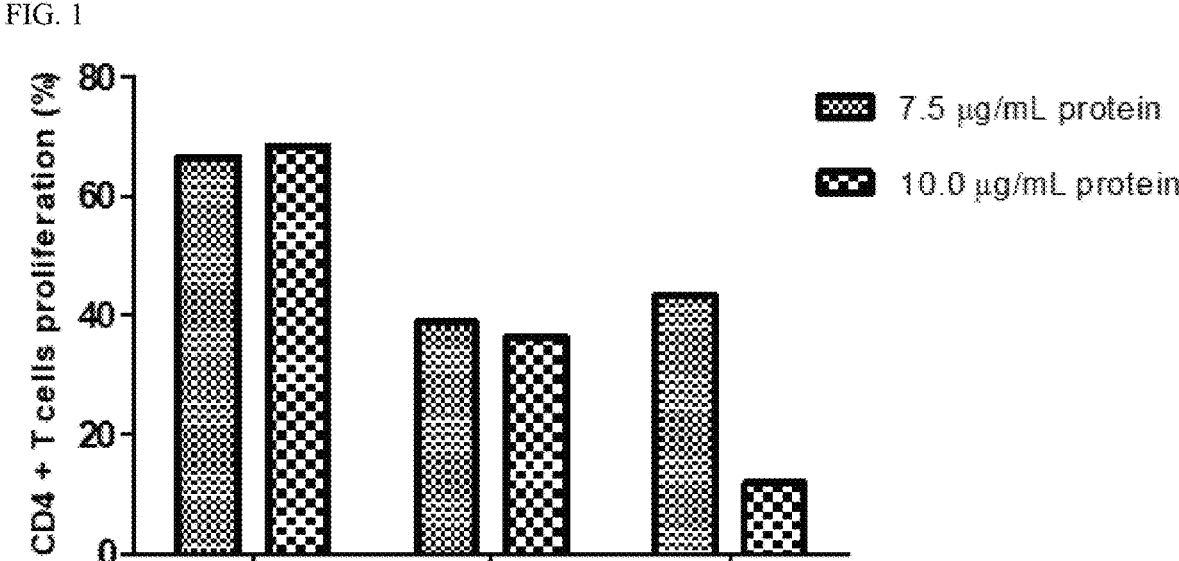
FIG. 1 shows the proliferation (%) of CD4+ T cells suppressed by KIRREL3.

In the following, exemplary embodiments of the inventive concept will be explained in further detail with reference to examples. However, the following examples are meant to exemplify the present invention, and the scope of the invention is not restricted by these examples.

Example 1. Inhibition of the proliferation and activity of T cells

This example is to confirm whether KIRREL3, CNTN4 and CD351 suppress the proliferation and activity of the T cell, and ensures that cancer cells evade the T cell-mediated immune system.

1.1. Preparation of CD4+ cells and CD8+ T cells

Human blood was placed in a 10 ml tube coated with EDTA (or heparin) and mixed with PBS at a ratio of 1:1. Ficoll-Paque PLUS was placed in a 50 ml tube, and then the blood sample was added. After centrifugation, human PBMCs (peripheral blood mononuclear cells) were collected. The resultant was centrifuged, and the supernatant was removed. Then, RBC lysis (1×) was added, pipetted, and stored on ice for 3 minutes. After that, 50 ml of 10% FBS RPMI1640 was added, and the mixture was centrifuged to remove the supernatant. Then, FACS buffer was added, and the supernatant was removed by centrifugation. Subsequently, 50 ml of MACS buffer (PBS containing 0.5% bovine serum albumin and 2 mM EDTA) was added, the number of cells was counted, and the supernatant was completely removed after centrifugation.

CD4+ T cells and CD8+ T cells were resuspended using 40 µl of MACS buffer based on the number of $1 \times 10^7$ cells in a 50 ml tube. 10 µl of anti-CD4 and anti-CD8 biotin antibodies were added to the tube respectively, and then stored in the refrigerator for 5 minutes. Subsequently, 30 µl of MACS buffer based on the number of $1 \times 10^7$ cells was added to the resultant, and 20 µl of anti-biotin microbeads were added and mixed. Then, CD4+ T cells and CD8+ T cells were separated using LS column, and were counted.

The prepared CD4+ T cells and CD8+ T cells were mixed with 1 µl of CFSE (carboxyfluorescein succinimidyl ester) based on the number of $2 \times 10^6$ cells, and stored at 37° C. for 3 minutes. Then, FBS was added into tubes containing the CD4+ T cells and CD8+ T cells respectively, and stored on ice 10 minutes. Thereafter, the supernatant was removed by centrifugation. The resultant was added with 30 ml of FACS buffer, pipetted, and centrifuged to remove the supernatant. Then, the resultant was mixed with 10 ml of 10% FBS RPMI1640, and the number of cells was counted.

1.2. Measurement of T Cell Activity 1.2.1. Inhibition of T Cell Activity by KIRREL3

The recombinant human IgG1 Fc protein (Cat. No. 110-HG) and the recombinant human PD-L1/B7-H1 Fc chimera protein (Cat. No. 156-B7) were purchased from R&D systems. The recombinant human KIRREL3 His Tag protein (Cat. No. 4910-K3) was purchased from R&D systems.

7.5 µg/ml or 10 µg/ml of each protein was mixed with 2.5 µg/ml of anti-CD3 antibody (BioLegend, Cat. No. 317325) in PBS, respectively. The resultant mixture was coated on 96-well plates at 4° C., and the wells were washed three times with PBS.

The CD4+ T cells and CD8+ T cells prepared in the Example 1.1 were added to each well of the 96-well plate at the number of $2 \times 10^6$ cells in an amount of 200 µl, and then incubated.

CD4+ T cells and CD8+ T cells were activated by anti-CD3 antibody for 72 hours. The proliferation of CD4+ T cells and CD8+ T cells can be confirmed by the degree of CFSE fluorescent cell staining, and was analyzed by flow cytometry using FACSDiVa software (BD Biosciences).

1.2.2. Inhibition of T-Cell Activity by CNTN4

The recombinant human IgG1 Fc protein (Cat. No. 110-HG) and the recombinant human PD-L1/B7-H1 Fc chimera protein (Cat. No. 156-B7) were purchased from R&D systems. The recombinant human CNTN4 His Tag protein (Cat. No. 2205-CN) was purchased from R&D systems.

7.5 µg/ml or 10 µg/ml of each protein was mixed with 2.5 µg/ml of anti-CD3 antibody (BioLegend, Cat. No. 317325) in PBS, respectively. The resultant mixture was coated on 96-well plates at 4° C., and the wells were washed three times with PBS.

The CD4+ T cells and CD8+ T cells prepared in the Example 1.1 were added to each well of the 96-well plate at the number of $2 \times 10^6$ cells in an amount of 200 µl, and then incubated.

CD4+ T cells and CD8+ T cells were activated by anti-CD3 antibody for 72 hours. The proliferation of CD4+ T cells and CD8+ T cells can be confirmed by the degree of CFSE fluorescent cell staining, and was analyzed by flow cytometry using FACSDiVa software (BD Biosciences).

1.2.3. Inhibition of T-Cell Activity by CD351

The recombinant human IgG1 Fc protein (Cat. No. 110-HG) and the recombinant human PD-L1/B7-H1 Fc chimera protein (Cat. No. 156-B7) were purchased from R&D systems. The recombinant human CD351 His Tag protein (Cat. No. 9278-FC) was purchased from R&D systems.

10 µg/ml of each protein was mixed with 1.0 µg/ml, 2.0 µg/ml, 4.0 µg/ml, or 6.0 µg/ml of anti-CD3 antibody (BioLegend, Cat. No. 317325) in PBS, respectively. The resultant mixture was coated on 96-well plates at 4° C., and the wells were washed three times with PBS.

The CD4+ T cells and CD8+ T cells prepared in the Example 1.1 were added to each well of the 96-well plate at the number of $2 \times 10^6$ cells in an amount of 200 µl, and then incubated.

CD4+ T cells and CD8+ T cells were activated by anti-CD3 antibody for 72 hours. The proliferation of CD4+ T cells and CD8+ T cells can be confirmed by the degree of CFSE fluorescent cell staining, and was analyzed by flow cytometry using FACSDiVa software (BD Biosciences).

1.3. Results 1.3.1. Inhibition of T-Cell Activity by KIRREL3

Figure 2:
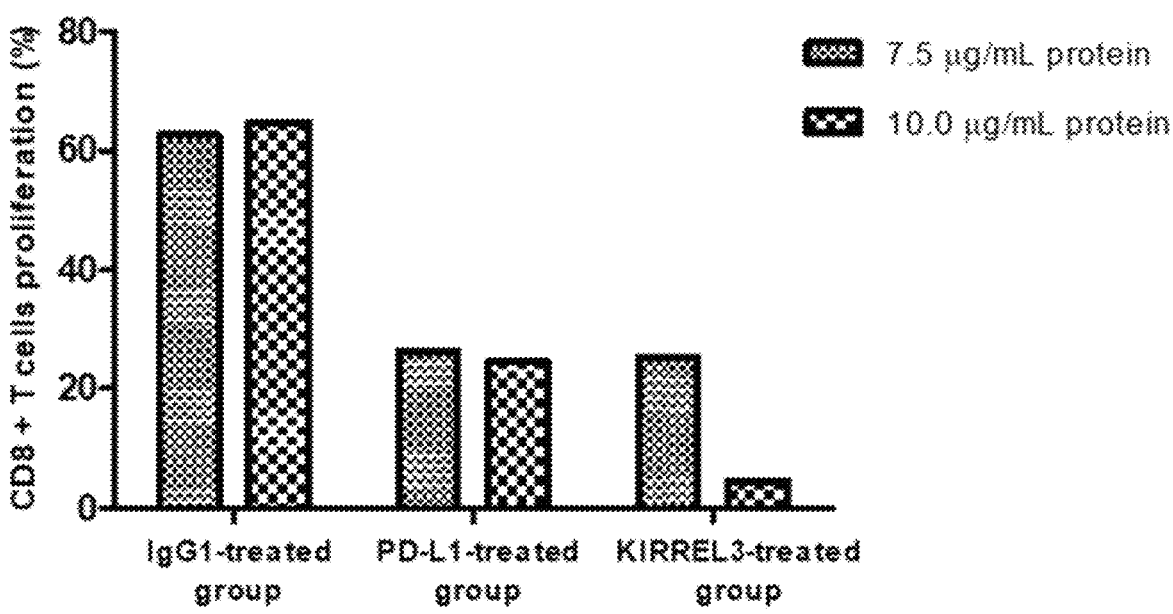
FIG. 2 shows the proliferation (%) of CD8+ T cells suppressed by KIRREL3.

FIG. 1 and FIG. 2 show the percent proliferation (%) of CD4+ T cells and CD8+ T cells, respectively.

The control group treated with PD-L1 inhibited the proliferation of both CD4+ T cells and CD8+ T cells compared to the control group treated with IgG1. The PD-L1 binds to PD-1, a protein on the surface of T cells, and inhibits the proliferation of T cells. Accordingly, it results in suppressing the function of T cells attacking and killing cancer cells.

The group treated with KIRREL3 remarkably inhibited the proliferation of both CD4+ T cells and CD8+ T cells compared to the control group treated with IgG1. And also, the group treated with KIRREL3 inhibited the proliferation of both CD4+ T cells and CD8+ T cells similarly to the control group treated with PD-L1.

It means that if KIRREL3 is neutralized by blocking or knockdown, the T cell proliferation inhibition of KIRREL3 can be suppressed. Accordingly, the cancer treatment can be effectively achieved.

1.3.2. Inhibition of T-Cell Activity by CNTN4

Figure 3:
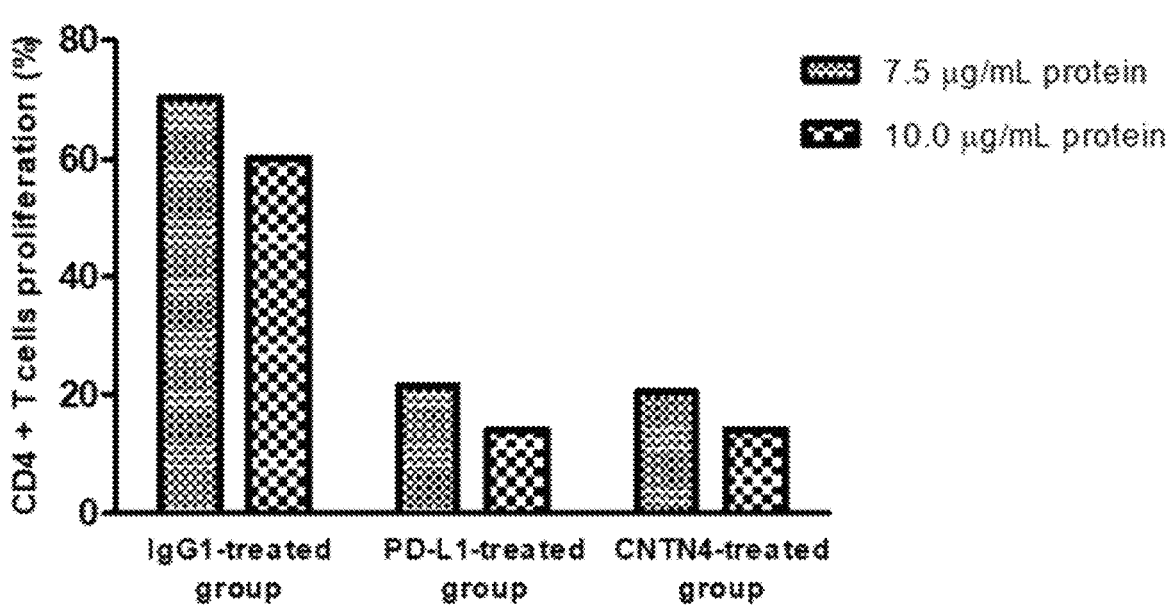
FIG. 3 shows the proliferation (%) of CD4+ T cells suppressed by CNTN4.
Figure 4:
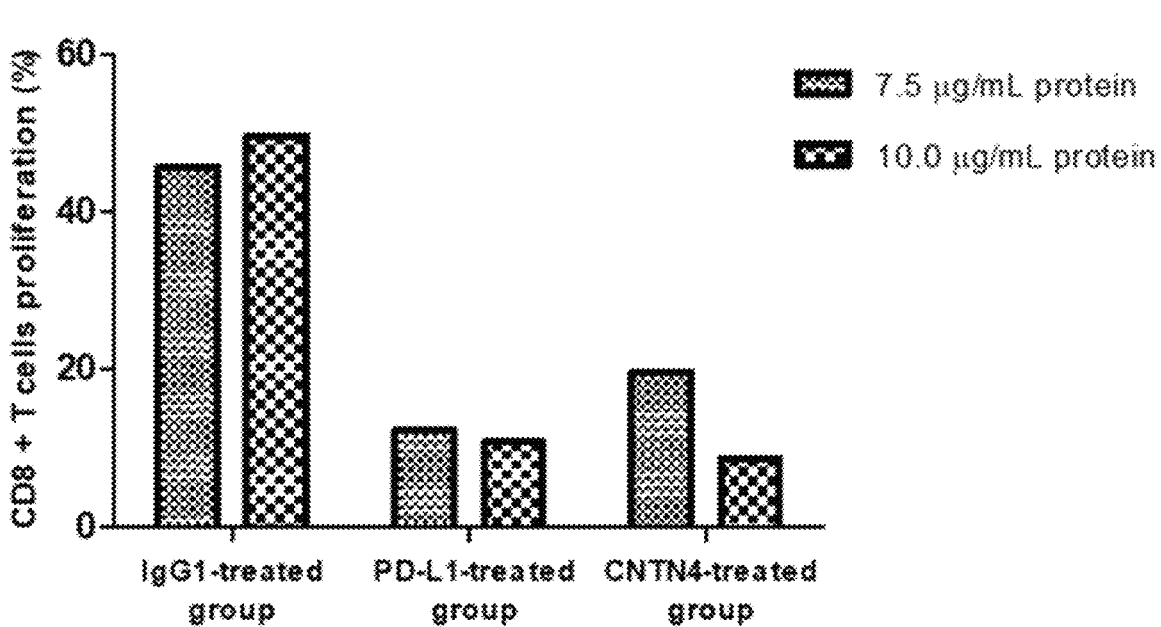
FIG. 4 shows the proliferation (%) of CD8+ T cells suppressed by CNTN4.

FIG. 3 and FIG. 4 show the percent proliferation (%) of CD4+ T cells and CD8+ T cells, respectively.

The control group treated with PD-L1 inhibited the proliferation of both CD4+ T cells and CD8+ T cells compared to the control group treated with IgG1.

The group treated with CNTN4 remarkably inhibited the proliferation of both CD4+ T cells and CD8+ T cells compared to the control group treated with IgG1. And also, the group treated with CNTN4 inhibited the proliferation of both CD4+ T cells and CD8+ T cells similarly to the control group treated with PD-L1.

It means that if CNTN4 is neutralized by blocking or knockdown, the T cell proliferation inhibition of CNTN4 can be suppressed. Accordingly, the cancer treatment can be effectively achieved.

1.3.3. Inhibition of T-Cell Activity by CD351

Figure 5:
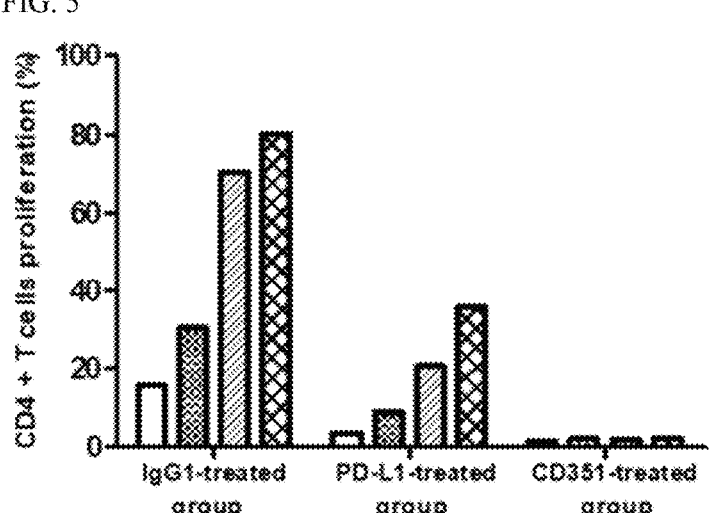
FIG. 5 shows the proliferation (%) of CD4+ T cells suppressed by CD351.
Figure 6:
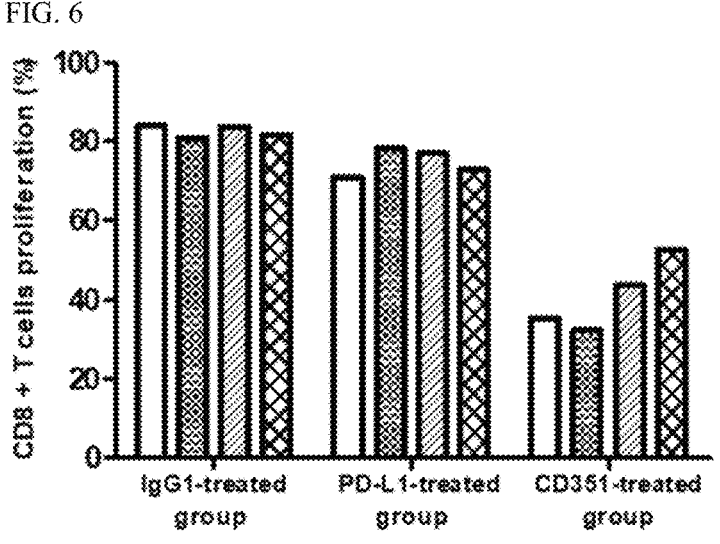
FIG. 6 shows the proliferation (%) of CD8+ T cells suppressed by CD351.
Figure 7A:
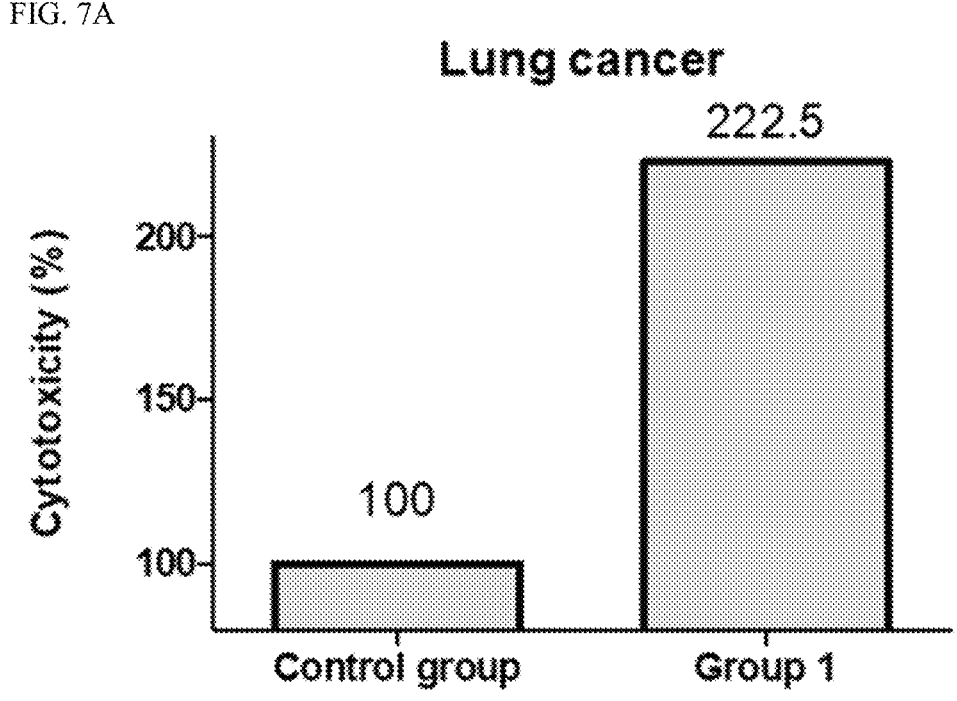
FIGS. 7A, 7B, 7C and 7D show the cytotoxicity (%) of PBMC when lung cancer cell line A549 and PBMC were treated with KIRREL3 inhibitors.
Figure 7B:
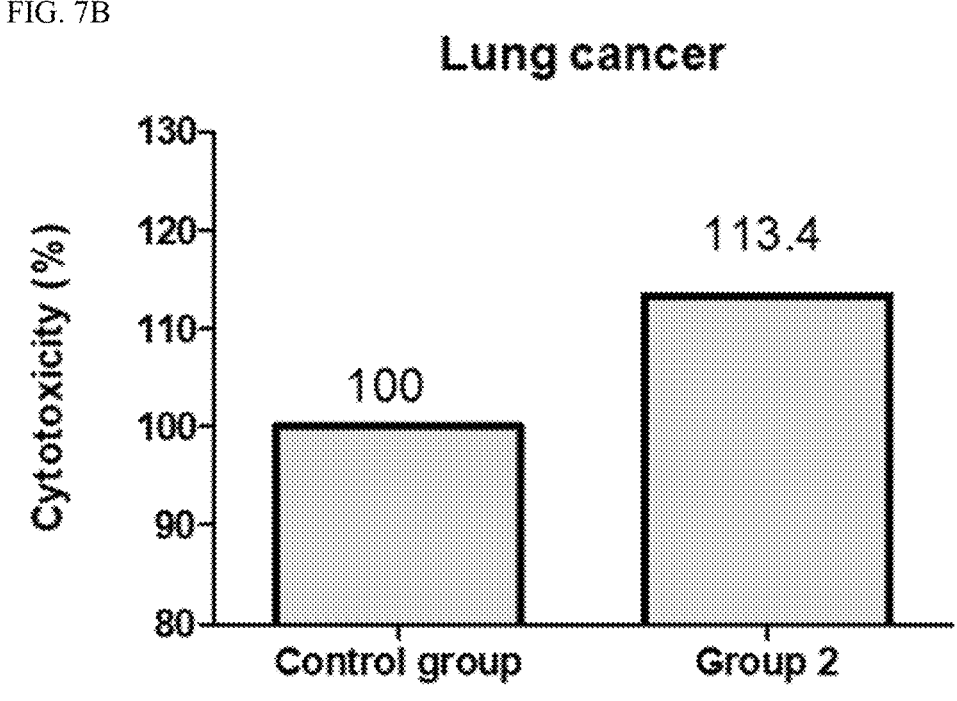
Figures 7C, 7D:
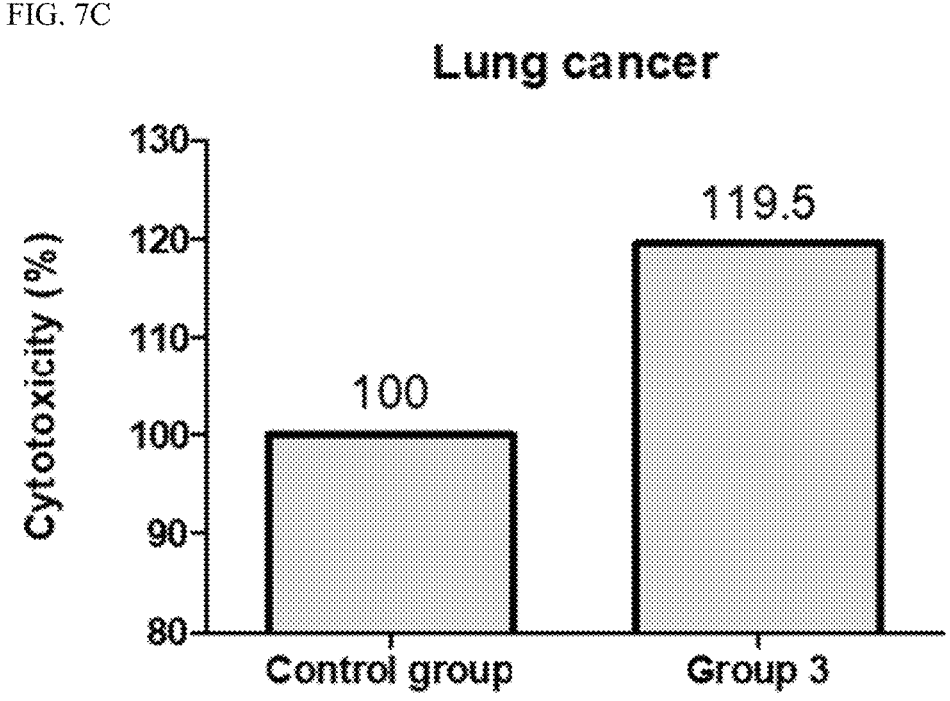
Figure 8A:
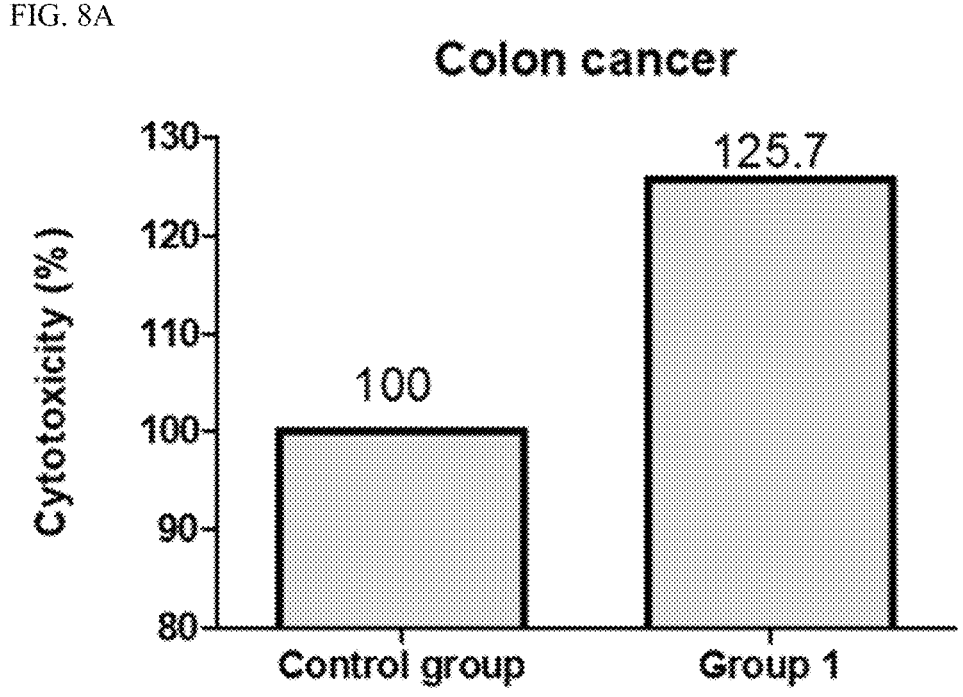
FIGS. 8A, 8B, 8C and 8D show the cytotoxicity (%) of PBMC when colon cancer cell line HCT-116 and PBMC were treated with KIRREL3 inhibitors.
Figure 8B:
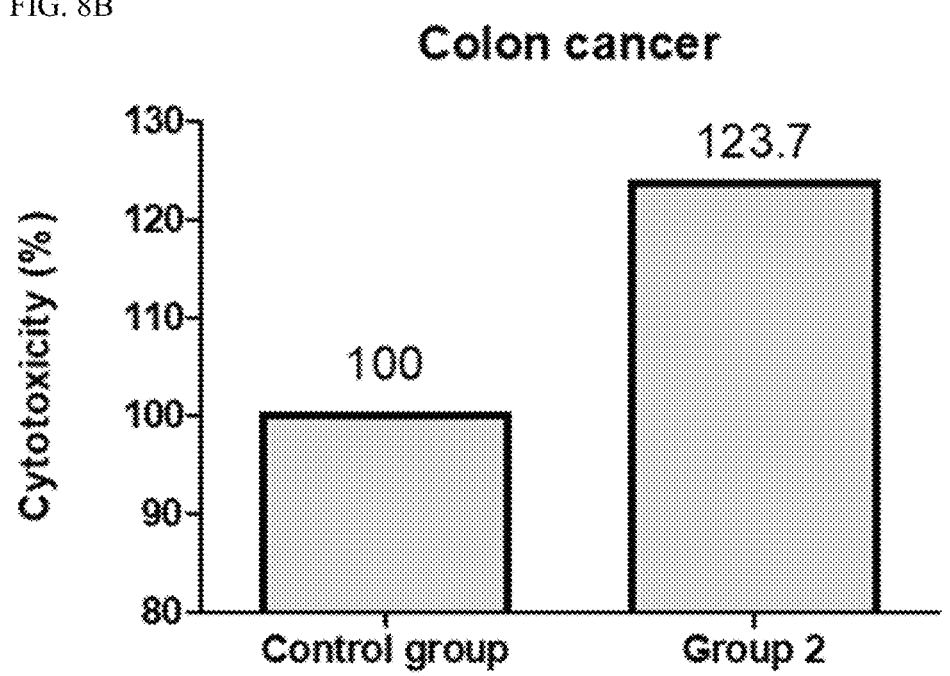
Figures 8C, 8D:
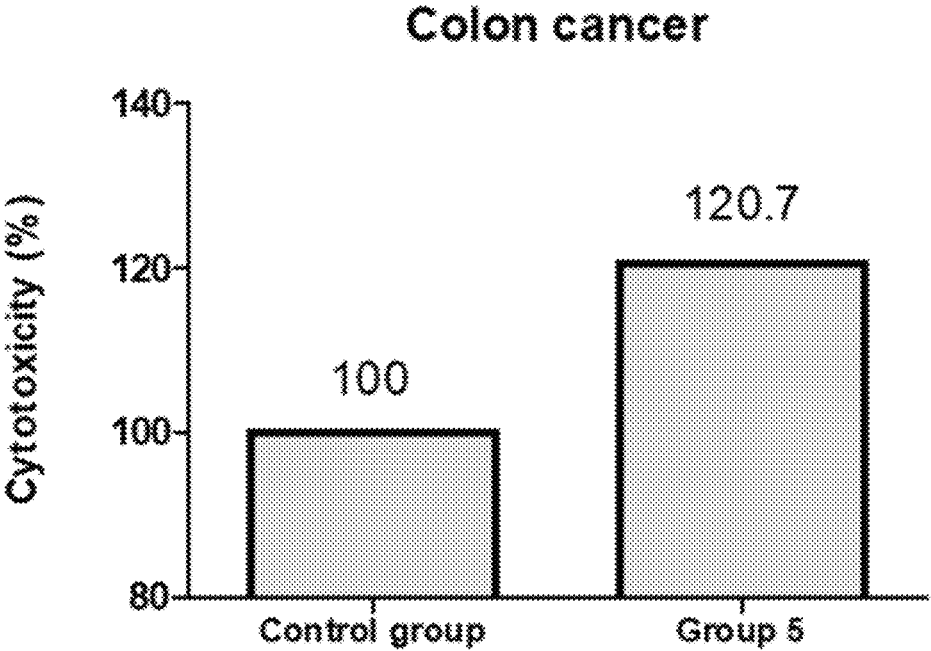
Figure 9A:
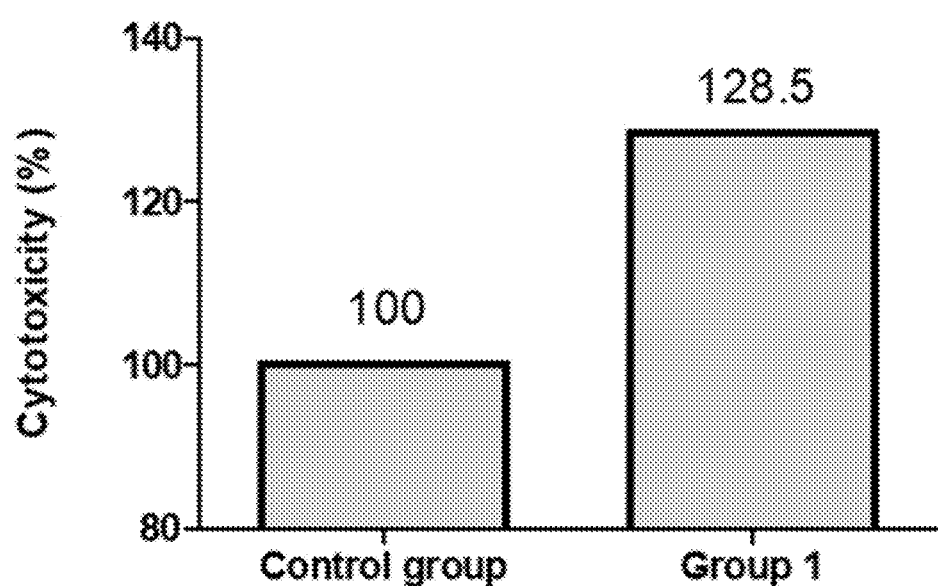
FIGS. 9A, 9B, 9C and 9D show the cytotoxicity (%) of PBMC when breast cancer cell line MDA-MB-231 and PBMC were treated with KIRREL3 inhibitors.
Figure 9B:
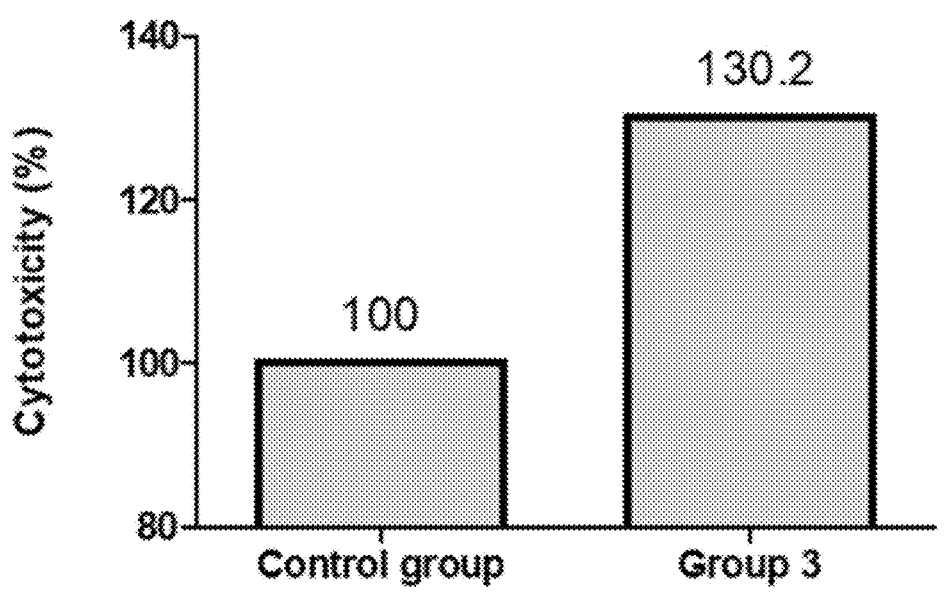
Figures 9C, 9D:
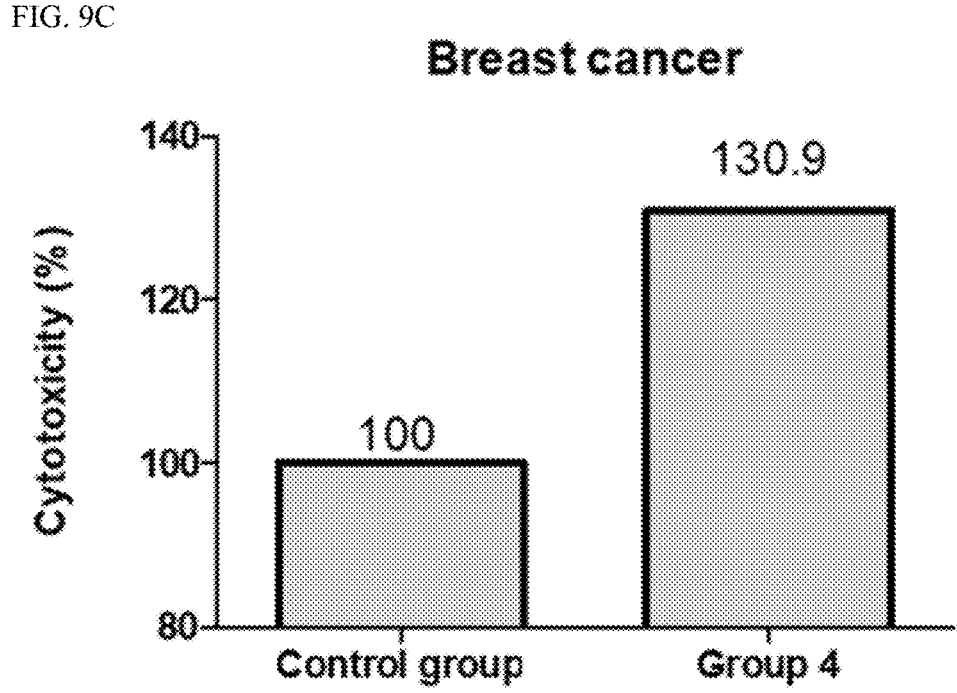
Figure 10A:
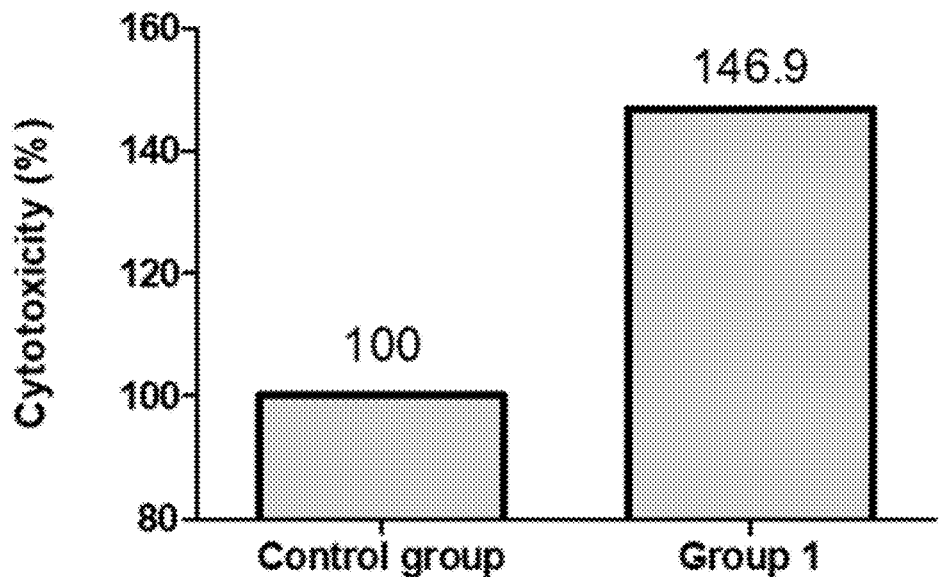
FIGS. 10A, 10B, 10C and 10D show the cytotoxicity (%) of PBMC when gastric cancer cell line MKN-74 and PBMC were treated with KIRREL3 inhibitors.
Figure 10B:
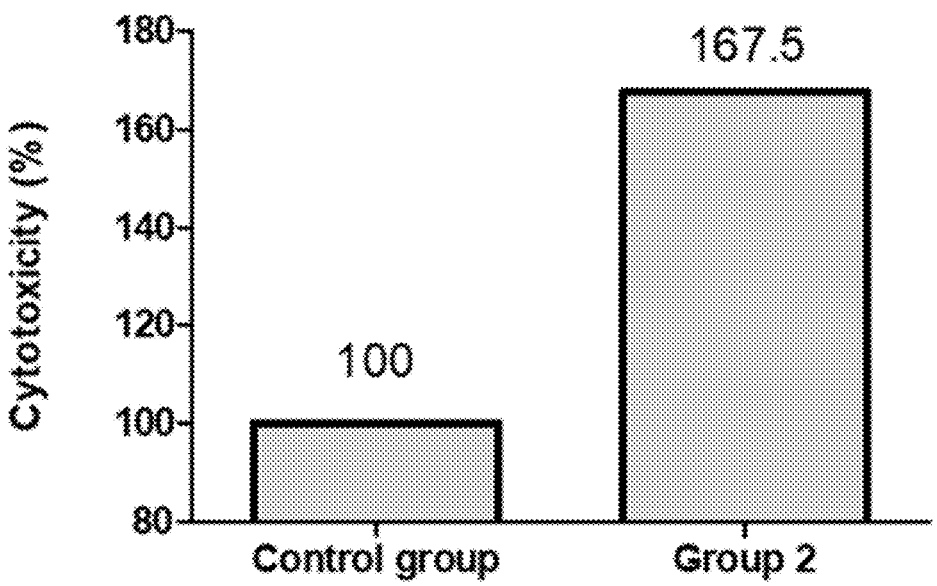
Figures 10C, 10D:
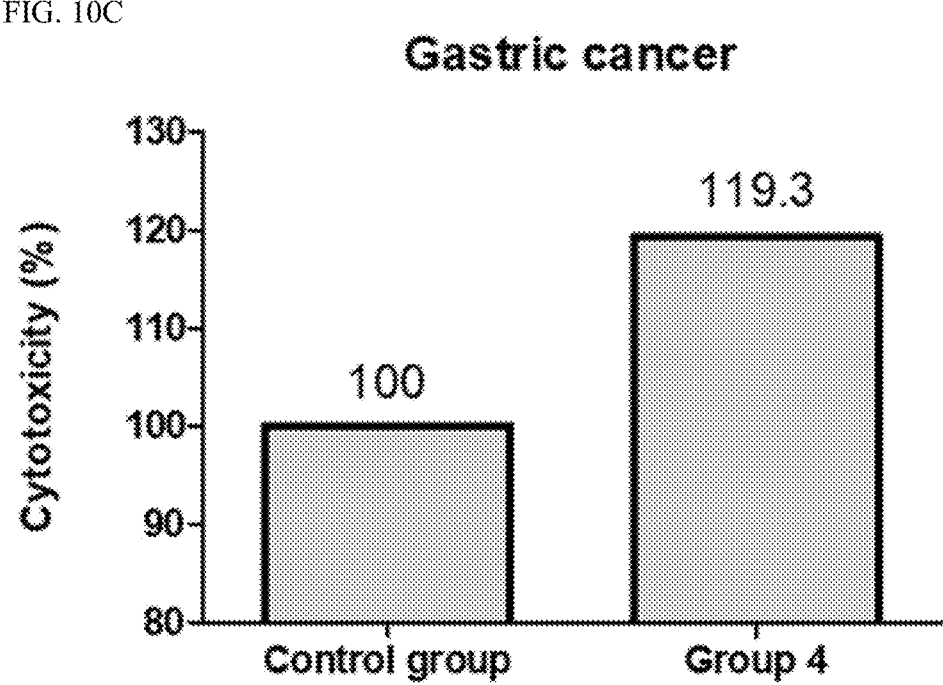
Figures 11A, 11B:
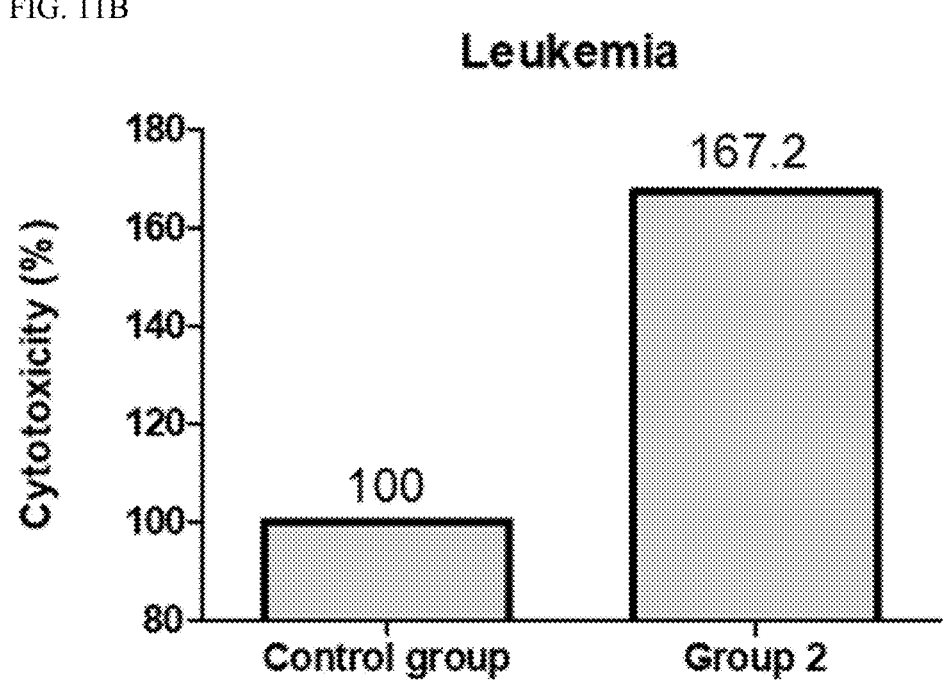
FIGS. 11A, 11B, 11C and 11D show the cytotoxicity (%) of PBMC when leukemia cell line U937 and PBMC were treated with KIRREL3 inhibitors.
Figure 11C:
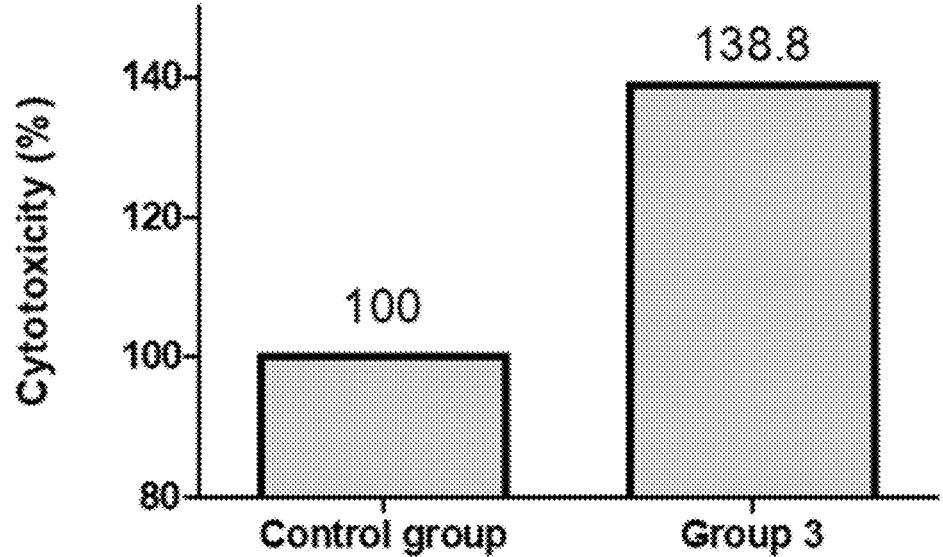
Figure 11D:
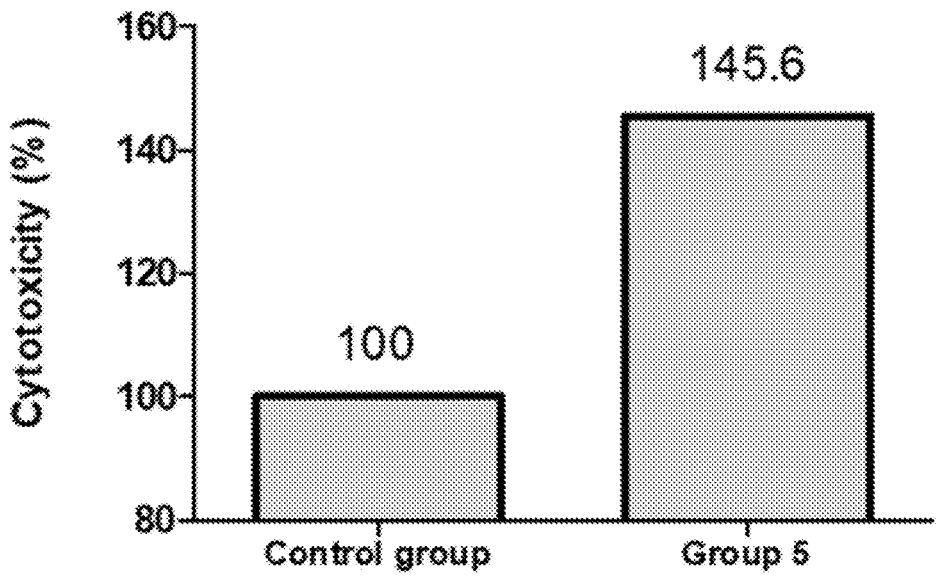
Figure 12A:
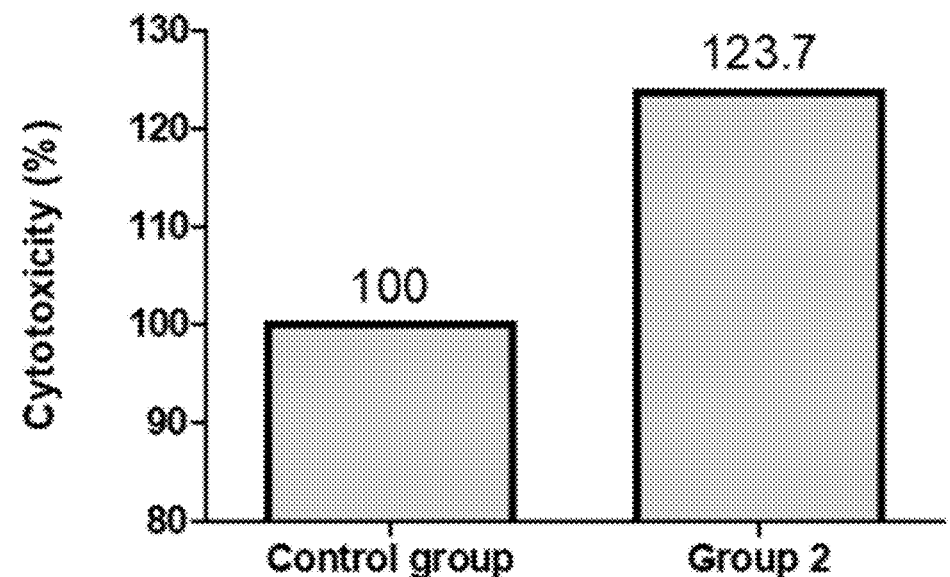
FIGS. 12A, 12B, 12C and 12D show the cytotoxicity (%) of PBMC when lung cancer cell line A549 and PBMC were treated with CNTN4 inhibitors.
Figure 12B:
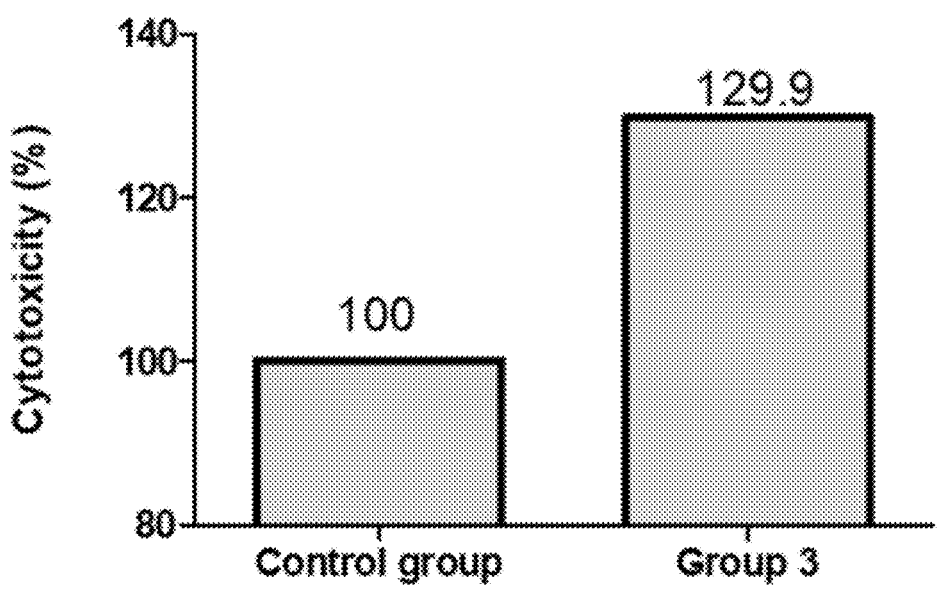
Figures 12C, 12D:
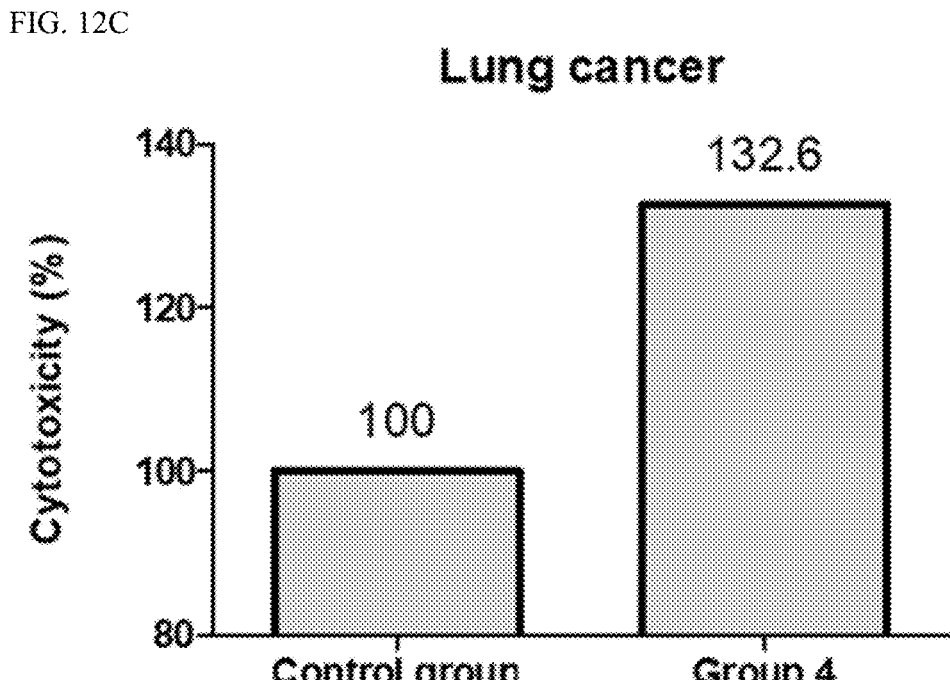
Figures 13C, 13D:
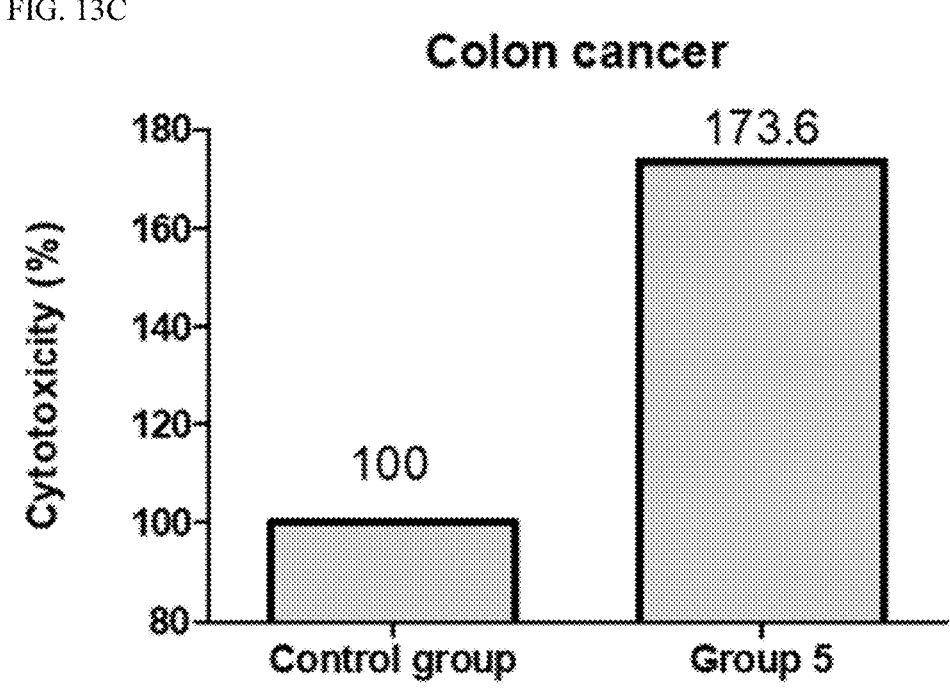
Figure 14A:
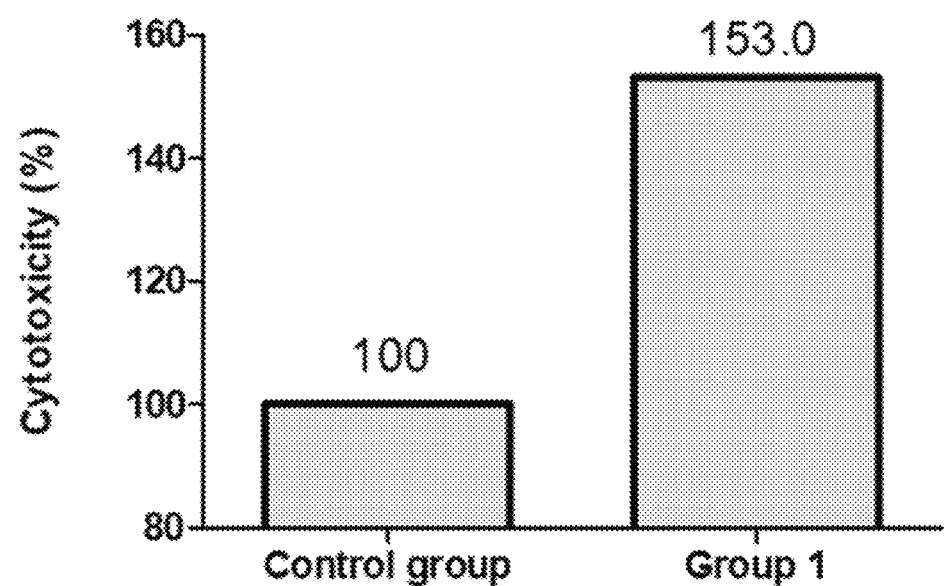
FIGS. 14A, 14B, 14C and 14D show the cytotoxicity (%) of PBMC when breast cancer cell line MDA-MB-231 and PBMC were treated with CNTN4 inhibitors.
Figure 14B:
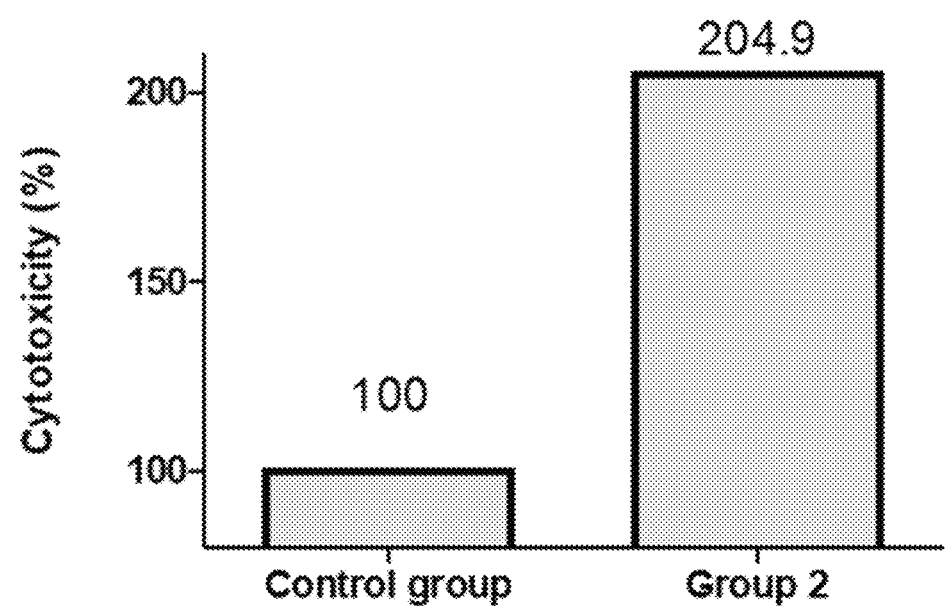
Figure 14C:
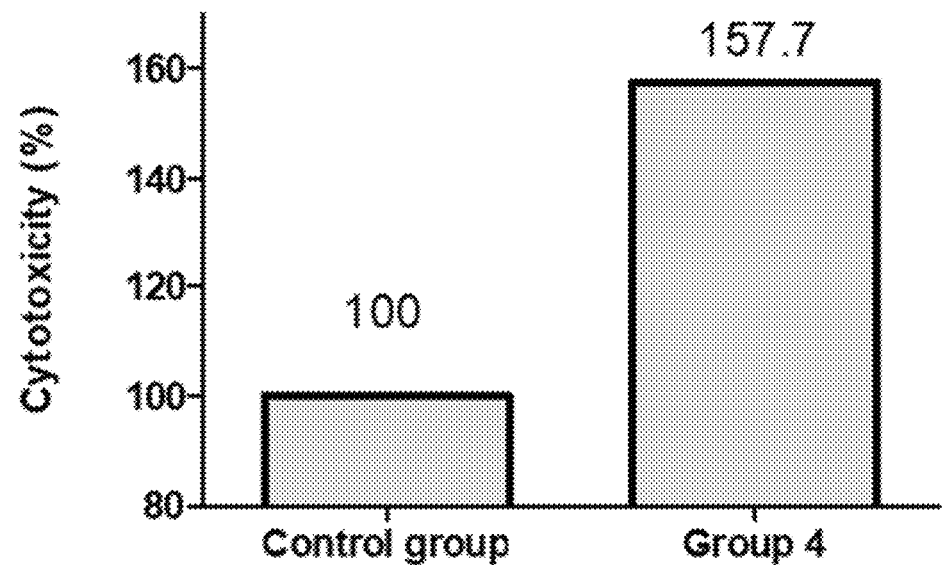
Figure 14D:
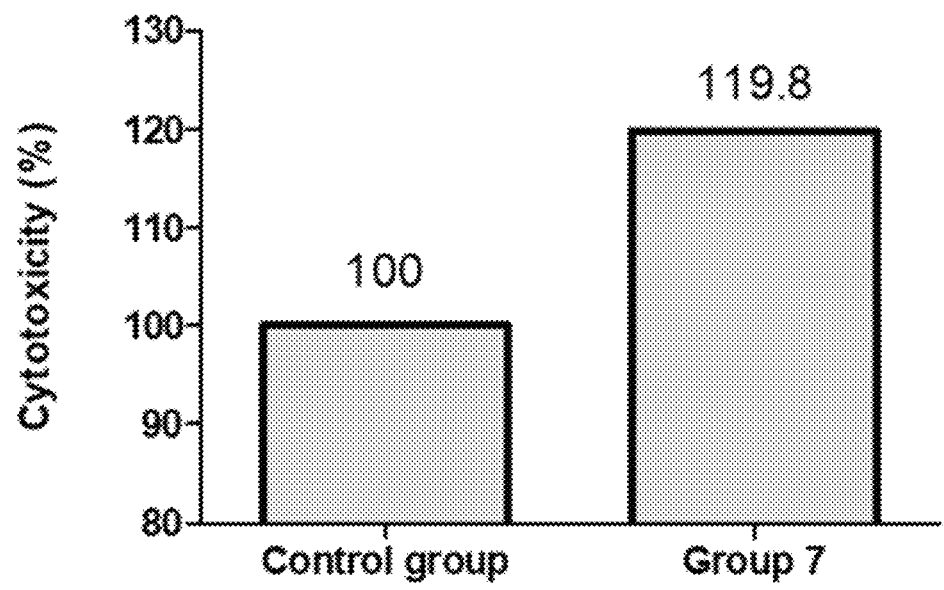
Figure 15A:
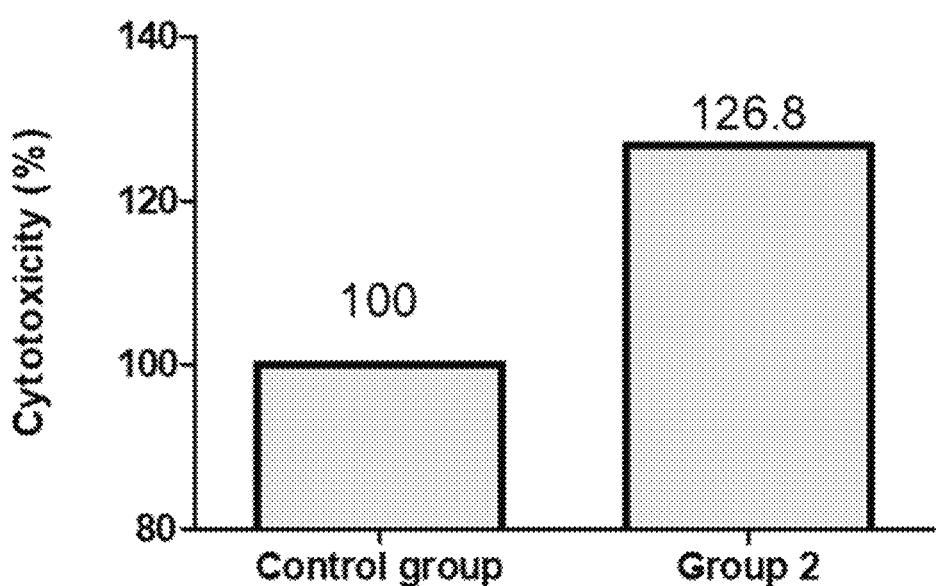
Figure 15B:
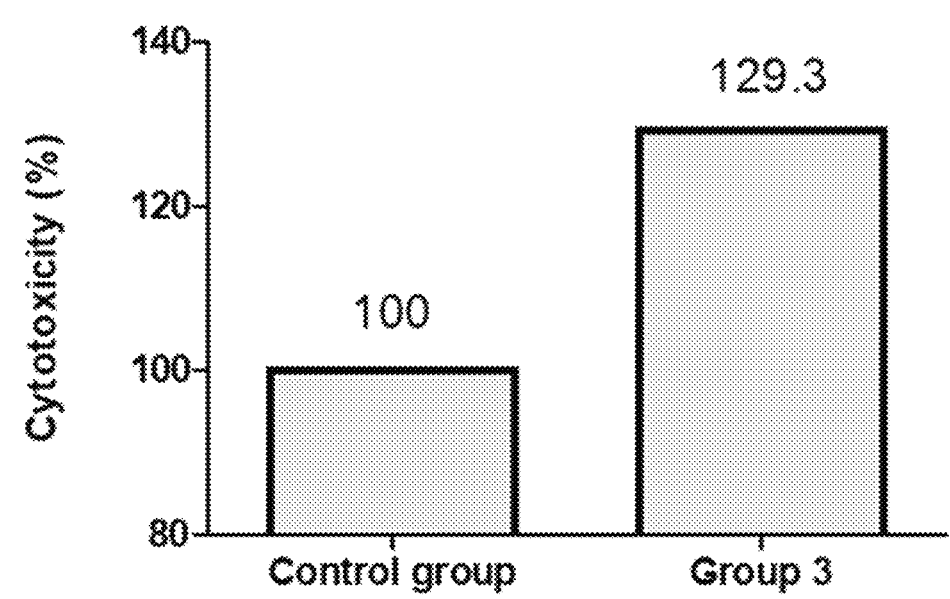
Figures 16A, 16B:
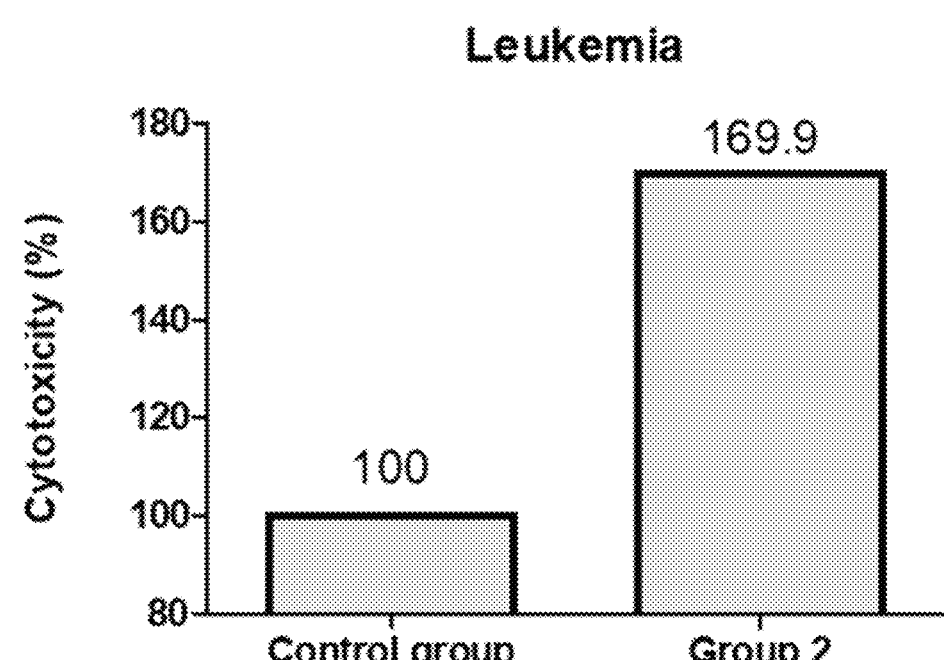
Figure 17C:
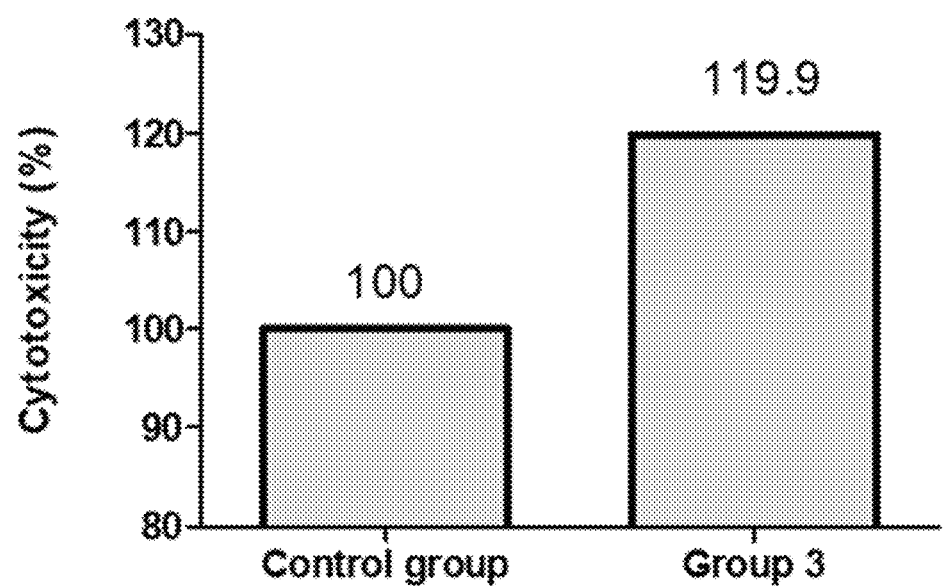
Figure 17D:
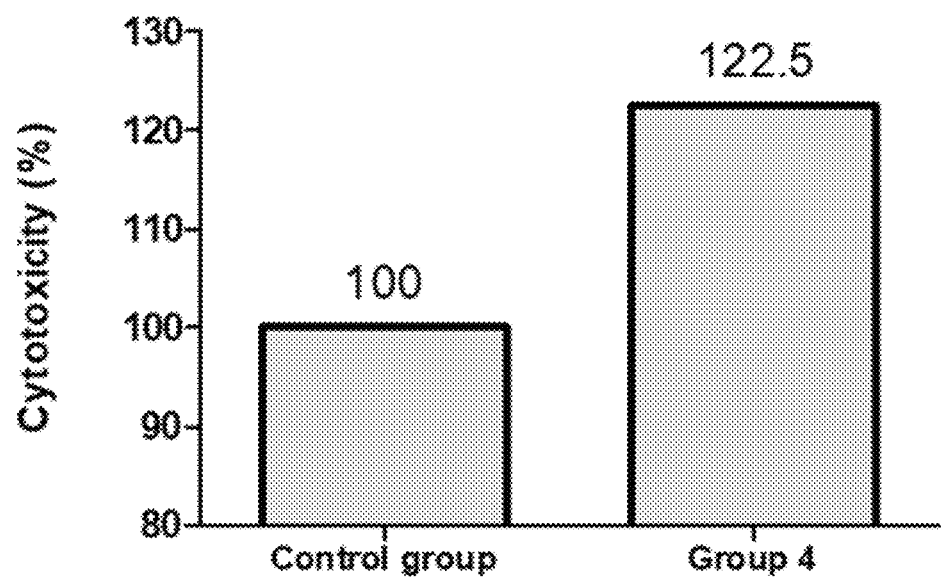
Figure 18A:
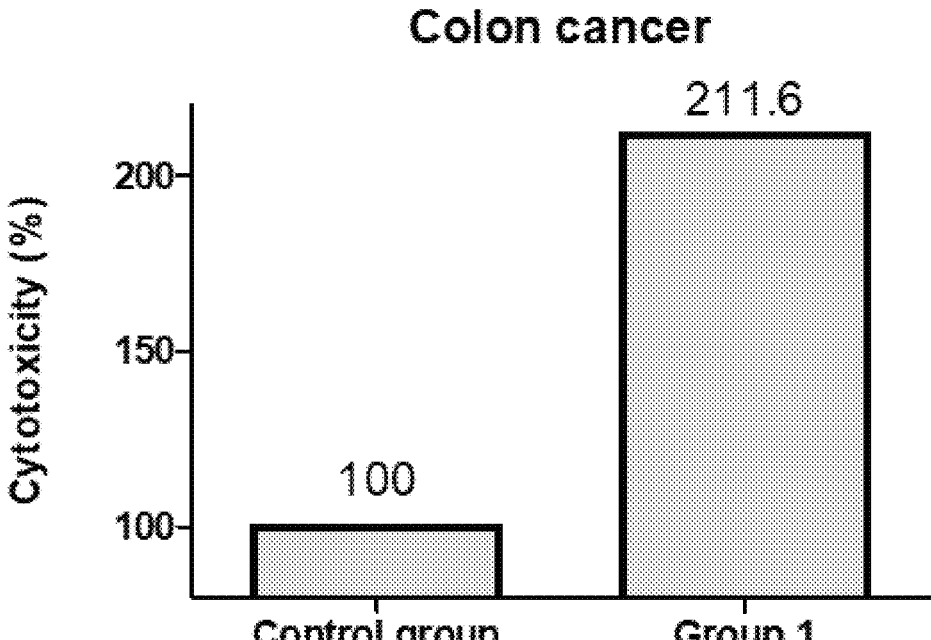
Figure 18B:
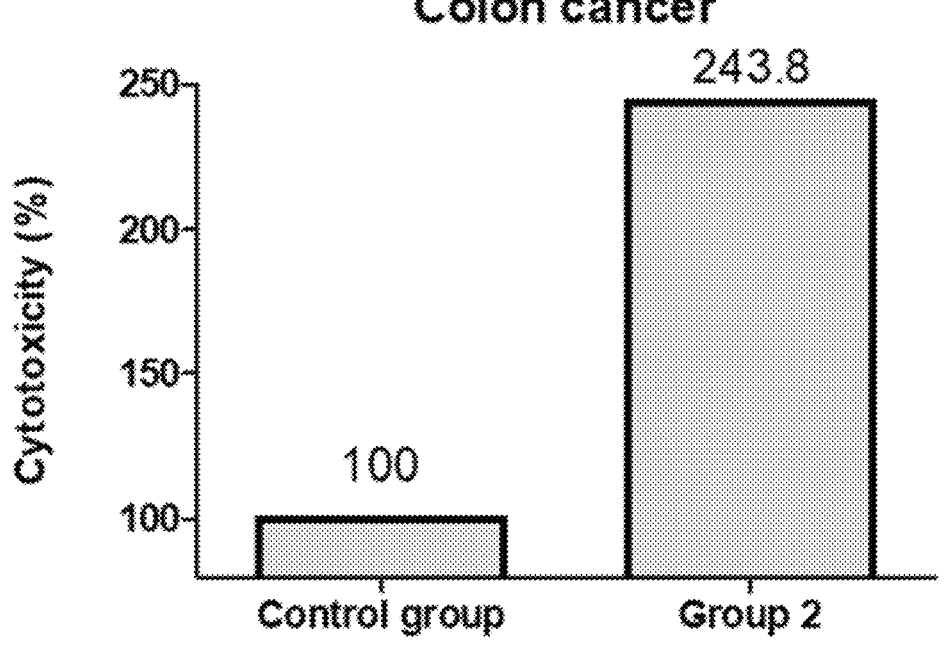
Figure 19A:
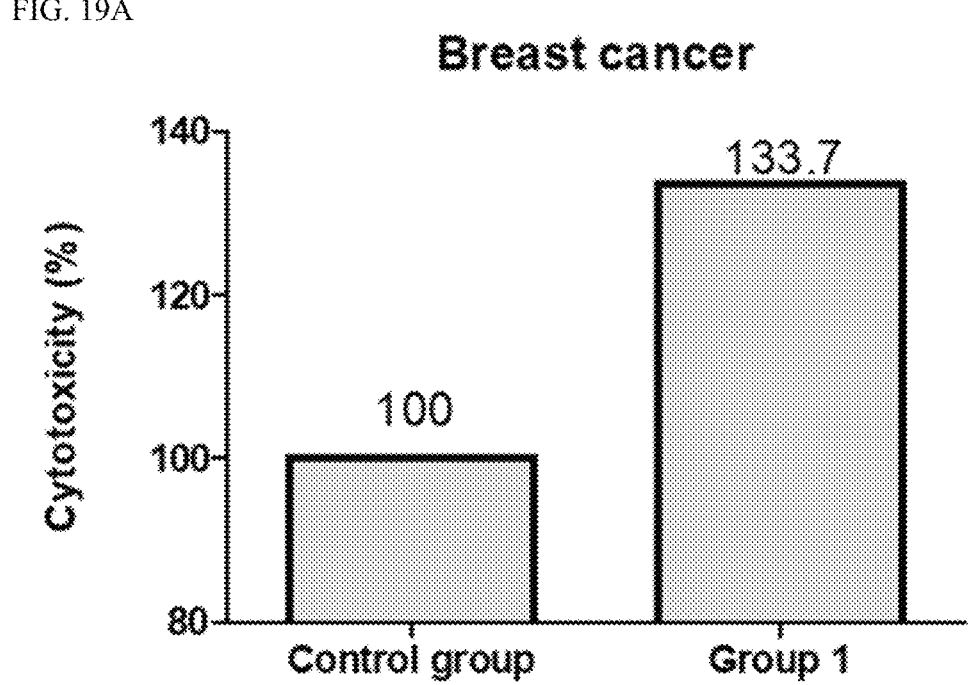
Figure 19B:
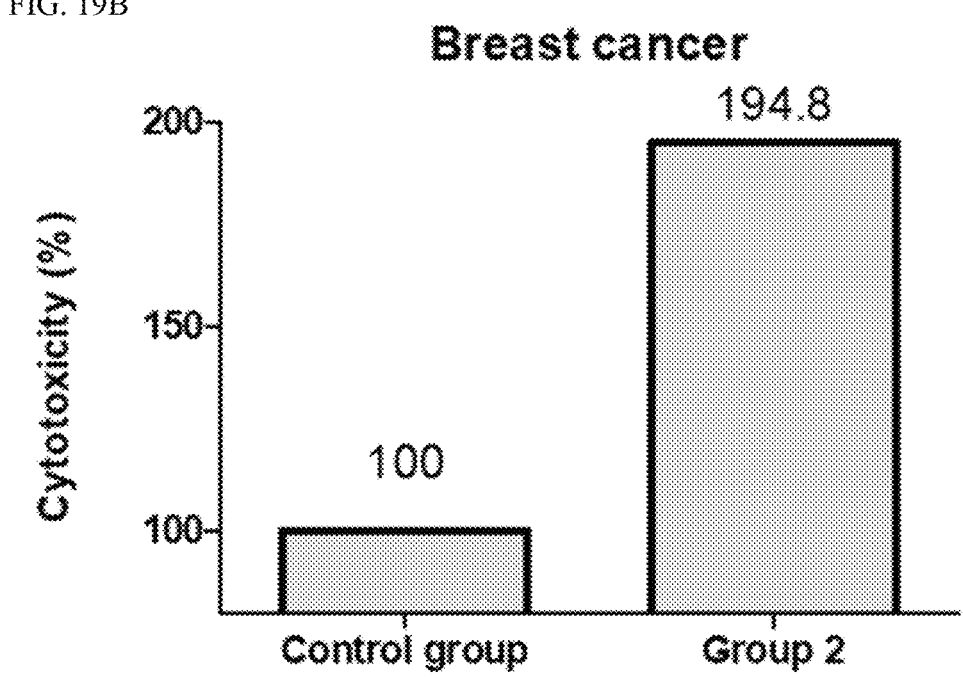
Figure 20A:
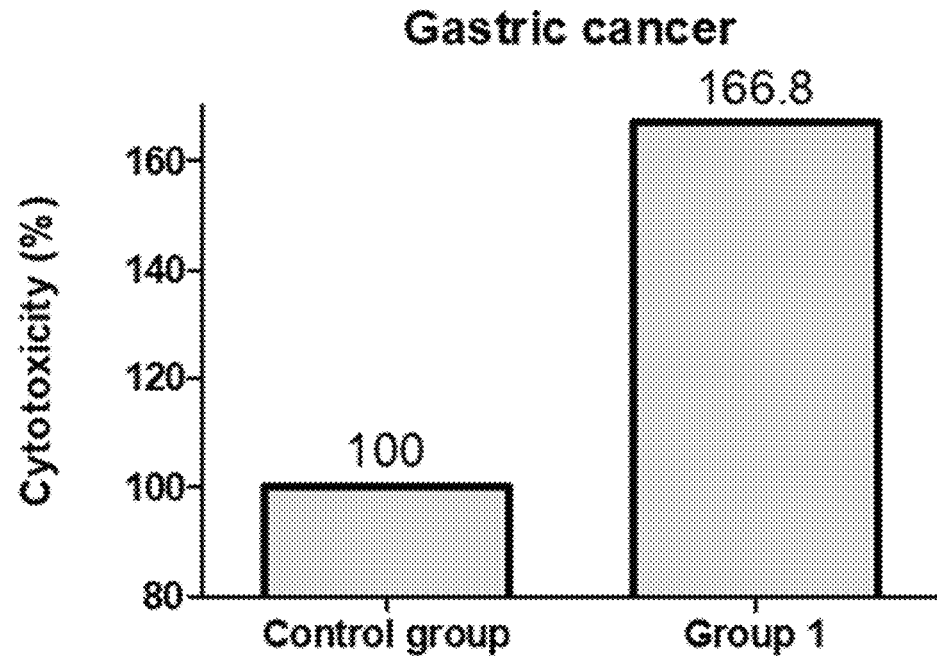
Figure 20B:
Figure 21A:
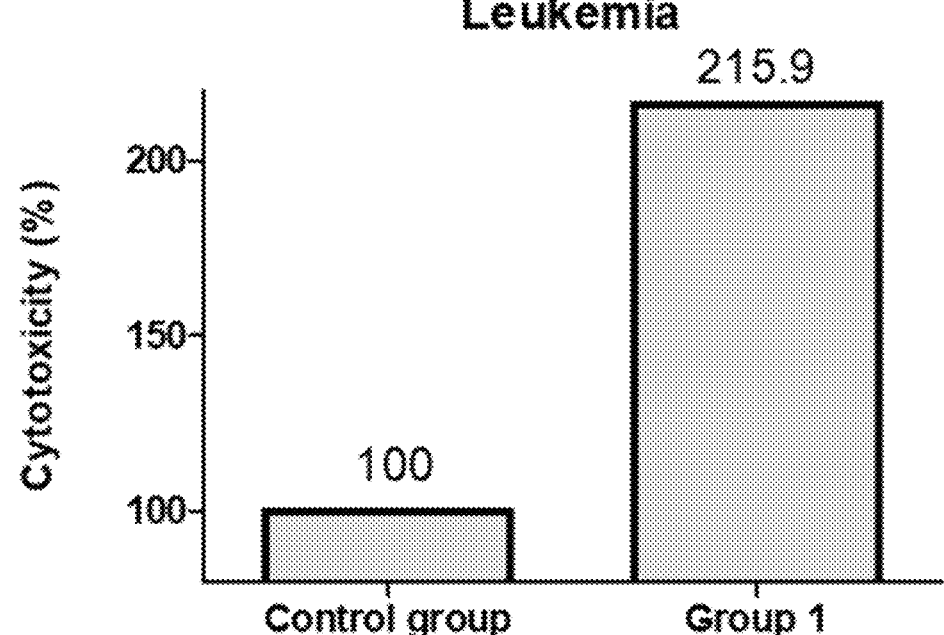
FIGS. 21A, 21B, 21C and 21D show the cytotoxicity (%) of PBMC when leukemia cell line U937 and PBMC were treated with CD351 inhibitors.
Figure 21B:
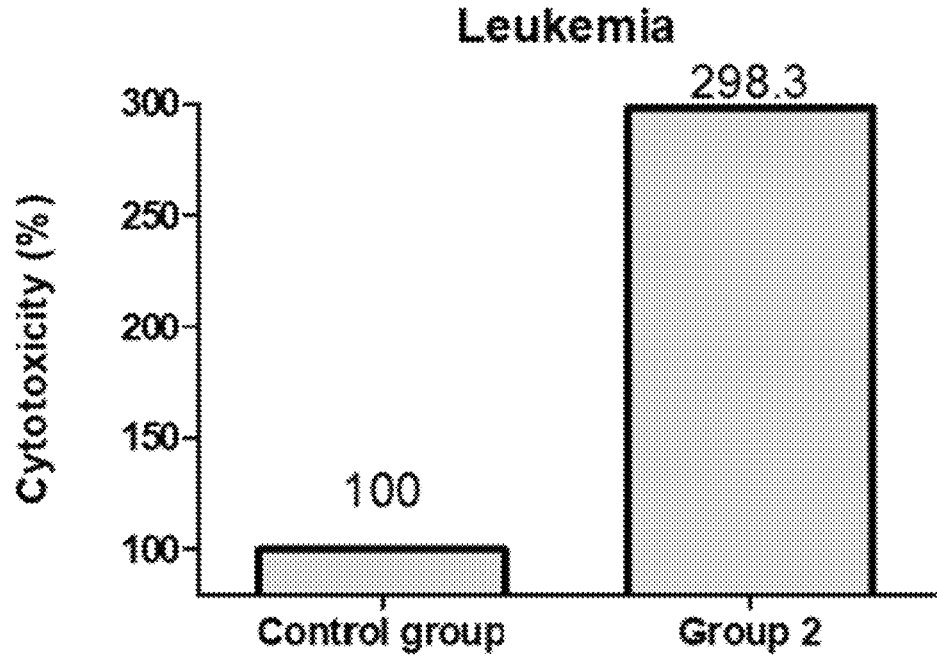
Figure 21C:
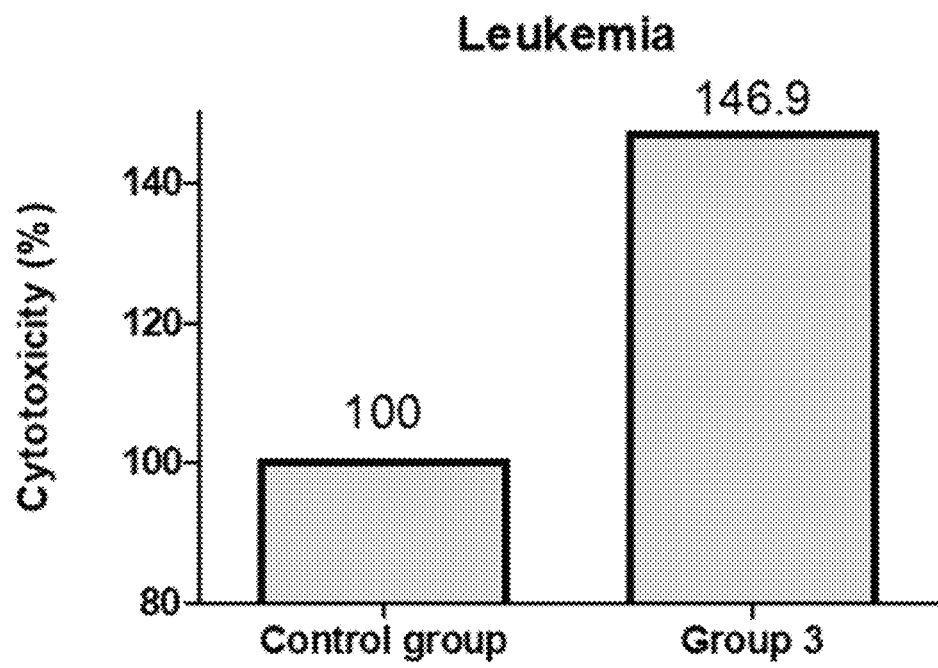
Figure 21D:
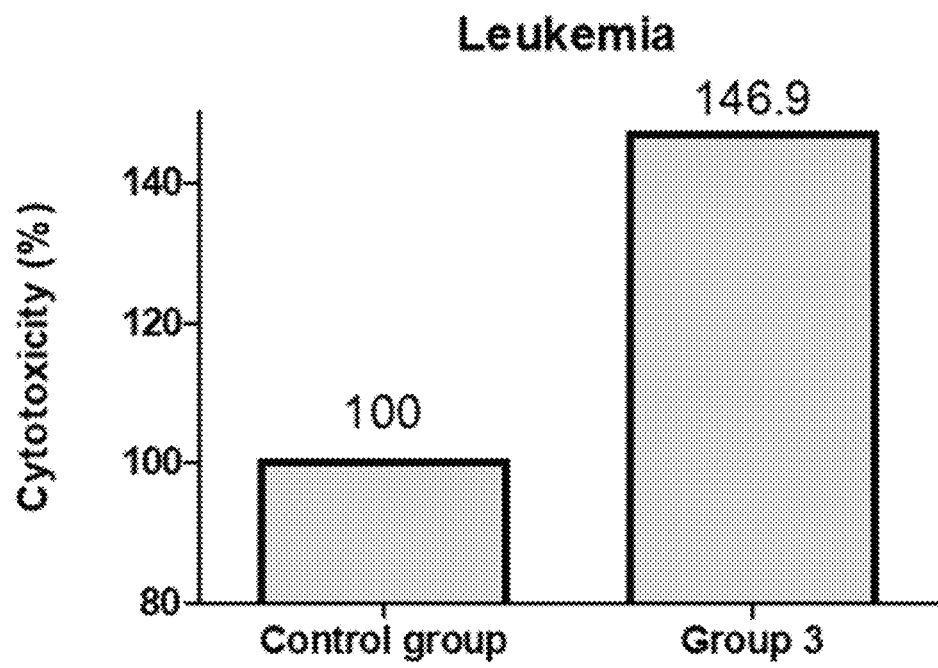

FIG. 5 and FIG. 6 show the percent proliferation (%) of CD4+ T cells and CD8+ T cells, respectively.

The control group treated with PD-L1 significantly inhibited the proliferation of CD4+ T cells compared to the control group treated with IgG1, whereas it did not show a significant inhibition on the proliferation of CD8+ T cells compared to the control group treated with IgG1.

The group treated with CD351 remarkably inhibited the proliferation of both CD4+ T cells and CD8+ T cells compared to the control group treated with IgG1 as well as the control group treated with PD-L1.

It means that CD351 is neutralized by blocking or knockdown, the T cell proliferation inhibition of CD351 can be suppressed. Accordingly, the cancer treatment can be effectively achieved.

Example 2. PBMC cytotoxic function assay

This example is to confirm whether the cytotoxic ability of PBMC against cancer cells is increased when KIRREL3, CNTN4 or CD351 is neutralized using inhibitors of KIRREL3, CNTN4 or CD351.

2.1. Preparation of PBMC

Human blood was placed in a 10 ml tube coated with EDTA (or heparin) and mixed with PBS at a ratio of 1:1. Ficoll-Paque PLUS was placed in a 50 ml tube, and then the blood sample was added. After centrifugation, human PBMCs were collected. The resultant was centrifuged, and the supernatant was removed. Then, RBC lysis (1×) was added, pipetted, and stored on ice for 3 minutes. After that, 50 ml of 10% FBS RPMI1640 was added, and the mixture was centrifuged to remove the supernatant. Then, FACS buffer was added, and the supernatant was removed by centrifugation. Subsequently, 50 ml of MACS buffer (PBS cells and stored on ice for 10 minutes. Thereafter, the supernatant was removed by centrifugation. The resultant was added with 30 ml of FACS buffer, pipetted, and centrifuged to remove the supernatant. Then, 10% FBS RPMI1640 was added, pipetted, and centrifuged to remove the supernatant. Thereafter, the resultant was mixed with 10 ml of 10% FBS RPMI1640, and the number of cells was counted.

Each PBMC-containing well of the 96-well plate prepared in the Example 2.1 was added with the cancer cells at the number of $3\times10^4$ cells in an amount of 100 μl.

2.3. Measurement of Cytotoxicity of PBMC Against Cancer Cells

The mixtures of PBMCs and cancer cells were prepared in the Example 2.2. These mixtures were incubated for 24 hours with 10 μg/mL of anti-human KIRREL3 antibody, anti-human CNTN4 antibody or anti-human CD351 antibody, or 50 nM of KIRREL3 siRNA, CNTN4 siRNA or CD351 siRNA.

Table 1 below provides the non-treated control group and Groups 1 to 4 using four neutralizing antibodies for blocking KIRREL3, and Table 2 below provides the non-treated control group and Groups 5 to 7 using three siRNAs for knockdown of KIRREL3.

TABLE 1

| human KIRREL3 neutralizing antibody | |
| --- | --- |
| Control group | Not treated |
| Group 1 | anti-human KIRREL3 antibody (R&D, AF4910) |
| Group 2 | anti-human KIRREL3 antibody (Bioss, bs-11864R) |
| Group 3 | anti-human KIRREL3 antibody (genetex, GTX32140) |
| Group 4 | anti-human KIRREL3 antibody (LSbio, LS-C336219) |

TABLE 2

| human KIRREL3 siRNA | |
| --- | --- |
| Control group | Not treated |
| Group 5 | Sense (5'-CUCUCAAGUUACCCACAGUtt-3') (SEQ ID NO: 1)<br>Antisense (5'-ACUGUGGGUAACUUGAGAGtt-3') (SEQ ID NO: 2) |
| Group 6 | Sense (5'-GGAGAGGUGUACAGGACCAtt-3') (SEQ ID NO: 3)<br>Antisense (5'-UGGUCCUGUACACCUCUCCtt-3') (SEQ ID NO: 4) |
| Group 7 | Sense (5'-UCUCAAGUUACCCACAGUAtt-3') (SEQ ID NO: 5)<br>Antisense (5'-UACUGUGGGUAACUUGAGAtt-3') (SEQ ID NO: 6) | containing 0.5% bovine serum albumin and 2 mM EDTA) was added, the number of cells was counted, and the supernatant was completely removed after centrifugation.

96-well plates were coated with 1.0 μg/ml of anti-CD3 antibody (BioLegend, Cat. No. 317325) in PBS at 4° C., and the wells were washed three times with PBS. The PBMC prepared in the above was mixed with 10% FBS RPMI1640, and was added to each well of the 96-well plate at the number of $6\times10^5$ cells in an amount of 100 μl. The PBMC was activated by anti-CD3 antibody for 72 hours.

2.2. Preparation of Cancer Cells

Lung cancer cell line A549, colon cancer cell line HCT-116, breast cancer cell line MDA-MB-231, gastric cancer cell line MKN-74, and leukemia cell line U937 were respectively mixed with 1 μl of CFSE (carboxyfluorescein succinimidyl ester), and then stored at 37° C. for 3 minutes. Subsequently, FBS was added into tubes containing cancer Table 3 below provides the non-treated control group and Groups 1 to 5 using five neutralizing antibodies for blocking CNTN4, and Table 4 below provides the non-treated control group and Groups 6 to 8 using three siRNAs for knockdown of CNTN4.

TABLE 3

| human CNTN4 neutralizing antibody | |
| --- | --- |
| Control group | Not treated |
| Group 1 | anti-human CNTN4 antibody (R&D, MAB2205) |
| Group 2 | anti-human CNTN4 antibody (abcam, ab137107) |
| Group 3 | anti-human CNTN4 antibody (abcam, ab131285) |
| Group 4 | anti-human CNTN4 antibody (LSbio, LS-C119876) |
| Group 5 | anti-human CNTN4 antibody (Abnova, PAB27653) |

TABLE 4

| human CNTN4 siRNA | |
|---|---|
| Control group | Not treated |
| Group 6 | Sense (5'-CAGUAUCUUUGCCAGAAGUtt-3') (SEQ ID NO: 7) |
| | Antisense (5'-ACUUCUGGCAAAGAUACUGtt-3') (SEQ ID NO: 8) |
| Group 7 | Sense (5'-GAUAAUGAGUCGGAAGUAAtt-3') (SEQ ID NO: 9) |
| | Antisense (5'-UUACUUCCGACUCAUUAUCtt-3') (SEQ ID NO: 10) |
| Group 8 | Sense (5'-GUGACAAUAGACGAAAUCAtt-3') (SEQ ID NO: 11) |
| | Antisense (5'-UGAUUUCGUCUAUUGUCACtt-3') (SEQ ID NO: 12) |

Table 5 below provides the non-treated control group and Groups 1 to 3 using three neutralizing antibodies for blocking CD351, and Table 6 below provides the non-treated control group and Groups 4 to 6 using three siRNAs for knockdown of CD351.

TABLE 5

| human CD351 neutralizing antibody | |
|---|---|
| Control group | Not treated |
| Group 1 | anti-human CD351 antibody (Biolegend, 13730) |
| Group 2 | anti-human CD351 antibody (Creative diagnostics, CABT-BL4657) |
| Group 3 | anti-human CD351 antibody (Biobyt, orb183662) |

TABLE 6

| human CD351 siRNA | |
|---|---|
| Control group | Not treated |
| Group 4 | Sense (5'-GAGAGAUGAACUGCUCAGUtt-3') (SEQ ID NO: 13) |
| | Antisense (5'-ACUGAGCAGUUCAUCUCUCtt-3') (SEQ ID NO: 14) |
| Group 5 | Sense (5'-GAGAACUUCCAACUCAGUAtt-3') (SEQ ID NO: 15) |
| | Antisense (5'-UACUGAGUUGGAAGUUCUCtt-3') (SEQ ID NO: 16) |
| Group 6 | Sense (5'-AGAGAACUUCCAACUCAGUtt-3') (SEQ ID NO: 17) |
| | Antisense (5'-ACUGAGUUGGAAGUUCUCUtt-3') (SEQ ID NO: 18) |

After twenty-four hours from incubating the mixtures of PBMCs and cancer cells with antibody or siRNA, cells were stained with 7-aminoactinomycin D (7-AAD; BD Pharmingen, San Diego, CA, USA) to detect lysed cells. The cytotoxicity of PBMC against cancer cells was analyzed by determining FL-1 (CFSE) and FL-3 (7-AAD) staining using a FACSDiVa software (BD Biosciences).

2.4. Results

For the lung cancer cell line A549, FIGS. 7A, 7B, 7C and 7D show the results treated with KIRREL3 neutralizing antibody or siRNA, FIGS. 12A, 12B, 12C and 12D show the results treated with CNTN4 neutralizing antibody or siRNA, and FIGS. 17A, 17B, 17C and 17D show the results treated with CD351 neutralizing antibody or siRNA.

When the lung cancer cell line A549 and PBMC were treated with KIRREL3 neutralizing antibody, CNTN4 neutralizing antibody or CD351 neutralizing antibody, the cytotoxicity against lung cancer cell was significantly increased compared to the non-treated control group even though there is more or less degree of difference depending on the type of antibody. Further, the cytotoxicity against lung cancer cell was also significantly increased when it was treated with KIRREL3 siRNA, CNTN4 siRNA or CD351 siRNA.

Using KIRREL3 neutralizing antibody or siRNA, the results on the colon cancer cell line HCT-116 are shown in FIGS. 8A, 8B, 8C and 8D, the result on the breast cancer cell line MDA-MB-231 are shown in FIGS. 9A, 9B, 9C and 9D, the results on the gastric cancer cell line MKN-74 are shown in FIGS. 10A, 10B, 10C and 10D, and the results on the leukemia cell line U937 are shown in FIGS. 11A, 11B, 11C and 11D.

In addition, using CNTN4 neutralizing antibody or siRNA, the results on the colon cancer cell line HCT-116 are shown in FIGS. 13A, 13B, 13C and 13D, the results on the breast cancer cell line MDA-MB-231 are shown in FIGS. 14A, 14B, 14C and 14D, the results on the gastric cancer cell line MKN-74 are shown in FIGS. 15A, 15B, 15C and 15D, and the results on the leukemia cell line U937 are shown in FIGS. 16A, 16B, 16C and 16D.

In addition, using CD351 neutralizing antibody or siRNA, the results on the colon cancer cell line HCT-116 are shown in FIGS. 18A, 18B, 18C and 18D, the results on the breast cancer cell line MDA-MB-231 are shown in FIGS. 19A, 19B, 19C and 19D, the results on the gastric cancer cell line MKN-74 are shown in FIGS. 20A, 20B, 20C and 20D, and the results on the leukemia cell line U937 are shown in FIGS. 21A, 21B, 21C and 21D.

As shown in FIGS. 8A to 11D, 13A to 16D, and 18A to 21D, when one or more of KIRREL3, CNTN4 and CD351 were neutralized by antibodies or siRNAs, the results of increasing the cytotoxicity of PBMC were also observed in colon cancer, breast cancer, gastric cancer and leukemia.

Example 3. Tumor-Mouse Model Experiment

This example is to confirm whether the growth of tumor in mouse is suppressed when KIRREL3, CNTN4 or CD351 is neutralized using inhibitors of KIRREL3, CNTN4 or CD351.

3.1. Establishment of Tumor-Mouse Model

MC-38 cell line derived from C57bL6 colon adenocarcinoma cells was resuspended in 50 μl PBS at the number of $2 \times 10^5$ cells, and was subcutaneously injected into the flanks of 6-week-old female C57bL6 mice.

Table 7 below provides the non-treated control group and Group 8 using a siRNA for knockdown of KIRREL3.

TABLE 7

|  | mouse KIRREL3 siRNA |
| --- | --- |
| Control group | Not treated |
| Group 8 | Sense (5'-GUAAAGGAGAGGUCAUCAA-3') (SEQ ID NO: 19)<br>Antisense (5'-UUGAUGACCUCUCCUUUAC-3') (SEQ ID NO: 20) |

Table 8 below provides the non-treated control group and Group 9 using a siRNA for knockdown of CNTN4.

TABLE 8

|  | mouse CNTN4 siRNA |
| --- | --- |
| Control group | Not treated |
| Group 9 | Sense (5'-GUGUAGACAAACUCUCUGU-3') (SEQ ID NO: 21)<br>Antisense (5'-ACAGAGAGUUUGUCUACAC-3') (SEQ ID NO: 22) |

Table 9 below provides the non-treated control group and Groups 7, 8 and 9 using three siRNAs for knockdown of CD351.

TABLE 9

|  | mouse CD351 siRNA |
| --- | --- |
| Control group | Not treated |
| Group 7 | Sense (5'-GUCCAUCCAACACCACCUA-3') (SEQ ID NO: 23)<br>Antisense (5'-UAGGUGGUGUUGGAUGGAC-3') (SEQ ID NO: 24) |
| Group 8 | Sense (5'-CUGAUGAGGGAAAGAACUU-3') (SEQ ID NO: 25)<br>Antisense (5'-AAGUUCUUUCCCUCAUCAG-3') (SEQ ID NO: 26) |
| Group 9 | Sense (5'-CAGCUAAGCCCAGUGAACA-3') (SEQ ID NO: 27)<br>Antisense (5'-UGUUCACUGGGCUUAGCUG-3') (SEQ ID NO: 28) |

In all Groups, the siRNA targeting mouse KIRREL3, mouse CNTN4 or mouse CD351 was injected into the tumor of mice three times at the interval of 5 days from the 11th day after injecting MC-38 cells. Specifically, 10 μg siRNA and 7.5 μl oligofectamine (Invitrogen) in PBS were mixed according to manufacturer's instruction, and then injected into the tumor tissue induced in mice at a dose of 0.5 mg/kg.

3.2. Results

Figure 22:
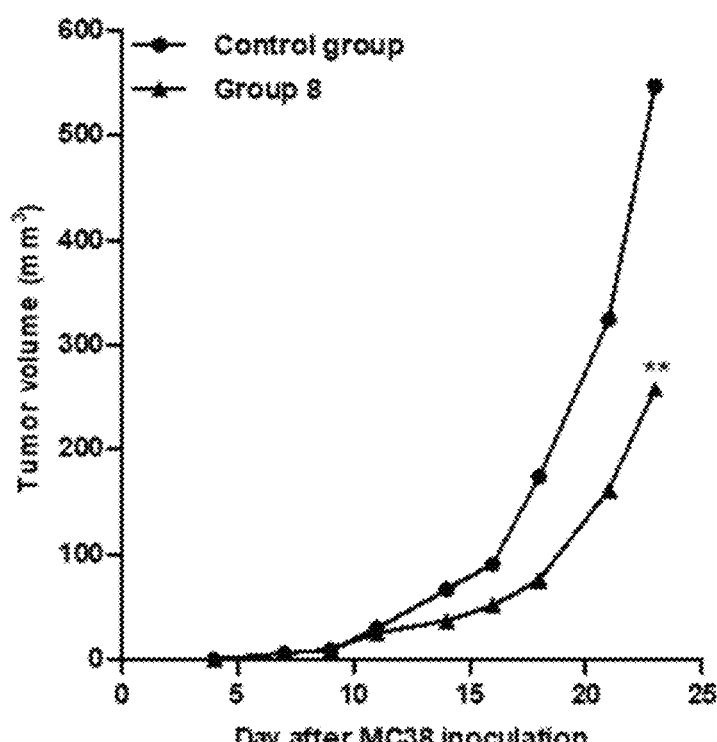
FIG. 22 shows the tumor size in mouse treated with KIRREL3 inhibitors.
Figure 23:
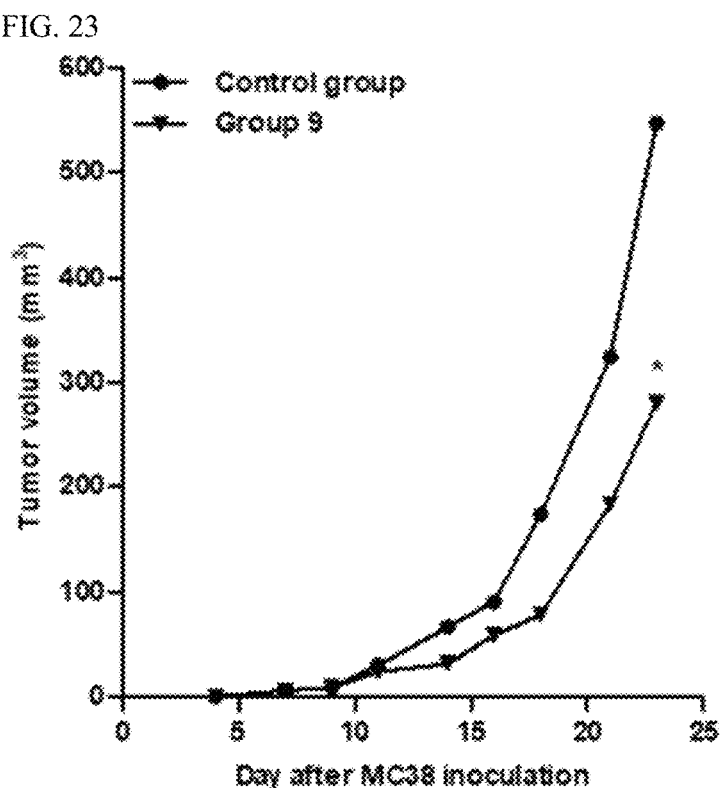
FIG. 23 shows the tumor size in mouse treated with CNTN4 inhibitors.
Figure 24A:
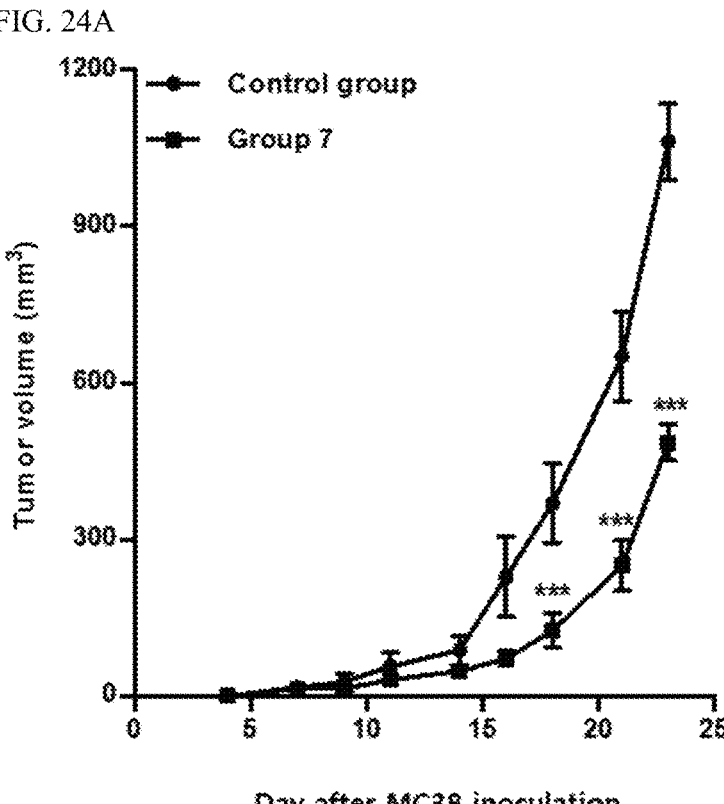
Figure 24B:
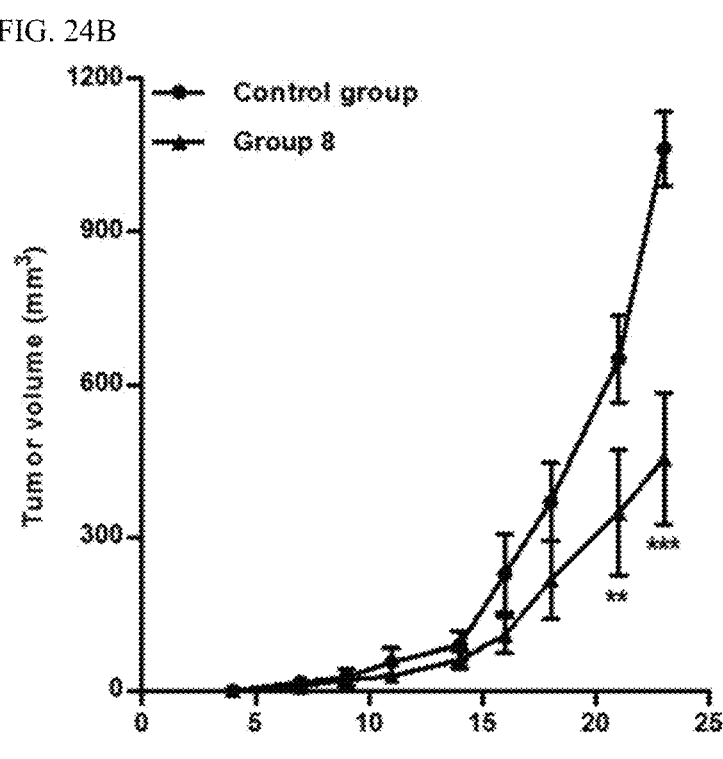
Figure 24C:
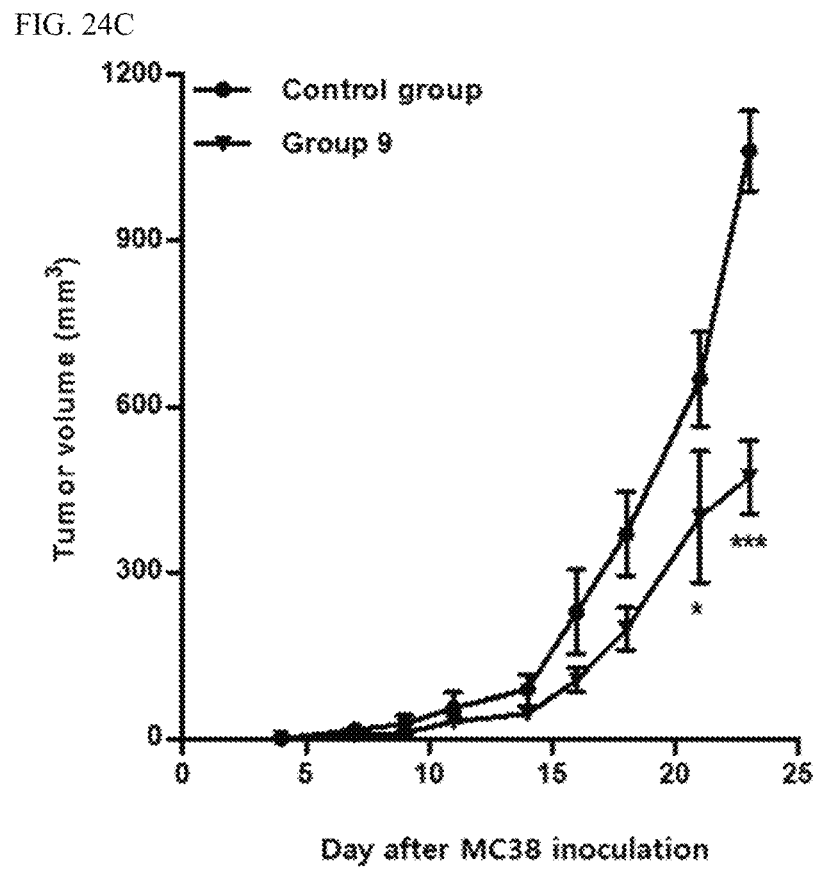

FIG. 22 provides the result on the size of tumor in mice of the non-treated control group and Group 8 wherein KIRREL3 was knocked down. FIG. 23 provides the result on the size of tumor in mice of the non-treated control group and Group 9 wherein CNTN4 was knocked down. FIGS. 24A, 24B and 24C provide the results on the size of tumor in mice of the non-treated control group and Groups 7 to 9 wherein CD351 was knocked down.

In the non-treated control group, the tumor continued to grow after it occurred. Compared to the non-treated control group, the growth rate of tumor in mouse was remarkably inhibited in Groups wherein KIRREL3, CNTN4 or CD351 was knocked down. It means that when one or more of KIRREL3, CNTN4 and CD351 are blocked or knocked down to inhibit its activity or expression, the development of cancer is delayed or stopped and the occurrence of cancer is inhibited. Accordingly, one or more inhibitors of KIRREL3, CNTN4 and CD351 can be efficiently used to prevent cancer.

Example 4. Analysis on Binding Site of CNTN4 and APP

This example is to confirm the binding site of CNTN4 and its receptor, APP.

4.1. Preparation of Overexpression Cell (Transient Transfection)

HEK293FT cell was spread in a culture dish plate at the number of $3\times10^6$ cells. After 24 hours, jetPRIME transfection buffer 200 μL; CNTN4 expression plasmid 10 μg or APP expression plasmid 10 μg; and RIME transfection reagent 20 μL were mixed, incubated at room temperature (RT) for 10 min, and adding the mixture in the cell, so that the HEK293FT cell was transfected with each plasmid.

Figure 25A:
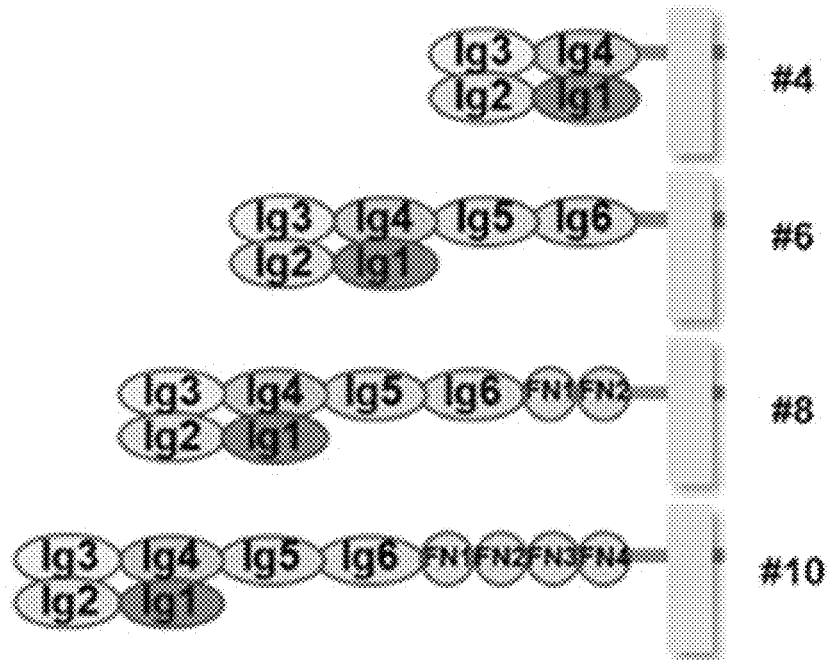
FIGS. 25A and 25B depict the structure of CNTN4 and APP as prepared in accordance with Example 4.

The four plasmids in total were prepared for CNTN4 expression. CNTN4 consists of a total of ten (10) domains, i.e., Ig1 to Ig6 and FN1 to FN4. Ig1 to Ig4, Ig1 to Ig6, Ig1 to FN2, and Ig1 to FN4 were expressed in each plasmid (Ig; Ig like domain, FN; fibronection), wherein the deletion structures expressed in each plasmid were named as #4, #6, #8, and #10 (FIG. 25A).

Figure 25B:
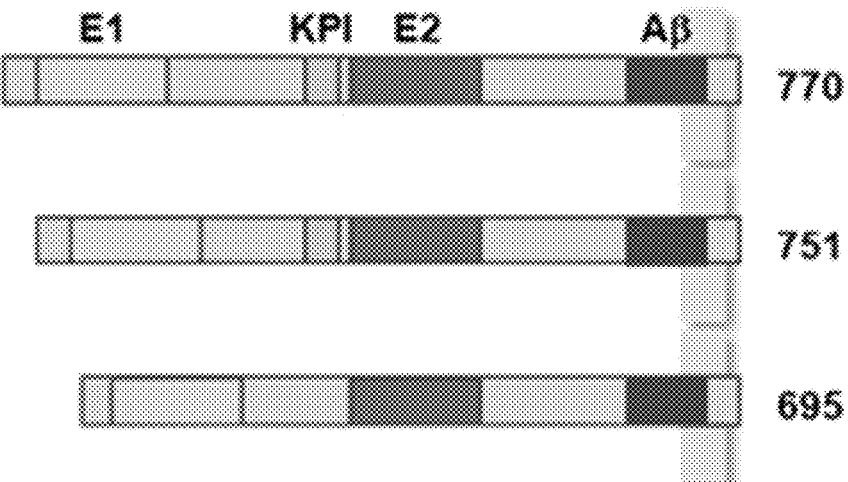

The three plasmids in total were prepared for APP expression. Each of the three isoforms of APP was expressed in each plasmid, which was named as 770, 751, and 695. The 770 and 751 isoforms include KPI (Kunitz-type protease inhibitor) domain, while the 695 isoform do not KPI domain (FIG. 25B).

4.2. Immunoprecipitation (IP)

4.2.1. Protein to Protein Interaction

Each of the total seven groups of the transfected cells prepared in Example 4.1. was centrifuged at 1,200 rpm and 4° C. for 3 min to remove the supernatant. The cell pellet was lysed with 1× lysis buffer, reacted at 4° C. for 10 mins, and again centrifuged at 13,000 rpm and 4° C. for 10 min to obtain cell lysates.

6 μL of cell lysate sample and 24 μL of UltraPure distilled water were mixed in a new 1.5 mL tube to dilute the sample 1/5. Separately, 2 mg/mL standard BSA was diluted with UltraPure distilled water as a 1/2 serial dilution (i.e., 2, 1, 0.5, 0.25, 0.125, 0.0625, 0.031, 0 mg/mL). Samples and standard BSA as diluted were placed in a non-coated 96 well plate in an amount of 10 μL/well in duplication. Reagents A and B comprised in BCA assay kit were mixed in a ratio of 50:1 to be added into each well in an amount of 200 L/well, followed by reacting at 37° C. for 30 mins. The protein concentration was determined by using SpectraMax M2 Microplate Readers.

Then, CNTN4 #10 was reacted with APP 770, 751, or 695 to confirm whether the CNTN4-APP protein complex was produced. Similarly, APP 700 was reacted with CNTN4 #4, #6, #8, or #10 to confirm the same.

100 μg protein of each of total cell lysates, 500 μL PBS, and 2 μg IP Ab (anti-CNTN4 antibody or anti-APP antibody) were mixed and then was under rotation at 4° C. for overnight (O/N).

30 μL of 50% protein A/G agarose bead was then added, followed by being under rotation at RT for 2 h. The supernatant was removed by centrifugation at 4,000 rpm and 4° C. for 4 min, adding 1 mL of PBS, and then being under rotation at RT for 10 min, which was repeated three times in total. The supernatant was removed by centrifugation at 4,000 rpm and 4° C. for 4 min, adding 20 μL of 1× sample buffer that was prepared by mixing a sample buffer and a reducing agent, followed by reacting for 10 min at 95° C. heat block. Reaction was done in ice for 5 min and then spined down (IP sample).

The sample buffer and the reducing agent were added to 20 μg of cell lysates in total to become 20 μL, followed by reacting for 10 min at 95° C. heat block. Reaction was done in ice for 5 min and then spined down (Input sample).

4.2.2. SDS-PAGE and Western Blotting

NuPAGE 4-12% Bis-Tris gel was used in combination of NuPAGE® electrophoresis system. Gel was fixed in a chamber and a MES running buffer was filled between a gel cassette and an electrode assembly. A marker 5 μL and a sample (20 μL per well) were loaded and the electrophoresis was performed in accordance with the manufacturer manual.

After the completion of transfer, the membrane was blocked with 3% BSA blocking buffer at RT for 60 mins. After the blocking, washing process was repeated with PBST three times, diluting primary antibody with 0.3% BSA blocking buffer (1:1,000), and then stored in 4° C. frigo. Washing process was repeated with PBST three times, diluting secondary antibody with 0.3% BSA blocking buffer (1:5,000), and then reacting at RT for 60 mins. Again, the washing with PBST was done three times.

500 μL of Luminol/Enhancer solution and 500 μL of peroxide solution (commercially available in SuperSignal™ West Pico PLUS Chemiluminescent Substrate) were mixed in 1.5 mL tube and spread in the membrane. The image was scanned by using LOURMAT CHEMI-DOC.

Figure 26A:
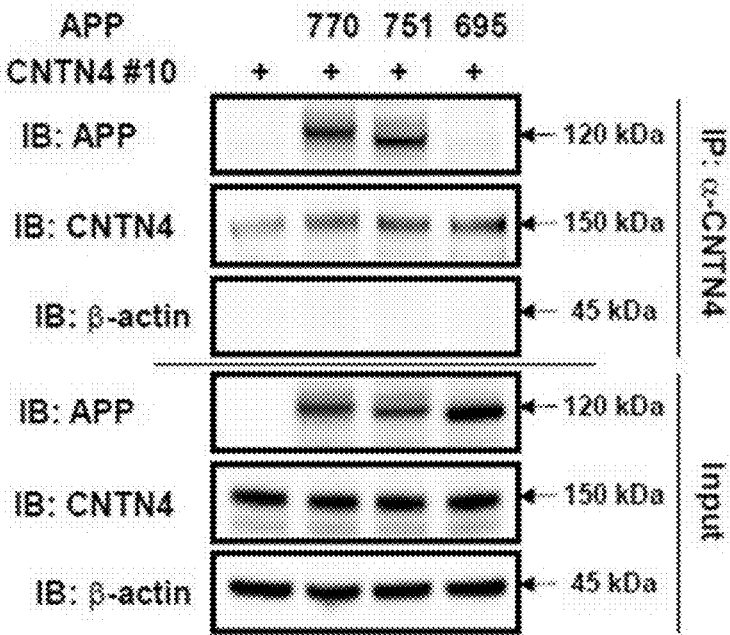
FIGS. 26A and 26B show an image obtained from SDS-Page and western blotting performed in Example 4.
Figure 26B:
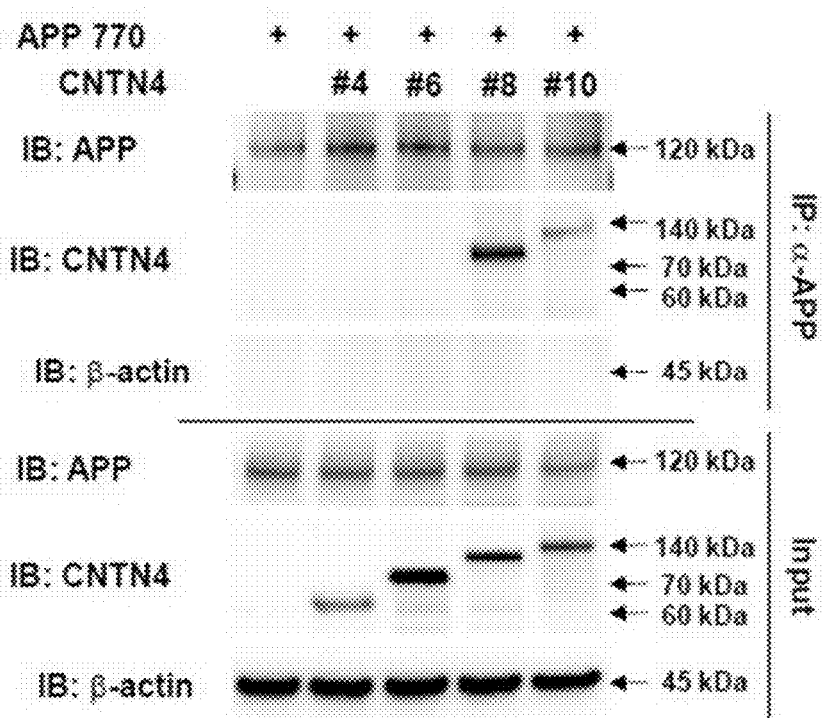

The results were shown in FIGS. 26A and 26B.

It was confirmed that CNTN4 #10 (full length) binds to APP (770 & 751) including KPI (kunitz-type protease inhibitor) domain (FIG. 26A), while APP 770 (full length) binds to CNTN4 (#8 & #10) including FN1 to FN2 domain (domain 7~domain 8) (FIG. 26B). As such, it was confirmed that the APP binding site to CNTN4 is the KPI domain, and the corresponding CNTN4 binding site is FN1 to FN2 domain (domain 7~domain 8). The sequences of each domain were depicted in Table 10 and FIG. 27.

TABLE 10

| SEQ ID NO: 29 | FN1 to FN2 domain | PPEAVTIDEITDTTAQLSWRPGPDNHSPIT MYVIQARTPFSVGWQAVSTVPELIDGKTFT ATVVGLNPWVEYEFRTVAANVIGIGEPSRP SEKRRTEEALPEVTPANVSGGGGSKSELVI TWETVPEELQNGRGFGYVVAFRPYGKMIWM LTVLASADASRYVFRNESVHPFSPFEVKVG VFNNKGEGPFSPTTVVYSAEE |
|---|---|---|
| SEQ ID NO: 30 | KPI domain | RAMISRWYFDVTEGK |

Example 5. Analysis on Antibody Binding Site of CNTN4 Using Anti-CNTN4 Antibody (AB1)

This example is to confirm binding between anti-CNTN4 antibody (AB1) and CNTN4 domain to confirm an antibody binding site of CNTN4.

5.1. Preparation of Anti-CNTN4 Antibody AB1

5.1.1. scFv Antibody Library Preparation and Selection

Mouse CNTN4 and/or human CNTN4 was inoculated in fifteen (15) chickens to produce the antibody. The production of the antibody was found in total four chickens under the ELISA analysis. The chickens were sacrificed, removing blood, spleen, bone marrow, and bursa fabricius, extracting total RNA, and synthesizing cDNA, to obtain a scFv fragment linking VH and VL via a linker. The phage display was then performed. Through the phase ELISA screening, positive clones binding to CNTN4 were selected and then the corresponding scFv sequences were confirmed (scFv AB1). It was labelled with constant human kappa (hCk) to be prepared and expressed in a fusion protein form, and then analyzing the binding ability to CNTN4. The amino acid sequences of VH and VL of the selected scFv AB1 were shown in Table 11 and FIG. 28.

TABLE 11

| SEQ ID NO: 31 | light chain variable region (VL) | ALTQPSSVSANLGETVKITCSGSSGS YGWYQQKSPGSAPVTLIYDNTNRPSD IPSRFSGSGSGSTGTLTITGVRAEDE AVYYCGGYDGSTDVFGAGTTLTVL |
|---|---|---|
| SEQ ID NO: 32 | heavy chain variable region (VH) | AVTLDESEGGLQTPGGALSLVCKASG FTFSSFNMFWVRQAPGKGLEYVAEIS GGGGSTWYAPAVKGRATISRDNGQST VRLQLNNLRAEDTGTYYCAKSADTWS YGAATIDAWGHGTEVIVSS |

5.1.2. Preparation of Anti-CNTN4 Chicken-Human Chimeric IgG4 Antibody AB1

Light chain and heavy chain regions of the scFv selected in 5.1.1. were cloned in a bicistronic expression vector. The transient transfection of Expi293F cell were done with the DNA, culturing up to 50% of viability, performing the IgG expression. The culture was bound to the Kappa select resin (kappa region capture) to elute IgG in the primary purification. Mabselect (Fc region capture) was then bound to remove light chain impurities and to elute IgG in the secondary purification. Anti-CNTN4 129 chimeric IgG4 antibody was prepared with purity 72.4% in SEC-HPLC analysis (hereinafter, referred to as "AB1").

5.2. Analysis on Antibody Binding Site of CNTN4

5.2.1. Preparation of Human CNTN4 Domain Sample

Human CNTN4 domain sample was prepared according to FIG. 29. CNTN4 consists of a total of ten (10) domains (i.e., Ig1 to Ig6 and FN1 to FN4; represented as Domain 1 to Domain 10, respectively, in FIG. 29). "Full" represents the sample in which all of the 10 domains are included. D1-9 was prepared by deleting Domain 10 from Full, and D1-8 was prepared by deleting Domain 9 from D1-9. In the same manner, the domain samples of D1-4 to D1-7 were prepared.

The concentration 4 μg/mL of Full domain was used as the standard, and in order to have the same molar concentration, the concentrations of the respective domains were determined in view of their molecular weights (see Table 12).

TABLE 12

| Domain Number | Full | 1-4 | 1-5 | 1-6 | 1-7 | 1-8 | 1-9 |
|---|---|---|---|---|---|---|---|
| Concentration (μg/mL) | 4 | 1.6 | 2.0 | 2.3 | 2.8 | 3.2 | 3.6 |
| Molecular Weight (kDa) | 111.08 | 44.43 | 54.48 | 64.83 | 76.83 | 87.93 | 99.03 |

5.2.2. Binding of Antibody AB1 and CNTN4 Domain Sample

CNTN4 domain as prepared in 5.2.1 was distributed in the 96-well plate by 50 μL/well. The wells were sealed with sealing tape and incubated overnight at 4° C. The next day, the sealing tape was ripped off and buffer was removed. Blocking buffer was distributed in the respective wells by 150 μL, and the wells were sealed and incubated for one hour at 37° C.

Blocking buffer was removed, and the respective primary antibody (Antibody AB1) diluted with blocking buffer as in Table 13 were distributed in the respective wells by 50 μL. The wells were sealed with sealing tape and incubated for 2 hours at 37° C. After the sealing tape was removed, the wells were washed three times.

TABLE 13

| Tube Number | 1 | 2 | 3 | 4 | 5 | 6 | 7 | 8 | 9 |
|---|---|---|---|---|---|---|---|---|---|
| Conc. (nM) | 2.5 | 0.625 | 0.156 | 0.0391 | 0.00977 | 0.00244 | 0.00061 | 0.000153 | 0.00004 |

50 μL of the diluted secondary antibody (Anti-human IgG Fc-HRP) was distributed to each well. The wells were sealed with sealing tape and incubated at 37° C. for 1 hour. The wells were washed tree times after Sealing tape was removed.

50 μL of ABTs were distributed in each well. The wells were incubated at room temperature for 30 minutes. The absorbance was detected at 405 nm by using Microplate reader.

Figures 30, 31:
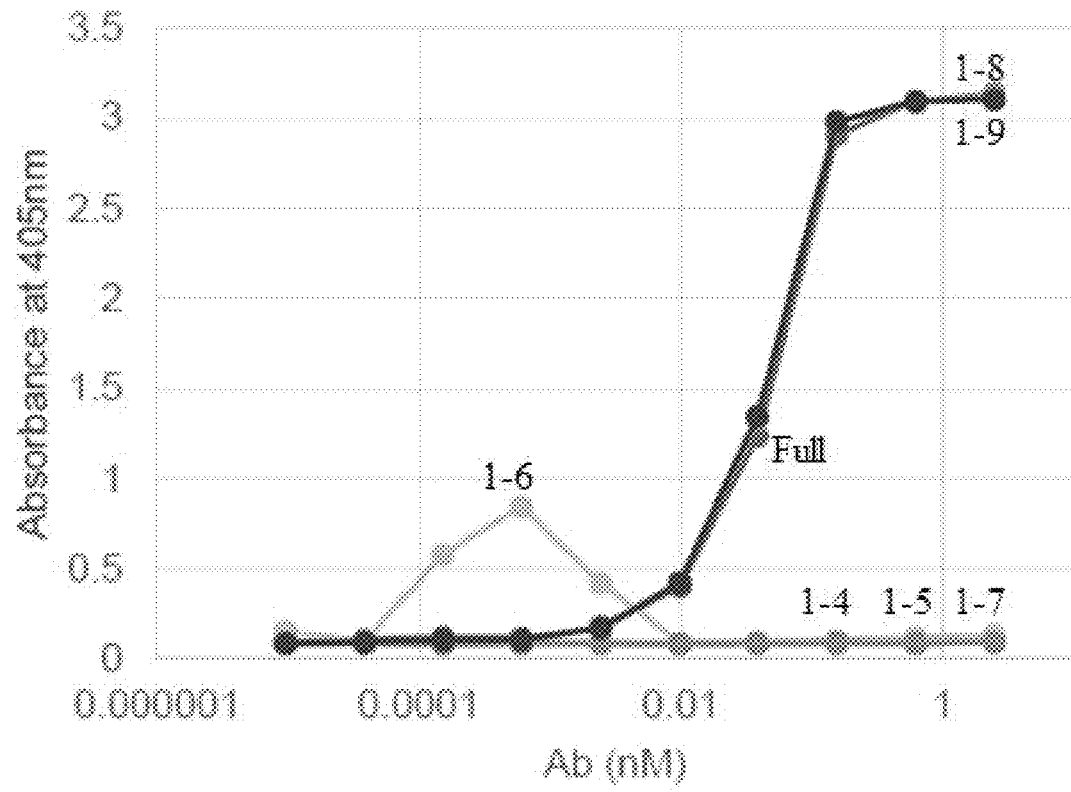
FIG. 30 is a graph depicting binding ability between anti-CNTN4 antibody AB1 and CNTN4 domain samples in accordance with Example 5.2.2.
FIG. 31 shows the amino acid sequences of Domain 8 (FN2 domain) of CNTN4.

The results were shown in Table 14 and FIG. 30.

TABLE 14

| Domain | Full | 1-4 | 1-5 | 1-6 | 1-7 | 1-8 | 1-9 |
|---|---|---|---|---|---|---|---|
| Binding | + | − | − | − | − | + | + |

Anti-CNTN4 antibody AB1 binds to only D1-8, D1-9, Full of the total 7 Human CNTN4-domain samples (three graphs were overlapped with each other in FIG. 30), whereas it does not bind to D1-4 to D1-7 (four graphs were overlapped with each other, except for D1-6 at the antibody concentration of approximately 0.0001 to 0.01 nM). Given that D1-7 and D1-8 differ in Domain 8 being present or not, it was recognized that Domain 8 (i.e., FN2) is the important binding site for the binding of CNTN4 to anti-CNTN4 antibody.

Table 15 and FIG. 31 show amino acid sequences of Domain 8 of CNTN4.

TABLE 15

| SEQ ID NO: 33 | Domain 8 (Fibronectin 2 Domain) | TPANVSGGGGSKSELVITWETVPEELQNG RGFGYVVAFRPYGKMIWMLTVLASADASR YVFRNESVHPFSPFEVKVGVFNNKGEGPF SPTTVVYSAEE |
|---|---|---|

Example 6: Analysis on Competitive Binding of APP and Antibody AB1 to CNTN4

This example is to confirm whether the binding of APP to CNTN4 is blocked by anti-CNTN4 antibody AB1.

The plate was coated with 4 mg/mL of CNTN4. APP (his tagged, 0.64 mg/mL) was diluted at 40 mg/mL using ELISA buffer. Separately, anti-CNTN4 antibody AB1 (4.98 mg/mL; 35 mM) was serially diluted by 1/10 at 1 to 0 mM by using ELISA buffer. Each of the diluted APP and AB1 antibodies was treated at 25 mL/well at 96-well half plate coated with CNTN4. The reaction was carried out at room temperature for 4 hours (in duplicate), followed by washing. Anti-his tag was diluted by 1:2,000 using ELISA buffer, treated at 50 mL/well, incubated at room temperature for 1 hour, and then washed. Subsequently, ABTS was treated at 50 μL/well. The absorbance was detected at 405 nm by using plate reader.

Figure 32:
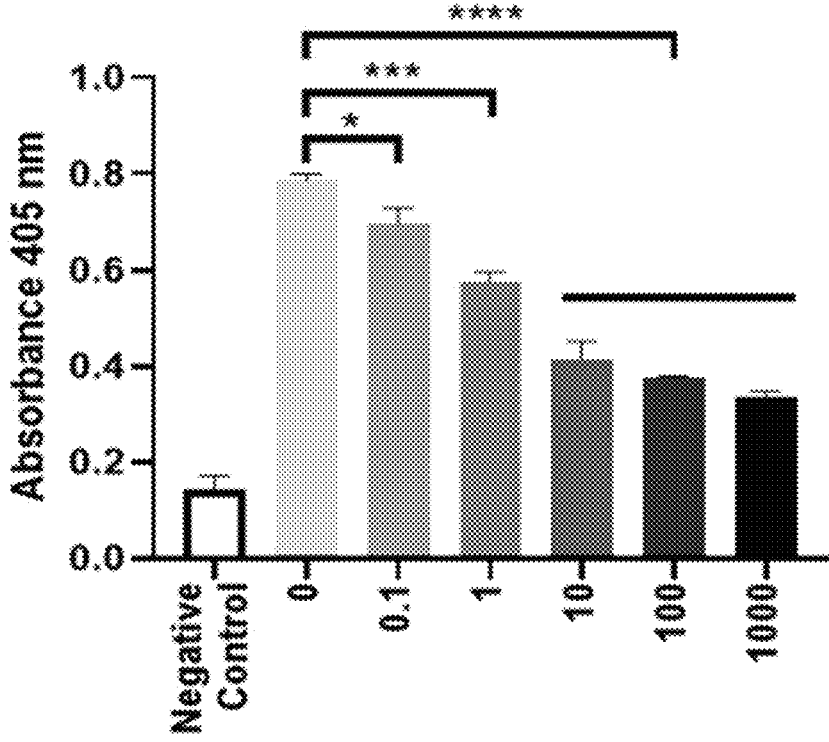
FIG. 32 is a graph depicting the competitive binding of anti-CNTN4 antibody AB1 and APP to CNTN4.

The results were shown in FIG. 32.

When APP 40 mg/mL and antibody AB1 at different concentration were treated under the condition where the plate was coated with 4 mg/mL of CNTN4, it was confirmed that the absorbance was reduced in accordance with the increase in the concentration of AB1. It shows that antibody AB1 binds to CNTN4 in competition with APP and blocks the binding of APP to CNTN4.

Those skilled in the art will recognize, or be able to ascertain using no more than routine experimentation, many equivalents to the specific embodiments of the present disclosure described herein. Such equivalents are intended to be encompassed by the following claims.

What is claimed is:

1. A method of treating a CNTN4-expressing cancer, comprising administering an inhibitor of CNTN4 to a subject in need thereof, wherein the CNTN4-expressing cancer is stomach cancer, lung cancer, liver cancer, colorectal cancer, colon cancer, small intestinal cancer, pancreatic cancer, brain cancer, bone cancer, melanoma, breast cancer, sclerosing adenosis, uterine cancer, cervical cancer, esophageal cancer, thyroid cancer, parathyroid cancer, renal cancer, sarcoma, prostate cancer, urethral cancer, bladder cancer, blood cancer, leukemia, lymphoma, or fibroadenoma.

2. The method according to claim 1, wherein the inhibitor is an antisense nucleic acid, a siRNA, a shRNA, a miRNA, or a ribozyme that binds in a complementary manner to a DNA or a mRNA of CNTN4 gene.

3. The method according to claim 1, wherein the inhibitor is a compound, a peptide, a peptide mimetic, a fusion protein, an antibody or antigen-binding fragment thereof, or an aptamer that binds specifically to CNTN4 protein.

4. The method according to claim 1, wherein the inhibitor suppresses a function of CNTN4-expressing cancer cells evading T cells.

5. The method according to claim 1, wherein the inhibitor is an anti-CNTN4 antibody or antigen-binding fragment thereof.

6. The method according to claim 5, wherein the anti-CNTN4 antibody or antigen-binding fragment thereof binds to Fibronectin 2 domain of CNTN4.

7. The method according to claim 6, wherein the Fibronectin 2 domain comprises the amino acid sequence of SEQ ID NO: 33.

8. The method according to claim 5, wherein the antibody or antigen-binding fragment thereof blocks binding of CNTN4 to amyloid precursor protein (APP).

9. The method according to claim 5, wherein the antibody or antigen-binding fragment thereof comprises a light chain variable region (VL) having the sequence of SEQ ID NO: 31 and a heavy chain variable region (VH) having the sequence of SEQ ID NO: 32.

10. A method of immune-enhancing, comprising administering an inhibitor of CNTN4 to a subject in need thereof.

11. The method according to claim 10, wherein the inhibitor inhibits expression or activity of CNTN4 in the subject to increase a level of T cell-mediated immune response.

12. The method according to claim 10, wherein the subject is in need of prevention, treatment or improvement of diseases related to immunodeficiency, lower immune function, immune system damage, or immunocompromising.

13. The method according to claim 10, wherein the inhibitor is an anti-CNTN4 antibody or antigen-binding fragment thereof.

14. The method according to claim 13, wherein the anti-CNTN4 antibody or antigen-binding fragment thereof binds to Fibronectin 2 domain of CNTN4.

15. The method according to claim 14, wherein the Fibronectin 2 domain comprises the amino acid sequence of SEQ ID NO: 33.

16. The method according to claim 13, wherein the antibody or antigen-binding fragment thereof blocks binding of CNTN4 to amyloid precursor protein (APP).

17. The method according to claim 13, wherein the antibody or antigen-binding fragment thereof comprises a light chain variable region (VL) having the sequence of SEQ ID NO: 31 and a heavy chain variable region (VH) having the sequence of SEQ ID NO: 32.

18. The method according to claim 10, wherein the inhibitor is an antisense nucleic acid, a siRNA, a shRNA, a miRNA, or a ribozyme that binds in a complementary manner to a DNA or a mRNA of CNTN4 gene.

*     *     *     *     *

SEQUENCE LISTING

<160> NUMBER OF SEQ ID NOS: 33

<210> SEQ ID NO 1
<211> LENGTH: 21
<212> TYPE: DNA
<213> ORGANISM: Artificial Sequence
<220> FEATURE:
<223> OTHER INFORMATION: human KIRREL3 siRNA_sense

<400> SEQUENCE: 1
cucucaaguu acccacagut t                                                                       21

<210> SEQ ID NO 2
<211> LENGTH: 21
<212> TYPE: DNA
<213> ORGANISM: Artificial Sequence
<220> FEATURE:
<223> OTHER INFORMATION: human KIRREL3 siRNA_antisense

<400> SEQUENCE: 2
acugugggua acuugagagt t                                                                       21

<210> SEQ ID NO 3
<211> LENGTH: 21
<212> TYPE: DNA
<213> ORGANISM: Artificial Sequence
<220> FEATURE:
<223> OTHER INFORMATION: human KIRREL3 siRNA_sense

<400> SEQUENCE: 3
ggagaggugu acaggaccat t                                                                       21

<210> SEQ ID NO 4
<211> LENGTH: 21
<212> TYPE: DNA
<213> ORGANISM: Artificial Sequence
<220> FEATURE:
<223> OTHER INFORMATION: human KIRREL3 siRNA_antisense

<400> SEQUENCE: 4
ugguccugua caccucucct t                                                                       21

<210> SEQ ID NO 5
<211> LENGTH: 21
<212> TYPE: DNA
<213> ORGANISM: Artificial Sequence
<220> FEATURE:
<223> OTHER INFORMATION: human KIRREL3 siRNA_sense

<400> SEQUENCE: 5
ucucaaguua cccacaguat t                                                                       21

<210> SEQ ID NO 6
<211> LENGTH: 21
<212> TYPE: DNA
<213> ORGANISM: Artificial Sequence
<220> FEATURE:
<223> OTHER INFORMATION: human KIRREL3 siRNA_antisense

<400> SEQUENCE: 6
uacugugggu aacuugagat t                                                                       21

<210> SEQ ID NO 7
<211> LENGTH: 21
<212> TYPE: DNA
<213> ORGANISM: Artificial Sequence -continued

```
<220> FEATURE:
<223> OTHER INFORMATION: human CNTN4 siRNA_sense

<400> SEQUENCE: 7
caguaucuuu gccagaagut t                                                    21

<210> SEQ ID NO 8
<211> LENGTH: 21
<212> TYPE: DNA
<213> ORGANISM: Artificial Sequence
<220> FEATURE:
<223> OTHER INFORMATION: human CNTN4 siRNA_antisense

<400> SEQUENCE: 8
acuucuggca aagauacugt t                                                    21

<210> SEQ ID NO 9
<211> LENGTH: 21
<212> TYPE: DNA
<213> ORGANISM: Artificial Sequence
<220> FEATURE:
<223> OTHER INFORMATION: human CNTN4 siRNA_sense

<400> SEQUENCE: 9
gauaaugagu cggaaguaat t                                                    21

<210> SEQ ID NO 10
<211> LENGTH: 21
<212> TYPE: DNA
<213> ORGANISM: Artificial Sequence
<220> FEATURE:
<223> OTHER INFORMATION: human CNTN4 siRNA_antisense

<400> SEQUENCE: 10
uuacuuccga cucauuauct t                                                    21

<210> SEQ ID NO 11
<211> LENGTH: 21
<212> TYPE: DNA
<213> ORGANISM: Artificial Sequence
<220> FEATURE:
<223> OTHER INFORMATION: human CNTN4 siRNA_sense

<400> SEQUENCE: 11
gugacaauag acgaaaucat t                                                    21

<210> SEQ ID NO 12
<211> LENGTH: 21
<212> TYPE: DNA
<213> ORGANISM: Artificial Sequence
<220> FEATURE:
<223> OTHER INFORMATION: human CNTN4 siRNA_antisense

<400> SEQUENCE: 12
ugauuucguc uauugucact t                                                    21

<210> SEQ ID NO 13
<211> LENGTH: 21
<212> TYPE: DNA
<213> ORGANISM: Artificial Sequence
<220> FEATURE:
<223> OTHER INFORMATION: human CD351 siRNA_sense

<400> SEQUENCE: 13
gagagaugaa cugcucagut t                                                    21
```

-continued

<210> SEQ ID NO 14
<211> LENGTH: 21
<212> TYPE: DNA
<213> ORGANISM: Artificial Sequence
<220> FEATURE:
<223> OTHER INFORMATION: human CD351 siRNA_antisense

<400> SEQUENCE: 14
acugagcagu ucaucucuct t                                                          21

<210> SEQ ID NO 15
<211> LENGTH: 21
<212> TYPE: DNA
<213> ORGANISM: Artificial Sequence
<220> FEATURE:
<223> OTHER INFORMATION: human CD351 siRNA_sense

<400> SEQUENCE: 15
gagaacuucc aacucaguat t                                                          21

<210> SEQ ID NO 16
<211> LENGTH: 21
<212> TYPE: DNA
<213> ORGANISM: Artificial Sequence
<220> FEATURE:
<223> OTHER INFORMATION: human CD351 siRNA_antisense

<400> SEQUENCE: 16
uacugaguug gaaguucuct t                                                          21

<210> SEQ ID NO 17
<211> LENGTH: 21
<212> TYPE: DNA
<213> ORGANISM: Artificial Sequence
<220> FEATURE:
<223> OTHER INFORMATION: human CD351 siRNA_sense

<400> SEQUENCE: 17
agagaacuuc caacucagut t                                                          21

<210> SEQ ID NO 18
<211> LENGTH: 21
<212> TYPE: DNA
<213> ORGANISM: Artificial Sequence
<220> FEATURE:
<223> OTHER INFORMATION: human CD351 siRNA_antisense

<400> SEQUENCE: 18
acugaguugg aaguucucut t                                                          21

<210> SEQ ID NO 19
<211> LENGTH: 19
<212> TYPE: RNA
<213> ORGANISM: Artificial Sequence
<220> FEATURE:
<223> OTHER INFORMATION: mouse KIRREL3 siRNA_sense

<400> SEQUENCE: 19
guaaaggaga ggucaucaa                                                             19

<210> SEQ ID NO 20
<211> LENGTH: 19
<212> TYPE: RNA
<213> ORGANISM: Artificial Sequence
<220> FEATURE:
<223> OTHER INFORMATION: mouse KIRREL3 siRNA_antisense

<400> SEQUENCE: 20
uugaugaccu cuccuuuac                                            19

<210> SEQ ID NO 21
<211> LENGTH: 19
<212> TYPE: RNA
<213> ORGANISM: Artificial Sequence
<220> FEATURE:
<223> OTHER INFORMATION: mouse CNTN4 siRNA_sense

<400> SEQUENCE: 21
guguagacaa acucucugu                                           19

<210> SEQ ID NO 22
<211> LENGTH: 19
<212> TYPE: RNA
<213> ORGANISM: Artificial Sequence
<220> FEATURE:
<223> OTHER INFORMATION: mouse CNTN4 siRNA_antisense

<400> SEQUENCE: 22
acagagaguu ugucuacac                                           19

<210> SEQ ID NO 23
<211> LENGTH: 19
<212> TYPE: RNA
<213> ORGANISM: Artificial Sequence
<220> FEATURE:
<223> OTHER INFORMATION: mouse CD351 siRNA_sense

<400> SEQUENCE: 23
guccauccaa caccaccua                                           19

<210> SEQ ID NO 24
<211> LENGTH: 19
<212> TYPE: RNA
<213> ORGANISM: Artificial Sequence
<220> FEATURE:
<223> OTHER INFORMATION: mouse CD351 siRNA_antisense

<400> SEQUENCE: 24 uaggguggugu uggauggac                                          19

<210> SEQ ID NO 25
<211> LENGTH: 19
<212> TYPE: RNA
<213> ORGANISM: Artificial Sequence
<220> FEATURE:
<223> OTHER INFORMATION: mouse CD351 siRNA_sense

<400> SEQUENCE: 25
cugaugaggg aaagaacuu                                           19

<210> SEQ ID NO 26
<211> LENGTH: 19
<212> TYPE: RNA
<213> ORGANISM: Artificial Sequence
<220> FEATURE:
<223> OTHER INFORMATION: mouse CD351 siRNA_antisense

<400> SEQUENCE: 26
aaguucuuuc ccucaucag                                           19

<210> SEQ ID NO 27

```
<211> LENGTH: 19
<212> TYPE: RNA
<213> ORGANISM: Artificial Sequence
<220> FEATURE:
<223> OTHER INFORMATION: mouse CD351 siRNA_sense

<400> SEQUENCE: 27
cagcuaagcc cagugaaca                                                   19

<210> SEQ ID NO 28
<211> LENGTH: 19
<212> TYPE: RNA
<213> ORGANISM: Artificial Sequence
<220> FEATURE:
<223> OTHER INFORMATION: mouse CD351 siRNA_antisense

<400> SEQUENCE: 28
uguucacugg gcuuagcug                                                   19

<210> SEQ ID NO 29
<211> LENGTH: 201
<212> TYPE: PRT
<213> ORGANISM: Artificial Sequence
<220> FEATURE:
<223> OTHER INFORMATION: FN1 ~ FN2 domain

<400> SEQUENCE: 29

Pro Pro Glu Ala Val Thr Ile Asp Glu Ile Thr Asp Thr Thr Ala Gln
1               5                   10                  15

Leu Ser Trp Arg Pro Gly Pro Asp Asn His Ser Pro Ile Thr Met Tyr
            20                  25                  30

Val Ile Gln Ala Arg Thr Pro Phe Ser Val Gly Trp Gln Ala Val Ser
        35                  40                  45

Thr Val Pro Glu Leu Ile Asp Gly Lys Thr Phe Thr Ala Thr Val Val
    50                  55                  60

Gly Leu Asn Pro Trp Val Glu Tyr Glu Phe Arg Thr Val Ala Ala Asn
65                  70                  75                  80

Val Ile Gly Ile Gly Glu Pro Ser Arg Pro Ser Glu Lys Arg Arg Thr
                85                  90                  95

Glu Glu Ala Leu Pro Glu Val Thr Pro Ala Asn Val Ser Gly Gly Gly
            100                 105                 110

Gly Ser Lys Ser Glu Leu Val Ile Thr Trp Glu Thr Val Pro Glu Glu
        115                 120                 125

Leu Gln Asn Gly Arg Gly Phe Gly Tyr Val Val Ala Phe Arg Pro Tyr
    130                 135                 140

Gly Lys Met Ile Trp Met Leu Thr Val Leu Ala Ser Ala Asp Ala Ser
145                 150                 155                 160

Arg Tyr Val Phe Arg Asn Glu Ser Val His Pro Phe Ser Pro Phe Glu
                165                 170                 175

Val Lys Val Gly Val Phe Asn Asn Lys Gly Glu Gly Pro Phe Ser Pro
            180                 185                 190

Thr Thr Val Val Tyr Ser Ala Glu Glu
        195                 200

<210> SEQ ID NO 30
<211> LENGTH: 15
<212> TYPE: PRT
<213> ORGANISM: Artificial Sequence
<220> FEATURE:
<223> OTHER INFORMATION: KPI domain
```

<400> SEQUENCE: 30

Arg Ala Met Ile Ser Arg Trp Tyr Phe Asp Val Thr Glu Gly Lys
1               5                   10                  15

<210> SEQ ID NO 31
<211> LENGTH: 102
<212> TYPE: PRT
<213> ORGANISM: Artificial Sequence
<220> FEATURE:
<223> OTHER INFORMATION: scFv AB1 VL

<400> SEQUENCE: 31

Ala Leu Thr Gln Pro Ser Ser Val Ser Ala Asn Leu Gly Glu Thr Val
1               5                   10                  15

Lys Ile Thr Cys Ser Gly Ser Ser Gly Ser Tyr Gly Trp Tyr Gln Gln
                20                  25                  30

Lys Ser Pro Gly Ser Ala Pro Val Thr Leu Ile Tyr Asp Asn Thr Asn
            35                  40                  45

Arg Pro Ser Asp Ile Pro Ser Arg Phe Ser Gly Ser Gly Ser Gly Ser
        50                  55                  60

Thr Gly Thr Leu Thr Ile Thr Gly Val Arg Ala Glu Asp Glu Ala Val
65                  70                  75                  80

Tyr Tyr Cys Gly Gly Tyr Asp Gly Ser Thr Asp Val Phe Gly Ala Gly
                85                  90                  95

Thr Thr Leu Thr Val Leu
            100

<210> SEQ ID NO 32
<211> LENGTH: 123
<212> TYPE: PRT
<213> ORGANISM: Artificial Sequence
<220> FEATURE:
<223> OTHER INFORMATION: scFv AB1 VH

<400> SEQUENCE: 32

Ala Val Thr Leu Asp Glu Ser Glu Gly Gly Leu Gln Thr Pro Gly Gly
1               5                   10                  15

Ala Leu Ser Leu Val Cys Lys Ala Ser Gly Phe Thr Phe Ser Ser Phe
                20                  25                  30

Asn Met Phe Trp Val Arg Gln Ala Pro Gly Lys Gly Leu Glu Tyr Val
            35                  40                  45

Ala Glu Ile Ser Gly Gly Gly Ser Thr Trp Tyr Ala Pro Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ser Ala Asp Thr Trp Ser Tyr Gly Ala Ala Thr Ile Asp Ala
            100                 105                 110

Trp Gly His Gly Thr Glu Val Ile Val Ser Ser
        115                 120

<210> SEQ ID NO 33
<211> LENGTH: 98
<212> TYPE: PRT
<213> ORGANISM: Artificial Sequence
<220> FEATURE:
<223> OTHER INFORMATION: Domain 8 (FN2 Domain)

<400> SEQUENCE: 33

-continued

```
Thr Pro Ala Asn Val Ser Gly Gly Gly Ser Lys Ser Glu Leu Val
1               5                   10                  15

Ile Thr Trp Glu Thr Val Pro Glu Glu Leu Gln Asn Gly Arg Gly Phe
            20                  25                  30

Gly Tyr Val Val Ala Phe Arg Pro Tyr Gly Lys Met Ile Trp Met Leu
        35                  40                  45

Thr Val Leu Ala Ser Ala Asp Ala Ser Arg Tyr Val Phe Arg Asn Glu
    50                  55                  60

Ser Val His Pro Phe Ser Pro Phe Glu Val Lys Val Gly Val Phe Asn
65                  70                  75                  80

Asn Lys Gly Glu Gly Pro Phe Ser Pro Thr Thr Val Val Tyr Ser Ala
                85                  90                  95

Glu Glu
```